US008476255B2

(12) United States Patent
Rajagopal et al.

(10) Patent No.: US 8,476,255 B2
(45) Date of Patent: Jul. 2, 2013

(54) HISTONE DEACETYLASE INHIBITORS

(75) Inventors: Sridharan Rajagopal, Chennai (IN);
Virendra Kachhadia, Chennai (IN);
Thanasekaran Ponpandian, Chennai
(IN); Abdul Raheem Keeri, Kanpur
(IN); Umamaheswari Mani, Chennai
(IN); Suresh Rathinasamy, Chennai
(IN); Praveen Rajendran, Corvallis, OR
(US); Kamaraj Mani, Chennai (IN);
Balaji Ramachandran, Chennai (IN);
Punthalir Narayanaswamy, Chennai
(IN); Sriram Rajagopal, Bangalore (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 429 days.

(21) Appl. No.: 12/734,026

(22) PCT Filed: Oct. 8, 2008

(86) PCT No.: PCT/IB2008/002652
§ 371 (c)(1),
(2), (4) Date: May 3, 2010

(87) PCT Pub. No.: WO2009/047615
PCT Pub. Date: Apr. 16, 2009

(65) Prior Publication Data
US 2010/0222379 A1 Sep. 2, 2010

(30) Foreign Application Priority Data

Oct. 10, 2007 (IN) ............................ 2284/CHE/2007
Jun. 20, 2008 (IN) ............................ 1508/CHE/2008

(51) Int. Cl.
A01N 43/00 (2006.01)
A61K 31/33 (2006.01)
A61K 31/16 (2006.01)
A01N 37/18 (2006.01)
C07D 215/38 (2006.01)

(52) U.S. Cl.
USPC ........................... 514/183; 514/613; 546/175

(58) Field of Classification Search
USPC ................................... 514/183, 613; 546/175
See application file for complete search history.

(56) References Cited

U.S. PATENT DOCUMENTS

| | | | |
|---|---|---|---|
| 5,369,108 A | 11/1994 | Breslow et al. | |
| 6,624,197 B1 | 9/2003 | Nag et al. | |
| 2004/0077726 A1 | 4/2004 | Watkins et al. | |
| 2004/0092598 A1 | 5/2004 | Watkins et al. | |
| 2005/0038125 A1 | 2/2005 | Smit et al. | |
| 2005/0288282 A1 | 12/2005 | Delorme et al. | |
| 2008/0139673 A1 | 6/2008 | Hu et al. | |

FOREIGN PATENT DOCUMENTS

| | | |
|---|---|---|
| WO | WO 98/55449 A1 | 12/1998 |
| WO | WO 02/26696 A1 | 4/2002 |
| WO | WO 2004/052838 A1 | 6/2004 |
| WO | WO 2004/071400 A2 | 8/2004 |
| WO | WO 2005/030705 A1 | 4/2005 |
| WO | WO 2005/097747 A1 | 10/2005 |
| WO | WO 2007/054776 A2 | 5/2007 |
| WO | WO 2008/021944 A2 | 2/2008 |

OTHER PUBLICATIONS

Vippagunta et al., Advanced Drug Delivery Reviews, 2001, vol. 48, pp. 3-26.*
Paris et al., "Histone Deacetylase Inhibitors: From Bench to Clinic," *Journal of Medicinal Chemistry*, vol. 51, No. 6, Mar. 27, 2008, pp. 1505-1529.
Marks et al., "Histone Deacetylase Inhibitors: Inducers of Differentiation or Apoptosis of Transformed Cells," *Journal of National Cancer Institute*, vol. 92, No. 15, Aug. 2, 2000, pp. 1210-1216.
Wegener at al., "Improved fluorogenic histone deacetylase assay for high-throughput-screening applications," *Analytical Biochemistry*, vol. 321, 2003, pp. 202-208.
Rodrigues et al., "Use of in vitro human metabolism studies in drug development," *Biochemical Pharmacology*, vol. 48, No. 12, 1994, pp. 2147-2156.
Mosmann, "Rapid Colorimetric Assay for Cellular Growth and Survival: Application to Proliferation and Cytotoxicity Assays," *Journal of Immunological Methods*, vol. 65, 1983, pp. 55-63.
Monks et al., "Feasibility of a High-Flux Anticancer Drug Screen Using of Diverse Panel of Cultured Human Tumor Cell Lines," *JNCI*, vol. 83, No. 11, Jun. 5, 1991, pp. 757-766.

(Continued)

Primary Examiner — Samira Jean-Louis
(74) Attorney, Agent, or Firm — Oliff & Berridge, PLC

(57) ABSTRACT

Provided herein are novel, stilbene like compounds of the general formula (I), their derivatives, analogs, tautomeric forms, stereoisomers, polymorphs, hydrates, metabolites, prodrugs, solvates, pharmaceutically acceptable salts and compositions thereof. These compounds can inhibit HDACs and are useful as a therapeutic or ameliorating agent for diseases that are involved in cellular growth such as malignant tumors, autoimmune diseases, skin diseases, infections, inflammation, etc.

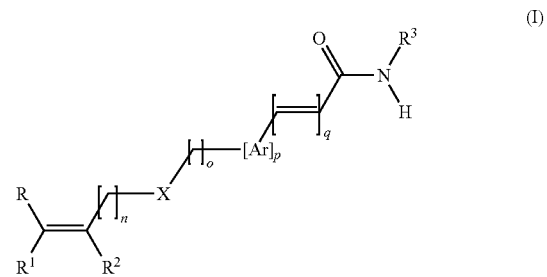

15 Claims, 1 Drawing Sheet

OTHER PUBLICATIONS

Finn et al., "Novel Sulfonamide Derivatives as Inhibitors of Histone Deacetylase," *Helvetica Chimica Acta*, vol. 88, 2005, pp. 1630-1657.
Partial International Search Report issued for International Application No. PCT/IB2008/002652 on Jan. 19, 2010.
Written Opinion issued for International Application No. PCT/IB2008/002652 on Jan. 19, 2010.
International Search Report issued for International Application No. PCT/IB2008/002652 on May 11, 2010.
Written Opinion issued for International Application No. PCT/IB2008/002652 on May 11, 2010.
Elaut et al., The Pharmaceutical Potential of Histone Deacetylase Inhibitors, *Current Pharmaceutical Design*, (2007), vol. 13, pp. 2584-2620.

\* cited by examiner

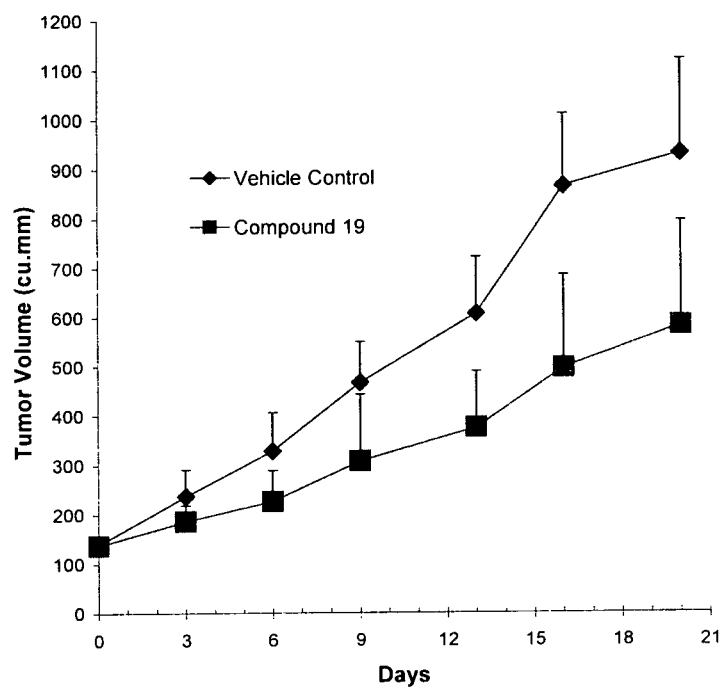

HISTONE DEACETYLASE INHIBITORS

FIELD

Described are novel stilbene like compounds of the general formula (I), their derivatives, analogs, tautomeric forms, stereoisomers, polymorphs, hydrates, solvates, pharmaceutically acceptable salts and compositions, metabolites and prodrugs thereof.

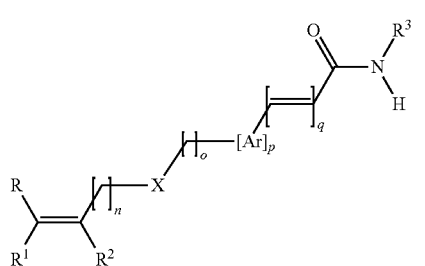

Described herein is the process for the preparation of the above said novel stilbene like compounds of the formula (I), their derivatives, analogs, stereoisomers, polymorphs, hydrates, solvates, pharmaceutically acceptable salts and compositions, metabolites and prodrugs thereof.

These compounds described herein are inhibitors of Histone deacetylase (HDAC) and also arrest cell growth in neoplastic cells, thereby inhibiting proliferation. The compounds provided herein can be used as therapeutic agents for diseases that are involved in cellular growth such as malignant tumors, autoimmune diseases, skin diseases, infections etc.

BACKGROUND

Transcriptional regulation is a major event in cell differentiation, proliferation and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription factors to their target DNA regiments. Nucleosomal integrity is regulated by the acetylating status of the core histone, with the result being permissiveness to transcription.

The regulations of transcription factor are thought to involve by changes in the structure of chromatin. Changing its affinity of histone proteins for coiled DNA in the nucleosome alters the structure of chromatin. Hypoacetylated histones are believed to have greater affinity to the DNA and form a tightly bound DNA-histone complex and render the DNA inaccessible to transcriptional regulation. The acetylating status of the histone is governed by the balance activities of the histone acetyl transferase (HAT) and histone deacetylase (HDAC).

The first isolation of histone deacetylase was described in 1964 from crude nuclear extracts of cells, but the molecular characterization of isoforms of the enzyme has been achieved recently. Inhibitors of histone deacetylase (HDACs) are zinc hydrolases responsible for the deacetylation of N-acetyl lysine residues of histone and non-histone protein substrates. Human HDACs are classified into two distinct classes, the HDACs and sirtuins. The HDACs are divided into two subclasses based on their similarity to yeast histone deacetylases, RPD 3 (class I includes HDAC 1, 2, 3, 8, and 11) and Hda 1 (class II includes HDAC 4, 6, 7, 9, and 10). All of the HDACs have a highly conserved zinc dependent catalytic domain. There is growing evidence that the acetylation state of proteins and thus the HDAC enzyme family plays a crucial role in the modulation of a number of biological processes, including transcription and cell cycle.

Recently, HDAC inhibitors have been found to arrest growth and apoptosis in several types of cancer cells, including colon cancer, t-cell lymphoma and erythroleukemic cells (M. Paris, et. al., *J. Med. Chem.*, 2008, 51, 1505-1529).

HDAC inhibitor MG3290 was found to be a potent, fungal selective potentiator of several azole antifungals in *Aspergillus* and *Candida* species including *C. glabrata* and also it was found to potentiate azole resistant *C-glabrata* mutant (WO 2008/021944 and US 2008/0139673).

Given that apoptosis is a crucial factor for cancer progression, HDAC inhibitors are promising reagents for cancer therapy as effective inducers of apoptosis.

Recently, suberoylanilide hydroxamic acid (SAHA) was launched as an antitumor agent for treating cutaneous T-cell lymphoma (CTCL) and is a known HDAC inhibitor. Several structural classes of HDAC inhibitors have been identified and are reviewed in Marks, P. A. et al., *J. Natl. Cancer Inst.*, 2000, 92, 1210-1215. More specifically WO 98/55449 and U.S. Pat. No. 5,369,108 patents report alkanoyl hydroxamates with HDAC inhibitory activity. Other compounds that are able to inhibit HDAC activity are Trichostatin A (TSA), PXD101, Tropoxin (TPX), Sodium butyrate (NaB), Sodium valproate (VPA), Cyclic hydroxamic acid containing peptides (CHAPs), Depsipeptide FK-228, MGCD0103 and MS-275 can derepress these genes, resulting in antiproliferative effects in vitro and anti tumor effects in vivo.

1) US 20040092598 pertains to certain active carbamic acid compounds which inhibit HDAC activity and which have the formula (A). The invention described in this patent application also pertains to pharmaceutical compositions comprising such compounds, and the use of such compounds and compositions, both in vitro and in vivo, to inhibit HDAC and e.g. to inhibit proliferative conditions, such as Cancer and Psoriasis.

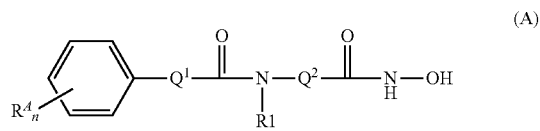

Wherein, $Q^1$ is selected from,

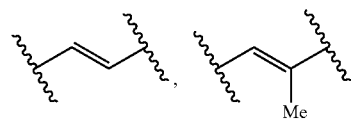

In one preferred embodiment, $Q^2$ is selected from:

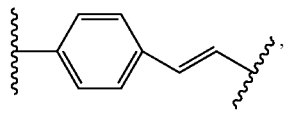

-continued

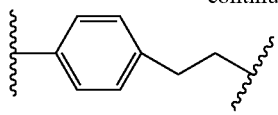

Wherein, n represents 0-3 and $R^4$ represents fluoro, chloro, bromo, iodo, methyl, ethyl, cyano, hydroxy, methoxy and ethoxy.

2) U.S. Pat. No. 6,624,197 B1 discloses a class of diphenyl-ethylenes of the formula A,

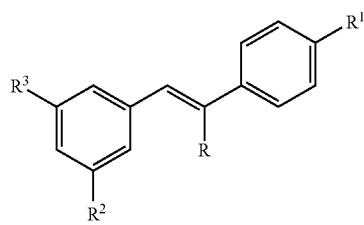

A

Wherein R is hydrogen or —$CO_2Z$, Z is hydrogen or a cation; and $R^1$, $R^2$ and $R^3$ are each independently H, —OH or —OW, wherein $R^4$ is linear or branched alkyl of 1-12 carbon atoms; with the condition that when R is hydrogen and $R^2=R^3=$—OMe, then $R^1$ is not —OH. The configuration around the double bond may be E/Z. A class of styrenes of the formula B is also provided;

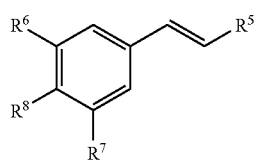

B

Wherein $R^5$ is hydrogen or methyl; $R^6$ and $R^7$ are independently hydrogen or OMe; $R^8$ is hydrogen or hydroxy. The configuration around the double bond may be E/Z. Pharmaceutical compositions of compounds of the formula A or B are provided for the treatment of diabetes comprising of therapeutically effective amount of the compounds in a physiologically acceptable carrier. A method of treating diabetes is also provided comprising a step of orally administering to a subject suffering from a diabetic condition a therapeutically effective amount of a compound of formula A or B.

3) US 20050038125 describes a method for the treatment and/or prevention of disorders with elevated $PGE_2$ (such as arthritis, fybromyalgia and pain) and/or $LTB_4$ levels (such as asthma, allergy, arthritis, fybromyalgia and inflammation), comprising administering to a mammal an effective amount of pterostilbene component (PS component), a pharmaceutically acceptable salt of PS component or a precursor of PS component, wherein the PS component has the formula C.

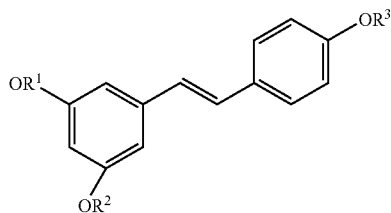

C

In which $R^1$, $R^2$ and $R^3$ are independently selected from hydrogen, $C_{1-50}$ hydrocarbyl, $C_{1-50}$ substituted hydrocarbyl, $C_{1-50}$ heterohydrocarbyl, $C_{1-50}$ substituted heterohydrocarbyl; and wherein at least one of $R^1$ and $R^2$ is not hydrogen.

4) US 2004/0077726 A1 discloses certain active carbamic acid compounds, which inhibit HDAC activity and have the following formula D,

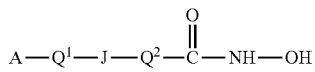

D

Wherein A is an aryl group; $Q^1$ is a covalent bond or an aryl leader group; J is a sulfonamide linkage selected from: —S($=$O)$_2$NR$^1$— and —NR$^1$S($=$O)$_2$—; $R^1$ is a sulfonamido substituent; and $Q^2$ is an acid leader group; with the proviso that if J is —S($=$O)$_2$NR$^1$—, then $Q^1$ is an aryl leader group; and pharmaceutically acceptable salts, solvates, amides, esters, ethers, chemically protected forms and prodrugs thereof. Pharmaceutical compositions comprising such compounds, and their use to inhibit proliferative conditions are described. Compounds of formula E, wherein $Q^1$ is a covalent bond, J is —NR$^1$SO$_2$—, $Q^2$ is phenylene-meta-trans-ethylene are also described. $R^B$ represents fluoro, chloro, methyl, ethyl, isopropyl, t-butyl, trifluoromethyl, hydroxy, methoxy, ethoxy, isopropoxy, methylthio, amino, dimethylamino, diethylamino, morpholino, acetamido, nitro and phenyl. m is an integer from 0 to 4.

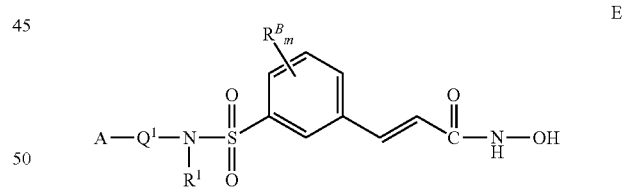

E

5) WO2004/071400 A2 discloses certain active benzamide compounds, which inhibit HDAC activity and have the following formula F,

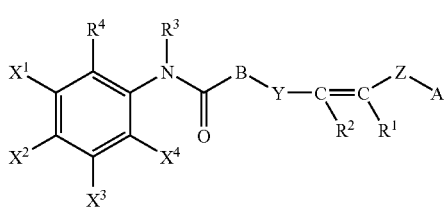

F where in A is a phenyl or heterocyclic group, B is a phenyl or heterocyclic hroup. Z is a bond or optionally substituted alkylene having 1 to 4 carbons or a moiety having —O—, —S—, —NH, —CO, —CS, —SO— or —SO$_2$— which is linear, cyclic or their combination; Y is a moiety having —CO—, —CS—, —SO— or —SO$_2$— which is linear, cyclic or a combination thereof; $R^1$ and $R^2$ are independently a hydrogen or an optionally substituted alkyl having 1 to 4 carbons; or $R^1$ and $R^2$ may form a bond; $R^3$ is a hydrogen or an optionally substituted alkyl having 1 to 4 carbons; $R^4$ is a hydrogen atom or an amino group etc. $X^1$, $X^2$, $X^3$ and $X^4$ are a halogen atom, a hydroxyl group, an amino group etc. Specific structure G is disclosed in this patent

G

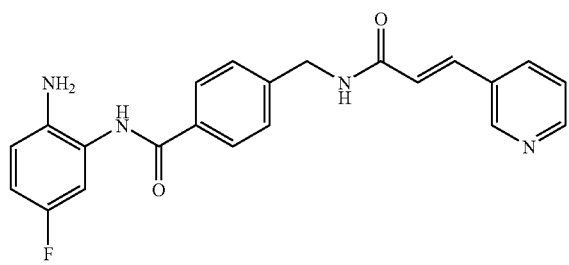

6) WO2007/054776 discloses certain active hydroxy compounds, which inhibit HDAC activity and have the following formula H,

H

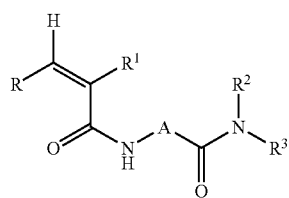

Wherein A represents —(CH$_2$)$_n$— which is optionally substituted or unsubstituted by groups selected from aryl, arylalkyl and heteroaryl which may be further substituted; R and $R^1$ represents aryl groups, heteroaryl groups and benzofused heteroaryl groups; $R^2$ and $R^3$ may be selected from hydrogen, hydroxyl, alkyl groups, alkoxy groups, cycloalkyl groups, aryl groups, heteroaryl groups and n is an integer in the range of 1 to 8.

SUMMARY

Described are novel stilbene like compounds of the general formula (I), (I)

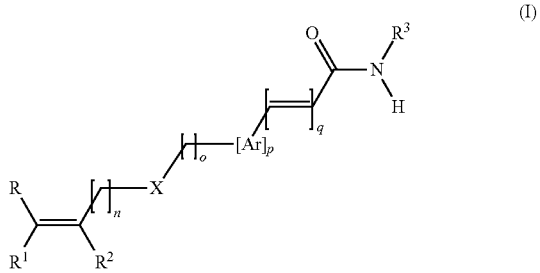

their derivatives, analogs, tautomeric forms, stereoisomers, polymorphs, solvates, pharmaceutically acceptable salts and compositions, metabolites and prodrugs thereof, wherein, the configuration around the double bonds may be E/Z, wherein $R^1$ and $R^2$ represent substituted or unsubstituted groups selected from aryl, cycloalkyl, cycloalkenyl, arylalkenyl, heteroarylalkenyl, arylalkynyl, heterocyclyl and heteroaryl;

R represents H, substituted or unsubstituted groups selected from alkyl, aryl, heteroaryl and heterocyclyl;

X represents a group selected from —CONR$^4$—, —NR$^4$SO$_2$—, —SO$_2$NR$^4$—, —SO$_2$O—, O—SO$_2$—, —CONR$^4$CONR$^4$—, —NR$^4$CO—, —OCONR$^4$—, —NR$^4$CONR$^4$—, —NR$^4$—, —O—; wherein $R^4$ represents H or substituted or unsubstituted groups selected from alkyl, aryl, heterocyclyl, heteroaryl cycloalkyl and cycloalkenyl;

Ar represents substituted or unsubstituted groups selected from aryl and heteroaryl;

$R^3$ represents a group selected from ortho substituted aniline, phenol, amino aryl, hydroxy aryl, amino heteroaryl and —OR$^5$; $R^5$ represents a group selected from H, —COR$^6$, substituted or unsubstituted groups selected from alkyl, aryl and heterocyclyl; $R^6$ represents substituted or unsubstituted groups selected from alkyl, aryl and heterocyclyl;

wherein n=0 or 1, o=0-6, p=0 or 1, q=0-3;

with the proviso that if p, q and n=0, then o=4-6; and with the proviso that if p=1, then o=0 or 1; and with the proviso that if X=—OCONH—, then n and p=1.

BRIEF DESCRIPTION OF THE DRAWING

FIG. 1 shows the efficacy of compound 19 in HCT-116 xenograft model.

DETAILED DESCRIPTION

Described are novel stilbene like compounds of the general formula (I), (I)

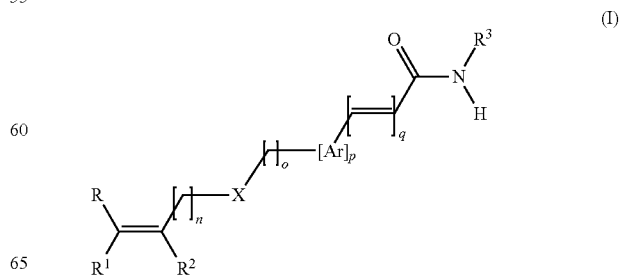

their derivatives, analogs, tautomeric forms, stereoisomers, polymorphs, solvates, pharmaceutically acceptable salts and compositions, metabolites and prodrugs thereof, wherein, the configuration around the double bonds may be E/Z, wherein $R^1$ and $R^2$ represent substituted or unsubstituted groups selected from aryl, cycloalkyl, cycloalkenyl, arylalkenyl, heteroarylalkenyl, arylalkynyl, heterocyclyl and heteroaryl;

R represents H, substituted or unsubstituted groups selected from alkyl, aryl, heteroaryl and heterocyclyl;

X represents a group selected from —$CONR^4$—, —$NR^4SO_2$—, —$SO_2NR^4$—, —$SO_2O$—, —O—$SO_2$—, —$CONR^4CONR^4$—, —$NR^4CO$—, —$OCONR^4$—, —$NR^4CONR^4$—, —$NR^4$— and —O—; $R^4$ represents H, substituted or unsubstituted groups selected from alkyl, aryl, heterocyclyl, heteroaryl and cycloalkyl and cycloalkenyl;

Ar represents substituted or unsubstituted groups selected from aryl and heteroaryl;

$R^3$ represents a group selected from ortho substituted aniline, phenol, amino aryl, hydroxy aryl, amino heteroaryl or —$OR^5$; $R^5$ represents H, —$COR^6$, substituted or unsubstituted groups selected from alkyl, aryl and heterocyclyl; $R^6$ represents substituted or unsubstituted groups selected from alkyl, aryl and heterocyclyl;

wherein n=0 or 1, o=0-6, p=0 or 1, q=0-3;

with the proviso that if p, q and n=0, then o=4-6; and with the proviso that if p=1, then o=0 or 1; and with the proviso that if X=—OCONH—, then n and p=1.

When the groups R, $R^1$, $R^2$, $R^4$ and Ar have one or more substitutents, the substituents are selected from halogens such as fluorine, chlorine, bromine and iodine; hydroxy; nitro; cyano; azido; nitroso; amino; hydrazino; formyl; alkyl; alkenyl; alkynyl; haloalkyl group such as trifluoromethyl, trichloromethyl, dichloromethyl and difluoromethyl; haloalkoxy group such as —O—$CH_2$-halo; aralkoxy such as benzyloxy and phenylethoxy; cycloalkyl; aryl; alkoxy; aryloxy; acyl; acyloxy; acyloxyacyl; heterocyclyl; heteroaryl; alkylamino groups such as monoalkylamino and dialkylamino; acylamino; alkoxycarbonyl; aryloxycarbonyl; alkylsulfonyl; arylsulfonyl; alkylsulfinyl; arylsulfinyl; alkylthio; arylthio; sulfamoyl; alkoxyalkyl groups and carboxylic acids and its derivatives such as ester, amide and the like; which in turn are optionally substituted by hydroxy; nitro; cyano; azido; nitroso; amino; hydrazine; halogen; alkyl; alkoxy; aryl; cycloalkyl and heteroaryl.

Furthermore, whenever the groups R, $R^1$, $R^2$ and Ar represent substituted or unsubstituted 5 to 10 membered ring systems, the rings may be monocyclic, bicyclic or polycyclic, saturated, partially saturated or aromatic containing 1 to 4 heteroatoms selected from O, S and N.

The term "aryl" refers to aromatic radicals having 6 to 14 carbon atoms such as phenyl, naphthyl, biphenyl, indanyl, substituted or unsubstituted arylene group such as phenylene, biphenylene, naphthylene, anthracenylene, phenathrylene and indanylene.

The term "heterocyclyl" refers to a stable 3 to 15 membered ring radical, which consists of carbon atoms and from about one to five heteroatoms selected from nitrogen, phosphorus, oxygen and sulfur. For purposes of this invention the heterocyclic ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. Examples of such heterocyclic ring radicals include but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, qunioxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quiniclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, thienyl, morpholinyl, thiomorpholinyl, thiamorpholinyl sulfoxide, furyl, tetrahydropuryl, tetrahydropyranyl, chromanyl, isochromanyl and the like. The heterocyclyl ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom. Examples of such heteroaryl groups include but are not limited to, pyridinyl, pyridazinyl, pyrimidyl, pyrazyl, triazinyl, pyrrolyl, pyrazolyl, imidazolyl, pyrazinyl, pyrimidinyl, tetrazolyl, furyl, thienyl, isoxazolyl, thiazolyl, isoxazolyl, oxazolyl, quinolinyl, isoquinolinyl, indolyl, azaindolyl, benzothiazolyl, benzimidazolyl, benzothienyl, benzopyranyl, benzoxazolyl and the like. The term heteroaryl also refers to heteroarylene. Examples of such heteroarylene groups include but are not limited to pyridinylene, pyridazinylene, pyrimidylene, pyrazylene, triazinylene, pyrrolylene, pyrazolylene, imidazolylene, pyrazinylene, pyrimidinylene.

The term "alkyl" refers to a straight or branched aliphatic hydrocarbon groups having the specified number of carbon atoms, which attached to the rest of the molecule by a single atom. Examples of such alkyl groups include but are not limited to, methyl, ethyl, n-propyl, isopropyl, butyl, isobutyl, t-butyl pentyl, hexyl, heptyl, octyl and the like.

The term "cycloalkyl" refers to non-aromatic mono or polycyclic ring system of about 3 to 12 carbon atoms. Examples of such cycloalkyl groups include but are not limited to, cyclopropyl, cyclobutyl, cyclopentyl, cyclohexyl, cyclooctanyl and the like; Examples of non-aromatic mono or polycyclic rings include but are not limited to, perhydronaphthyl, adamantyl, noradamantyl and norbonyl groups, bridged cyclic groups or spirobicyclic groups e.g spiro[4.4] non-2-yl.

The term "cycloalkenyl" refers to a non-aromatic cyclic ring containing radical containing about 3 to 8 carbon atoms with at least one carbon-carbon double bond. Examples of such cycloalkenyl groups include but are not limited to, cyclopentenyl, cyclohexenyl, cycloheptenyl and cyclooctenyl and the like.

The term "alkenyl" refers to an aliphatic hydrocarbon group containing a carbon-carbon double bond and which may be straight or branched chain having about 2 to 10 carbon atoms. Examples of such alkenyl groups include but are not limited to, ethenyl, 1-propenyl, 2-propenyl, iso-propenyl, 2-methyl-1-propenyl, 1-butenyl, 2-butenyl and the like.

The term "arylalkenyl" refers to an aromatic ring radical directly bonded to an alkenyl group. The aryl radical may be attached to the main structure at any carbon from the alkenyl group. Examples of such arylalkenyl groups include but are not limited to, phenylethenyl, phenylpropenyl and the like.

The term "heteroarylalkenyl" refers to a heteroaryl ring radical directly bonded to an alkenyl group. The heteroaryl radical may be attached to the main structure at any carbon from the alkenyl group. Examples of such heteroarylalkenyl groups include but are not limited to, thienylpropenyl, indolylpropenyl and the like.

The term "alkoxy" refers to an alkyl group attached via an oxygen linkage to the rest of the molecule. Examples of those groups include but are not limited to, —OCH$_3$, —OC$_2$H$_5$ and the like.

The term "alkylthio" refers to an alkyl group attached via a sulfur linkage to the rest of the molecule. Representative examples of those groups include, but are not limited to, —SCH$_3$ and —SC$_2$H$_5$.

The term "aryloxy" refers to an aryl group attached via an oxygen linkage to the rest of the molecule. Representative examples of those groups include, but not limited to —O-phenyl and —O-biphenyl.

The term "alkylamino" refers to an alkyl group as defined above attached via amino linkage to the rest of the molecule. Representative examples of those groups include, but not limited to —NHCH$_3$ and —N(CH$_3$)$_2$.

The term "alkynyl" refers to a straight or branched hydrocarbyl radicals having at least one carbon-carbon triple bond and having in the range of 2-12 carbon atoms. Examples of such alkynyl groups include but are not limited to, ethynyl, propynyl, butynyl and the like.

The term "arylalkynyl" refers to an aromatic ring radical directly bonded to an alkynyl group. The aryl radical may be attached to the main structure at any carbon from the alkynyl group. Examples of such arylalkynyl groups include but are not limited to, phenylethynyl and phenylpropynyl and the like.

The term "heteroarylalkynyl" refers to a heteroaryl radical directly bonded to an alkynyl group. The heteroaryl radical may be attached to the main structure at any carbon from the alkynyl group.

Furthermore, the compound of formula (I) can be its derivatives, analogs, tautomeric forms, stereoisomers, geometrical isomers, polymorphs, solvates, intermediates, metabolites, prodrugs or pharmaceutically acceptable salts and compositions.

Pharmaceutically acceptable solvates may be hydrates or comprising of other solvents of crystallization such as alcohols.

The compounds described herein can be either in E or Z geometrical isomers and in some cases mixtures can also be present. In cases where two or more double bonds are present in formula I, can give rise to more than two geometrical isomers and in these cases the invention is said to cover all the isomers.

It is understood that included in the family of compounds of Formula (I) are isomeric forms including tautomers and stereoisomers (diastereoisomers, enantiomers and geometrical isomers in "E" or "Z" configurational isomer or a mixture of E and Z isomers). It is also understood that some isomeric form such as diastereomers, enantiomers and geometrical isomers can be separated by physical and/or chemical methods and by those skilled in the art.

Compounds disclosed herein may exist as single stereoisomers, racemates and or mixtures of enantiomers and or/diastereomers. All such single stereoisomers, racemates and mixtures thereof are intended to be within the scope of the subject matter described.

The phrase "pharmaceutically acceptable" refers to compounds or compositions that are physiologically tolerable and do not typically produce allergic or similar untoward reaction, including but are not limited to, gastric upset or dizziness when administered to mammal.

Pharmaceutically acceptable salts include salts derived from inorganic bases such as like Li, Na, K, Ca, Mg, Fe, Cu, Zn and Mn; salts of organic bases such as N,N'-diacetylethylenediamine, glucamine, triethylamine, choline, hydroxide, dicyclohexylamine, benzylamine, trialkylamine and thiamine, guanidine, diethanolamine, α-phenylethylamine, piperidine, morpholine, pyridine, hydroxyethylpyrrolidine, hydroxyethylpiperidine, and the like, ammonium or substituted ammonium salts, aluminum salts. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like.

In another embodiment, described herein, encompasses prodrugs of a compound, which on administration undergoes chemical conversion by metabolic processes before becoming active pharmacological substances. In general, such prodrugs will be functional derivatives of a compound of the invention, which are readily convertible in vivo into a compound of the invention.

"Prodrug" means a compound, which is convertible in vivo by metabolic means (that is by hydrolysis, reduction or oxidation) to a compound of formula (I). For example an ester prodrug of a compound of formula (I) containing hydroxyl group may be convertible by hydrolysis in vivo to the parent molecule.

The active compounds disclosed can also be prepared in any solid or liquid physical form, for example the compound can be in a crystalline form, in amorphous form and have any particle size. Furthermore, the compound particles may be micronized or nanoized, or may be agglomerated, particulate granules, powders, oils, oily suspensions or any other form of solid or liquid physical forms.

Described herein also provides a pharmaceutical composition, containing one or more of the compounds of the general formula (I) as defined above, their derivatives, analogs, tautomeric forms, stereoisomers, polymorphs, hydrates, metabolites, prodrugs, pharmaceutically acceptable salts, pharmaceutically acceptable solvates in combination with the usual pharmaceutically employed carriers, diluents and the like, useful for the treatment of and/or proliferative disorders.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. Suitable pharmaceutically acceptable carriers include solid fillers or diluents and sterile aqueous or organic solutions. The active compound will be present in such pharmaceutical compositions in the amounts sufficient to provide the desired dosage in the range as described above. Suitable routes of administration include systemic, such as orally or by parenteral administration such as subcutaneous, intramuscular, intravenous and intradermal routes. Thus for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly.

The compounds of formula (I) can also be administered as a pharmaceutical composition in a pharmaceutically acceptable carrier, preferably formulated for oral administration.

The compounds described herein may also exhibit polymorphism. This invention further includes different polymorphs of the compounds. The term polymorph refers to a particular crystalline state of a substance, having particular physical properties such as X-ray diffraction, IR spectra, melting point and the like.

This invention, in addition to the above listed compounds, is intended to encompass the use of homologs and analogs of such compounds. In this context, homologs are molecules having substantial structural similarities to the above described compounds and analogs are molecules having substantial biological similarities regardless of structural similarities.

The term 'histone deacetylase inhibitor' or 'inhibitor of histone deacetylase' is used to identify a compound which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of histone deacetylase to remove an acetyl group from a histone at a concentration that is lower than the concentration of the inhibitor that is required to produce some other, unrelated biological effect.

The term 'histone deacetylase' and 'HDAC' are intended to refer to any one of a family of enzymes that remove acetyl groups from the $\epsilon$-amino groups of lysine residues at the N-terminus of a histone. Unless otherwise indicated by context, the term "histone" is meant to refer to any histone protein, including H1, H2A, H2B, H3, H4 and H5, from any species. Human HDAC proteins or gene products include but are not limited to, HDAC-1, HDAC-2, HDAC-3, HDAC-4, HDAC-5, HDAC-6, HDAC-7, HDAC-8, HDAC-9 and HDAC-10. The histone deacetylase can also be derived from a protozoal or fungal source.

The invention also provides a method of treatment of cancer in patient including administration of a therapeutically effective amount of a compound formula (I).

The present invention provides a method of treatment of a disorder caused by, associated with or accompanied by disruptions of cell proliferation and/or angiogenesis including administration of a therapeutically effective amount of a compound of formula (I).

The embodiment is a proliferative disorder. In one other embodiment the disorder is selected from the group consisting of but are not limited to, cancer, inflammatory diseases/immune disorder, fibrotic diseases (e.g liver fibrosis), diabetes, autoimmune disease, chronic and acute neurodegenerative disease, Huntington's disease and infectious disease.

In one aspect of the preferred embodiment the compounds described herein are used in the treatment or prevention of cancer. The cancer can include solid tumors or hematologic malignancies.

The present invention provides a method of treatment of a disorder, disease or condition that can be treated by the inhibition of HDAC enzymes including administration of therapeutically effective amount of compound of formula (I).

The invention provides a method of treatment of cancer in patient including administration of effective amount of formula (I). The cancer can be either hematologic malignancy and this form of malignancy is selected from the group consisting of B-cell lymphoma, T-cell lymphoma and leukemia. In the case of solid tumors, the tumors is selected from the group consisting of breast cancer, lung cancer, ovarian cancer, prostate cancer, head and neck cancer, renal cancer, gastric cancer, colon cancer, pancreatic cancer and brain cancer.

The term "therapeutically effective amount" or "effective amount" is an amount sufficient to effect beneficial or desired results. An effective amount can be administered in one or more administrations. An effective amount is typically sufficient to palliate, ameliorate, stabilize, reverse, slow or delay the progression of the disease state.

In another aspect, the compound may be administered in combination therapy by combining the compound of formula (I) with one or more separate agents, not limited to targets such as HDAC, DNA methyltransferase, heat shock proteins (e.g. HSP90) kinase and other matrix metalloproteinases.

"Combination therapy" includes the administration of the subject compounds in further combination with other biologically active ingredients (such as, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of the invention. The compounds can be administered simultaneously or sequentially to the other drug therapy.

In another aspect, the subject compounds may be combined with the antineoplastic agents (e.g. small molecules, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In another aspect, the subject compounds may be combined with the antifungal agents (e.g. Azoles) that inhibit one or more biological targets. Such combination may enhance therapeutic efficacy over the efficacy achieved by any of the agents alone and may prevent or delay the appearance of resistant variants.

In certain preferred embodiments, the compounds of the invention are administered in combination with chemotherapeutic agents. Chemotherapeutic agents consist of a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment.

The term "subject" as used herein is meant to include all mammals, and in particular humans, in need of treatment. The therapeutically effective amount will vary depending upon the subject and disease condition being treated, the weight and age of the subject, the severity of the disease condition, the particular compound Of formula (I) chosen, the dosing regimen to be followed, timing of administration, the manner of administration and the like, all of which can readily be determined by one of ordinary skill in the art.

Representative compounds include:
1.    N-(2-Aminophenyl)-4-((3-(3,4-difluorophenyl)-2-(4-fluorophenyl)acrylamido)methyl)benzamide;

2. N-(2-Aminophenyl)-4-((3-(4-methoxyphenyl)-2-(phenyl)acrylamido)methyl)benzamide;
3. N-(2-Aminophenyl)-4-((3-(2-fluorophenyl)-2-(4-chlorophenyl)acrylamido)methyl)benzamide;
4. N-(2-Aminophenyl)-4-((3-(4-fluoro-3-trifluoromethylphenyl)-2-(4-trifluoromethylphenyl)acrylamido)methyl)benzamide;
5. N-(2-Aminophenyl)-4-((3-(4-fluoro-3-trifluoromethylphenyl)-2-(4-nitrophenyl)acrylamido)methyl)benzamide;
6. N-(2-Aminophenyl)-4-((3-(4-methylthiophenyl)-2-(4-fluorophenyl)acrylamido)methyl)benzamide;
7. N-(2-Aminophenyl)-4-((3-(5-nitrothiophen-2-yl)-2-(4-fluorophenyl)acrylamido)methyl)benzamide;
8. N-(2-Aminophenyl)-4-((3-(3,4,5-trimethoxyphenyl)-2-(4-fluorophenyl)acrylamido)methyl)benzamide;
9. N-(2-Aminophenyl)-4-((3-(2-chloro-4-fluorophenyl)-2-(phenyl)acrylamido)methyl)benzamide;
10. N-(2-Aminophenyl)-4-((3-(4-fluorophenyl)-2-(phenyl)acrylamido)methyl)benzamide;
11. N-(2-Aminophenyl)-4-((3-(4-methoxyphenyl)-2-(4-fluorophenyl)acrylamido)methyl)benzamide;
12. N-(2-Aminophenyl)-4-((3-phenyl-2-phenylacrylamido)methyl)benzamide;
13. N-(2-Aminophenyl)-4-((3-(2,4,6-trifluorophenyl)-2-(4-fluorophenyl)acrylamido)methyl)benzamide;
14. N-(2-Aminophenyl)-4-((3-(cyclopropyl)-2-(4-fluorophenyl)acrylamido)methyl)benzamide;
15. N-(2-Aminophenyl)-4-((3-(pyridin-4-yl)-2-(4-fluorophenyl)acrylamido)methyl)benzamide;
16. N-(2-Aminophenyl)-4-((3-(4-methylthiophenyl)-2-(4-methoxyphenyl)acrylamido)methyl)benzamide;
17. N-(2-Aminophenyl)-4-((3-(3,5-dimethoxyphenyl)-2-(4-fluorophenyl)acrylamido)methyl)benzamide;
18. N-(2-Aminophenyl)-4-((3-(4-methylthiophenyl)-2-(thiophen-2-yl)acrylamido)methyl)benzamide;
19. N-(2-Aminophenyl)-4-((3-(3,4-dimethoxyphenyl)-2-(4-fluorophenyl)acrylamido)methyl)benzamide;
20. N-(2-Aminophenyl)-4-((3-(4-fluoro-3-methoxyphenyl)-2-(4-fluorophenyl)acrylamido)methyl)benzamide;
21. N-(2-Aminophenyl)-4-((3-(4-methylthiophenyl)-2-(4-trifluoromethylphenyl)acrylamido)methyl)benzamide;
22. N-(2-Aminophenyl)-4-((3-(quinolin-4-yl)-2-(4-fluorophenyl)acrylamido)methyl)benzamide;
23. N-(2-Aminophenyl)-4-((3-(4-methylthiophenyl)-2-(2-chlorophenyl)acrylamido)methyl)benzamide;
24. N-(2-Aminophenyl)-4-((3-(4-methylthiophenyl)-2-(2-fluorophenyl)acrylamido)methyl)benzamide;
25. N-(2-Aminophenyl)-4-((3-(4-methylthiophenyl)-2-(4-methylphenyl)acrylamido)methyl)benzamide;
26. N-(2-Aminophenyl)-4-((3-(4-methylthiophenyl)-2-(thiophen-3-yl)acrylamido)methyl)benzamide;
27. N-(2-Aminophenyl)-4-((3-(3,4-dimethoxyphenyl)-2-(4-methoxyphenyl)acrylamido)methyl)benzamide;
28. N-(2-Aminophenyl)-4-((3-(3,4-dimethoxyphenyl)-2-(2-fluorophenyl)acrylamido)methyl)benzamide;
29. N-(2-Aminophenyl)-4-((3-(3,4-dimethoxyphenyl)-2-(4-methylphenyl)acrylamido)methyl)benzamide;
30. N-(2-Aminophenyl)-4-((3-(3,4-dimethoxyphenyl)-2-(2-chlorophenyl)acrylamido)methyl)benzamide;
31. N-(2-Aminophenyl)-4-((3-(3,4-dimethoxyphenyl)-2-phenylacrylamido)methyl)benzamide;
32. N-(2-Aminophenyl)-4-((3-(3,4-dimethoxyphenyl)-2-(3-fluorophenyl)acrylamido)methyl)benzamide;
33. N-(2-Aminophenyl)-4-((3-(4-carbmethoxyphenyl)-2-(3-chlorophenyl)acrylamido)methyl)benzamide;
34. N-(2-Aminophenyl)-4-((3-(4-carbmethoxyphenyl)-2-(2-fluorophenyl)acrylamido)methyl)benzamide;
35. N-(2-Aminophenyl)-4-((3-(4-carbmethoxyphenyl)-2-(4-methoxyphenyl)acrylamido)methyl)benzamide;
36. N-(2-Aminophenyl)-4-((3-(4-carbmethoxyphenyl)-2-(thiophen-2-yl)acrylamido)methyl)benzamide;
37. N-(2-Aminophenyl)-4-((3-(3,4-dimethoxyphenyl)-2-(thiophen-2-yl)acrylamido)methyl)benzamide;
38. N-(2-Aminophenyl)-4-((3-(4-carbmethoxyphenyl)-2-(3,4-difluorophenyl)acrylamido)methyl)benzamide;
39. N-(2-Aminophenyl)-4-((3-(2,4-dimethoxyphenyl)-2-phenylacrylamido)methyl)benzamide;
40. N-(2-Aminophenyl)-4-((2-(3,4-dimethoxyphenyl)-3-phenylacrylamido)methyl)benzamide;
41. N-(2-Aminophenyl)-4-((3-(3,4-dimethoxyphenyl)-2-(pyridin-3-yl)acrylamido)methyl)benzamide;
42. N-(2-Aminophenyl)-4-((3-(3,4-dimethoxyphenyl)-2-(4-methylphenyl)acrylamido))benzamide;
43. N-(2-Aminophenyl)-4-((3-(3,4-difluorophenyl)-2-(4-methoxyphenyl)acrylamido)methyl)benzamide;
44. N-(2-Aminophenyl)-4-((3-(4-fluorophenyl)-2-(4-methoxyphenyl)acrylamido)methyl)benzamide;
45. N-(2-Aminophenyl)-4-((3-(4-fluorophenyl)-2-[benzo[d][1,3-dioxo-5-yl]acrylamido)methyl)benzamide;
46. N-(2-Aminophenyl)-4-((3-(4-methylthiophenyl)-2-(3,4-dimethoxyphenyl)acrylamido)methyl)benzamide;
47. N-(2-Aminophenyl)-4-((3-(4-methylthiophenyl)-2-(3,4-methylenedioxyphenyl)acrylamido)methyl)benzamide;
48. 4-((2-(4-Fluorophenyl)-3-(3,4,5-trimethoxyphenyl)acrylamido)methyl)-N-hydroxybenzamide;
49. 4-((2-(4-Methoxyphenyl)-3-(4-fluorophenyl)acrylamido)methyl)-N-hydroxybenzamide;
50. 4-((2-(4-Trifluoromethyllphenyl)-3-(4-fluorophenyl)acrylamido)methyl)-N-hydroxybenzamide;
51. 4-((2-(Phenyl)-3-(4-fluorophenyl)acrylamido)methyl)-N-hydroxybenzamide;
52. 4-((2-(4-Fluorophenyl)-3-(4-methylthiophenyl)acrylamido)methyl)-N-hydroxybenzamide;
53. 4-((2-(4-Fluorophenyl)-3-(4-methoxyphenyl)acrylamido)methyl)-N-hydroxybenzamide;
54. 4-((2-(4-Fluorophenyl)-3-(2,4,6-trifluorophenyl)acrylamido)methyl)-N-hydroxybenzamide;
55. 4-((2-(Pyridin-3-yl)-3-(4-methylthiophenyl)acrylamido)methyl)-N-hydroxybenzamide;
56. 4-((2-(2-Chlorophenyl)-3-(4-methylthiophenyl)acrylamido)methyl)-N-hydroxybenzamide;
57. 4-((2-(4-Methoxyphenyl)-3-(4-methylthiophenyl)acrylamido)methyl)-N-hydroxybenzamide;
58. 4-((2-(4-Methylphenyl)-3-(4-methylthiophenyl)acrylamido)methyl)-N-hydroxybenzamide;
59. 4-((2-(Thiophen-3-yl)-3-(4-methylthiophenyl)acrylamido)methyl)-N-hydroxybenzamide;
60. 4-((2-(4-Fluorophenyl)-3-(4-fluoro-3-methoxyphenyl)acrylamido)methyl)-N-hydroxybenzamide;
61. 4-((2-(4-Fluorophenyl)-3-(cyclopropyl)acrylamido)methyl)-N-hydroxybenzamide;
62. 4-((2-(4-Methylphenyl)-3-(3,4-dimethoxyphenyl)acrylamido)methyl)-N-hydroxybenzamide;
63. 4-((2-(4-Fluorophenyl)-3-(3,4-dimethoxyphenyl)acrylamido)methyl)-N-hydroxybenzamide;
64. 4-((2-(4-Methoxyphenyl)-3-(3,4-dimethoxyphenyl)acrylamido)methyl)-N-hydroxybenzamide;
65. 4-((2-(4-Methylphenyl)-3-(3,4-dimethoxyphenyl)acrylamido))-N-hydroxybenzamide;
66. 4-((2-Phenyl-3-(3,4-dimethoxyphenyl)acrylamido)methyl)-N-hydroxybenzamide;

67. 4-((2-[Benzo[d]-1,3-dioxo-5-yl]-3-(4-fluorophenyl)acrylamido))-N-hydroxybenzamide;
68. 4-((2-[Benzo[d]-1,3-dioxo-5-yl]-3-(4-fluorophenyl)acrylamido)methyl)-N-hydroxybenzamide;
69. 4-((2-(3,4-Dimethoxyphenyl)-3-(4-methylthiophenyl)acrylamido)methyl)-N-hydroxybenzamide;
70. 4-((2-[Benzo[d]-1,3-dioxo-5-yl]-3-(4-methylthiophenyl)acrylamido)methyl)-N-hydroxybenzamide;
71. 4-((2-(4-Methoxyphenyl)-3-(pyridin-3-yl)acrylamido)methyl)-N-hydroxybenzamide;
72. 4-((2-(4-Fluorophenyl)-3-(pyridin-3-yl)acrylamido)methyl)-N-hydroxybenzamide
73. 4-((2-(4-Methoxyphenyl)-3-(3,4-difluorophenyl)acrylamido)methyl)-N-hydroxybenzamide;
74. 4-((2-Phenyl-3-(4-methylthiophenyl)acrylamido)methyl)-N-hydroxybenzamide;
75. (1E)-N-(4-(3-(Hydroxyamino)-3-oxoprop-1-enyl)benzyl)-2,3-diphenyl acrylamide;
76. (1E)-N-(4-(3-(Hydroxyamino)-3-oxoprop-1-enyl)benzyl)-2-(4-fluorophenyl)-3-(4-methylthiophenyl)acrylamide;
77. (1E)-N-(4-(3-(Hydroxyamino)-3-oxoprop-1-enyl)benzyl)-2-(4-fluorophenyl)-3-(3,4-dimethoxyphenyl)acrylamide;
78. (1E)-N-(4-(3-(Hydroxyamino)-3-oxoprop-1-enyl)benzyl)-2-(2-fluorophenyl)-3-(3,4-dimethoxyphenyl)acrylamide;
79. (1E)-N-(4-(3-(Hydroxyamino)-3-oxoprop-1-enyl)benzyl)-2-(2-phenyl)-3-(4-fluorophenyl)acrylamide;
80. (1E)-N-(4-(3-(Hydroxyamino)-3-oxoprop-1-enyl)benzyl)-2-(2-fluorophenyl)-3-(3,5-dimethoxyphenyl)acrylamide;
81. (1E)-N-(4-(3-(Hydroxyamino)-3-oxoprop-1-enyl)benzyl)-2-(2-fluorophenyl)-3-(3,4,5-trimethoxyphenyl)acrylamide;
82. (1E)-N-(4-(3-(Hydroxyamino)-3-oxoprop-1-enyl)benzyl)-2-(2-fluorophenyl)-3-(4-methoxyphenyl)acrylamide;
83. (2E)-7-(2,3-Diphenylacrylamido)-N-hydroxy heptanamide;
84. 7-(2-(4-Fluorophenyl)-3-(4-methylthiophenyl)acrylamido)-N-hydroxy heptanamide;
85. (2Z)-7-(2,3-Diphenylacrylamido)-N-hydroxy heptanamide;
86. 6-(2-(4-Fluorophenyl)-3-(4-methoxyphenyl)acrylamido)-N-hydroxy hexanamide;
87. 6-(2-(4-Fluorophenyl)-3-(4-methylsulfonylphenyl)acrylamido)-N-hydroxy hexanamide;
88. 6-(2,3-Diphenylacrylamido)-N-hydroxy hexanamide;
89. 6-(2-(4-Fluorophenyl)-3-(2,4,6-trifluorophenyl)acrylamido)-N-hydroxy hexanamide;
90. 6-(2-(Thiophen-3-yl)-3-(4-methylthiophenyl)acrylamido)-N-hydroxy hexanamide;
91. 6-(2-(4-Fluorophenyl)-3-(4-fluoro-3-methoxyphenyl)acrylamido)-N-hydroxy hexanamide;
92. 6-(2-(4-Methoxyphenyl)-3-(4-methylthiophenyl)acrylamido)-N-hydroxy hexanamide;
93. 6-(2-(4-Fluorophenyl)-3-(cyclopropyl)acrylamido)-N-hydroxy hexanamide;
94. 6-(2-(2-Fluorophenyl)-3-(4-methylthiophenyl)acrylamido)-N-hydroxy hexanamide;
95. 6-(2-(2-Chlorophenyl)-3-(4-methylthiophenyl)acrylamido)-N-hydroxy hexanamide;
96. 6-(2-(4-Methylphenyl)-3-(4-methylthiophenyl)acrylamido)-N-hydroxy hexanamide;
97. N-(2-Aminophenyl)-6-(2-(4-fluorophenyl)-3-(4-methylsulfonyll phenyl)acrylamido)hexanamide;
98. N-(2-Aminophenyl)-6-(2-(4-fluorophenyl)-3-(4-methylthiophenyl)acrylamido)hexanamide;
99. 6-(3-(2-(4-Fluorophenyl)-3-(4-methylthiophenyl)acryloyl)ureido)-N-hydroxy hexanamide;
100. (2-(4-Fluorophenyl)-3-(3,4-difluorophenyl)acryloyl)ureido)-N-hydroxy hexanamide;
101. 6-(3-(2,3-Diphenyl)acryloyl)ureido)-N-hydroxy hexanamide;
102. 3-(3,4-Dimethoxyphenyl)-2-(4-methoxyphenyl)allyl-4-(2-aminophenylcabamoyl)benzylcarbamate; and
103. 3-(3,4-Dimethoxyphenyl)-2-(4-methylphenyl)allyl-4-(2-aminophenylcabamoyl)benzylcarbamate.

Also provided herein is a process as shown in the following scheme, for the preparation of compounds of the formula (I), wherein all the groups are as defined earlier.

a. Condensing the compound of formula (1a) and the compound of formula (1b) with Ac$_2$O and an organic base to yield a compound of formula (1c), wherein R and R$^1$, are as defined earlier.

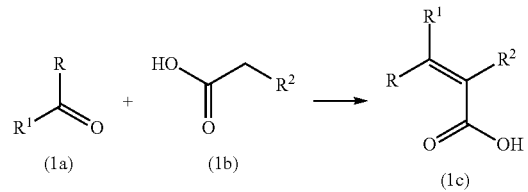

b. 1) Reacting the compound of the formula (1c) with an acid activating agent such as EDCI, HOBt and the like in the presence 2a or 2b to yield 1d or 1e wherein R, R$^1$, R$^2$, o and q are as defined earlier.
   2) The compound of formula Ic was converted to the corresponding amide using acid chloride and ammonia. The amide was again treated with oxalyl chloride and the like to generate 2c which on treating with 2b to yield 1f.
   3) Reducing is with lithium aluminium hydride and the like gave 2d. The compound 2d was treated with carbonylating agents such as carbonyl diimidazole or phosgene or the like in the presence of base and 2a gave 1 g.

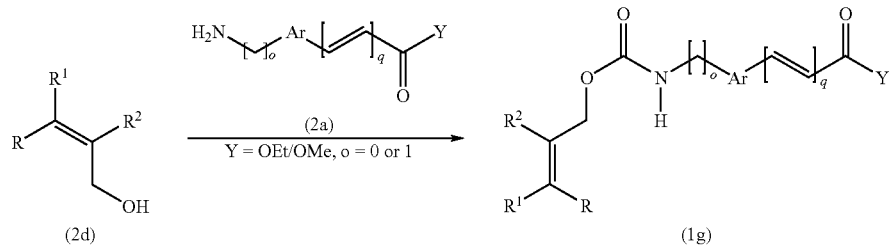

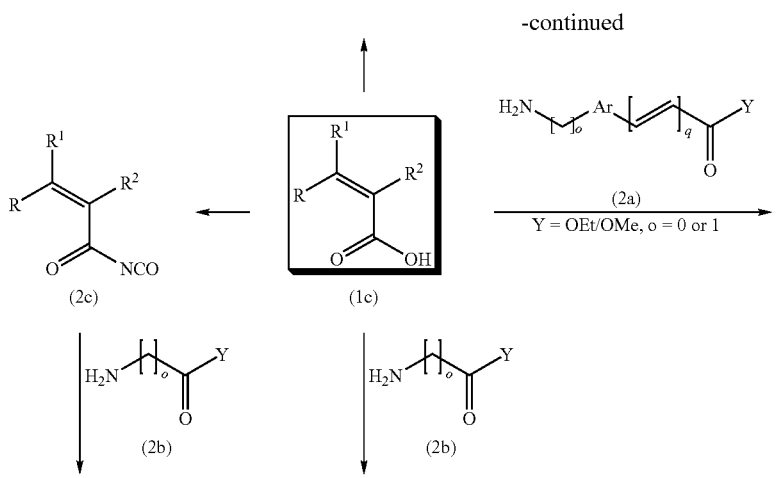
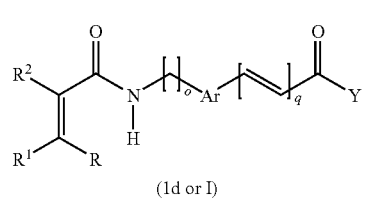

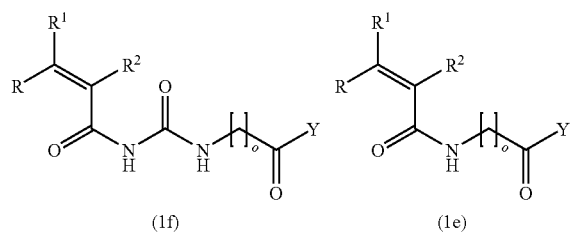

c. Hydrolyzing the compound of formula (1d-1g) with a base to give the acid, further the acid is coupled with the activating agent such as EDCI, HOBt and the like in the presence of the respective amine $R^3NH_2$ to yield the compound of the general formula (1) wherein R, $R^1$, $R^2$, $R^3$, o and q are as defined earlier or reacting compound of formula (1d-1g) with $R^3NH_2$ and inorganic base to yield compound of formula (1)

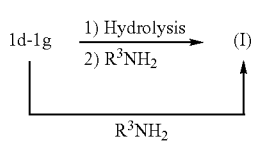

Also provided herein is a process for the preparation of compound of formula (I) from a compound of formula (2a) or (2b) on treatment with the compound of formula (II) or its activated form

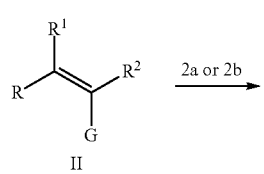

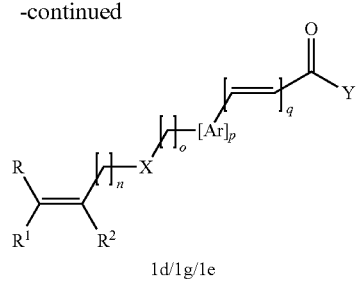

wherein G is —$CH_2OH$, —COOH and —CO—NCO and R, $R^1$ and $R^2$ are as defined earlier.

In any of the above-mentioned reactions, any reactive group in the substrate molecule may be protected according to the conventional chemical practice. Suitable protecting groups in any of the above-mentioned reactions are those used conventionally in the art. The methods of formation and removal of such protecting groups are those conventional methods appropriate to the molecule being protected. Suitable solvents for the reactions can be ether, THF, methanol, t-butanol, dioxane, isopropanol, ethanol, DMF, $CH_3CN$ and the like and the mixtures thereof. The organic bases used for the reaction can be pyridine, triethylamine, pyrrolidine, N,N-dimethylamino pyridine, diisopropyl ethylamine and the like and the mixtures thereof and inorganic bases such as NaOH, KOH, $K_2CO_3$, $Cs_2CO_3$ and the like can be used.

The pharmaceutically acceptable salts can be prepared by reacting the compound of formula (I) with 1 to 4 equivalents of a base such as sodium hydroxide, sodium methoxide, sodium hydride, potassium t-butoxide, and calcium hydroxide, magnesium hydroxide and the like, in solvents like ether, THF, methanol, t-butanol, dioxane, isopropanol, ethanol and the like. Mixtures of solvents may be used. Organic bases like lysine, arginine, diethanolamine, choline, guanidine and their derivatives and the like may also be used. Alternatively, acid addition salts can be prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The invention is explained in details in the examples given below which are provided by the way of illustration only and therefore should not be construed to limit the scope of the invention.

EXAMPLE 1

Synthesis of N-(2-aminophenyl)-4-((3-(3,4-difluorophenyl)-2-(4-fluorophenyl)acrylamido)methyl)benzamide

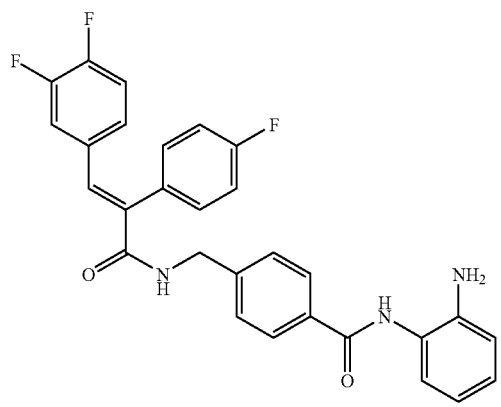 [SMILES: Nc1ccccc1NC(=O)c1ccc(CNC(=O)/C(=C/c2ccc(F)c(F)c2)c2ccc(F)cc2)cc1]

Step 1

Preparation of 3-(3,4-difluorophenyl)-2-(4-fluorophenyl)acrylic acid

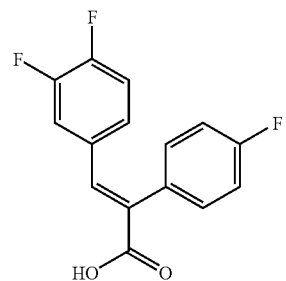 [SMILES: O=C(O)/C(=C/c1ccc(F)c(F)c1)c1ccc(F)cc1]

A mixture of 4-fluorophenylacetic acid (2 g, 13 mmol), 3,4-difluorobenzaldehyde (2.5 g, 13 mmol), $Ac_2O$ (10 mL) and diisopropylethylamine (2.9 mL) was stirred at room temperature for 12 hours. Upon completion, as monitored by TLC using DCM:MeOH (9:1) as the eluent, 10 mL 10% aqueous HCl was added to the reaction mixture, the precipitate formed was filtered and dissolved in $CH_2Cl_2$ (100 mL). The organic layer was washed with 10% aqueous NaOH (3×50 mL) and the basic aqueous solution was acidified with 10% aqueous HCl to pH 3. The precipitate formed was filtered, washed with water (100 mL) and dried to get the product (4.4 g, 41.5% yield).

Step 2

Preparation of 4-((t-butoxycarbonylamino)methyl)benzoic acid

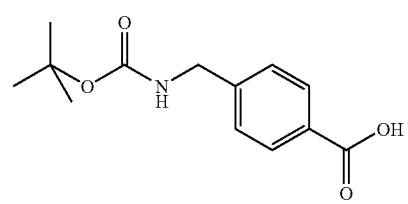 [SMILES: CC(C)(C)OC(=O)NCc1ccc(C(=O)O)cc1]

To a solution of 4-aminomethylbenzoic acid (5 g, 33 mmol) in water maintained at 0° C., was added 5% aqueous NaOH solution (100 mL), followed by dropwise addition of Boc anhydride (15 mL, 66 mmol) in n-butanol (10 mL). Subsequently, the reaction mixture was stirred at room temperature for 3 hours. Upon completion, as monitored by TLC using DCM:MeOH (9:1) as the eluent, the reaction mixture was poured in ice water, acidified with citric acid up to pH 4. On standing at room temperature for 10 minutes the precipitate formed was filtered, washed with water (100 mL) and dried to give the Boc protected product (6.5 g, 46.5% yield).

Step 3

Preparation of t-butyl-4-(2-aminophenylcarbamoyl)benzylcarbamate

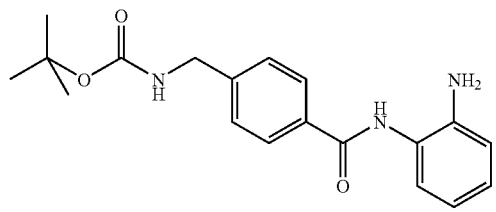 [SMILES: CC(C)(C)OC(=O)NCc1ccc(C(=O)Nc2ccccc2N)cc1]

To a suspension of 4-((t-butoxycarbonylamino)methyl) benzoic acid (6.08 g, 24.2 mmol) in DMF was added o-phenylene diamine (2.9 g, 29 mmol), EDCI (9.3 g, 48.4 mmol) and HOBt (3.8 g, 24.2 mmol). TEA (11.8 mL, 84.8 mmol) was added drop wise with constant stirring to the above reaction mixture, which was stirred at room temperature overnight. Subsequently, the reaction mixture was evaporated to half its volume; the resulting solution was dissolved in ethyl acetate, washed successively with saturated $NaHCO_3$ (3×50 mL) and brine solution (3×50 mL). The organic layer was dried over $Na_2SO_4$ and concentrated to give the pure compound (4.6 g, 56% yield).

Step 4

Preparation of 4-(aminomethyl)-N-(2-aminophenyl)benzamide

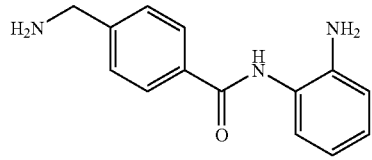 [SMILES: NCc1ccc(C(=O)Nc2ccccc2N)cc1]

To a solution of t-butyl-4-(2-aminophenylcarbamoyl)benzylcarbamate (4.6 g, 13.8 mmol) in methanol 5 mL was added methanolic HCl (5 mL) at 0° C., dropwise and the reaction mixture was stirred at room temperature for 2 hours. Upon completion, as monitored by TLC using DCM:MeOH (9:1) as the eluent, the reaction mixture was evaporated to dryness, another portion of MeOH was added and the solution was again evaporated to dryness to give the pure product as the hydrochloride salt. (4.5 g, 70.8% yield).

Step 5

Preparation of N-(2-aminophenyl)-4-((3-(3,4-difluorophenyl)-2-(4-fluorophenyl)acrylamido)methyl) benzamide

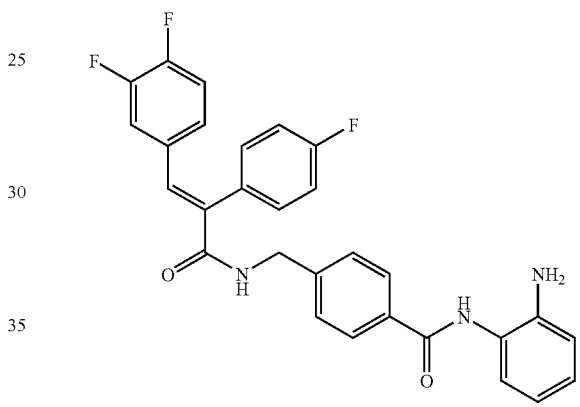

To a solution of 3-(3,4-difluorophenyl)-2-(4-fluorophenyl) acrylic acid (0.5 g, 1.7 mmol) in DMF (5 mL) was added TEA (0.75 mL, 5.4 mmol), EDCI (0.68 g, 3.5 mmol), HOBt (0.25 g, 1.8 mmol) followed by the 4-(aminomethyl)-N-(2-aminophenyl)benzamide (0.52 g, 1.9 mmol). The reaction mixture was stirred at room temperature for 12 hours. Subsequently it was concentrated under reduced pressure to half the volume and the resulted solution was poured into water. Upon standing a white precipitate formed, was filtered, washed with water followed by ether gave the pure product (0.3 g, 30% yield). $^1$H NMR (400 MHz, DMSO-$d_6$) δ (ppm): 4.41 (2H, d, $CH_2$), 4.88 (2H, s, $NH_2$), 6.59 (1H, t, Ar—H), 6.77 (1H, d, Ar—H), 6.88 (1H, s, Ar—H), 6.96 (2H, m, Ar—H), 7.16 (1H, d, Ar—H), 7.24-7.38 (7H, m, Ar—H), 7.47 (1H, s, =CH), 7.92 (2H, d, Ar—H), 8.14 (1H, t, NH), 9.61 (1H, s, NH). MS m/z: 502.1 ($M^+$+1).

The following compounds were prepared according to the above procedure.

| S. No | Structure | Analytical Data |
|---|---|---|
| 2 | 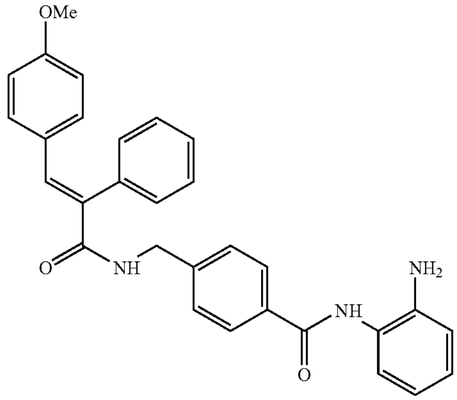 [SMILES: COc1ccc(/C=C(/C(=O)NCc2ccc(C(=O)Nc3ccccc3N)cc2)c2ccccc2)cc1] | $^1$H NMR (DMSO-d$_6$) δ (ppm): 3.69 (3H, s, OCH$_3$), 4.41 (2H, d, —CH$_2$,), 4.88 (2H, s, NH$_2$), 6.57 (1H, t, Ar—H), 6.72-6.79 (3H, m, Ar—H), 6.91-6.93 (3H, m, Ar—H), 7.21-7.23 (3H, m, Ar—H), 7.36-7.38 (2H, m, Ar—H), 7.43-7.46 (4H, m, Ar—H), 7.86-7.93 (3H, m, Ar—H and NH), 9.60 (1H, s, NH); 478.2 MS m/z: 478.2 (M$^+$ + 1). |
| 3 | 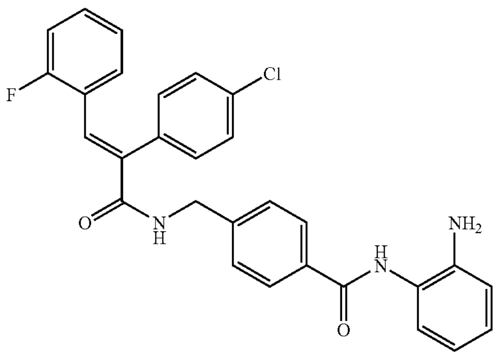 [SMILES: Nc1ccccc1NC(=O)c1ccc(CNC(=O)/C(=C/c2ccccc2F)c2ccc(Cl)cc2)cc1] | $^1$H NMR (DMSO-d$_6$) δ (ppm): 4.41 (2H, d, —CH$_2$), 4.89 (2H, s, NH$_2$), 6.59 (1H, m, Ar—H), 6.77 (2H, m, Ar—H), 6.95-6.99 (2H, m, Ar—H), 7.15-7.22 (4H, m, Ar—H), 7.28 (1H, m, Ar—H), 7.38-7.46 (4H, m, Ar—H), 7.53 (1H, s, =CH), 7.93 (2H, d, Ar—H), 8.31 (1H, t, NH), 9.62 (1H, s, NH); MS m/z: 500.1 (M$^+$ + 1). |
| 4 | 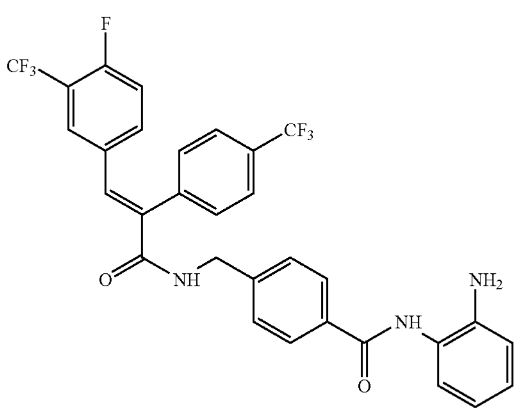 [SMILES: Nc1ccccc1NC(=O)c1ccc(CNC(=O)/C(=C/c2ccc(F)c(C(F)(F)F)c2)c2ccc(C(F)(F)F)cc2)cc1] | $^1$H NMR (DMSO-d$_6$) δ (ppm): 4.41 (2H, d, CH$_2$), 4.89 (2H, s, NH$_2$), 6.60 (1H, m, Ar—H), 6.80 (1H, m, Ar—H), 6.96 (1H, m, Ar—H), 7.16 (2H, m, Ar—H), 7.39-7.48 (6H, m, Ar—H), 7.63 (1H, s, =CH$_2$), 7.81 (2H, d, Ar—H), 7.93 (2H, d, Ar—H), 8.34 (1H, t, NH), 9.62 (1H, s, NH); MS m/z: 602.1 (M$^+$ + 1). |
| 5 | 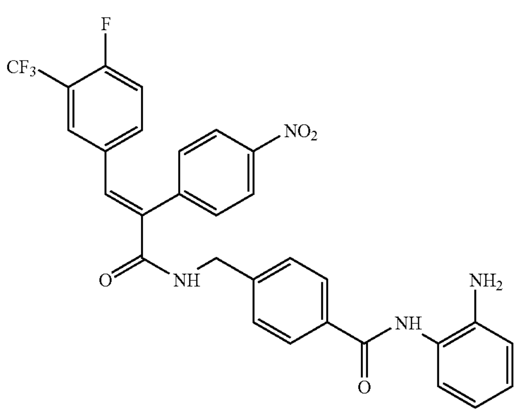 [SMILES: Nc1ccccc1NC(=O)c1ccc(CNC(=O)/C(=C/c2ccc(F)c(C(F)(F)F)c2)c2ccc([N+](=O)[O-])cc2)cc1] | $^1$H NMR (DMSO-d$_6$) δ (ppm): 4.43 (2H, d, —CH$_2$), 4.88 (2H, s, —NH$_2$), 6.59 (1H, m Ar—H), 6.78 (1H, m, Ar—H), 6.97 (1H, m Ar—H), 7.16 (1H, m Ar—H), 7.33-7.55 (7H, m Ar—H), 7.66 (1H, s, =CH), 7.94 (2H, d, Ar—H), 8.29 (2H, d, Ar—H), 8.40 (1H, t, NH), 9.62 (1H, s, NH); MS m/z: 579.1 (M$^+$ + 1). |

| S. No | Structure | Analytical Data |
|---|---|---|
| 6 | 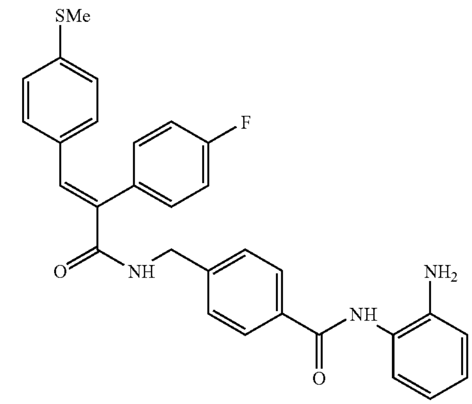 | ¹H NMR (DMSO-d₆) δ (ppm): 2.41 (3H, s), 4.40 (2H, d), 4.89 (2H, s), 6.60 (1H, m, Ar—H), 6.77 (1H, m, Ar—H), 6.94 (3H, m, Ar—H), 7.08 (2H, m, Ar—H), 7.16 (1H, m, Ar—H), 7.26-7.28 (4H, m, Ar—H), 7.37 (2H, m, Ar—H), 7.46 (1H, s, =CH), 7.92 (2H, m, Ar—H), 8.05 (1H, t, NH), 9.61 (1H, s, NH); MS m/z: 512.1 (M⁺ + 1). |
| 7 | 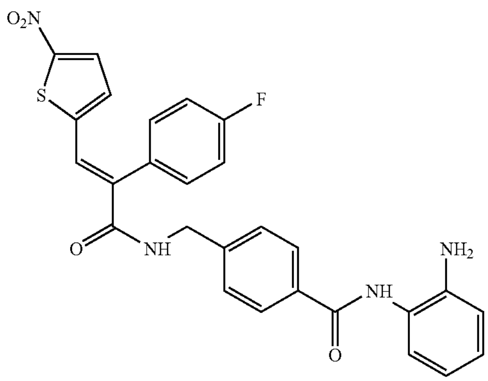 [SMILES: Nc1ccccc1NC(=O)c1ccc(CNC(=O)/C(=C/c2ccc([N+](=O)[O-])s2)c2ccc(F)cc2)cc1] | ¹H NMR (DMSO-d₆) δ (ppm): 4.40 (2H, d, —CH₂), 4.88 (2H, s, —NH₂), 6.59 (1H, t, Ar—H), 6.77 (1H, d, Ar—H), 6.96 (1H, t, Ar—H), 7.15 (1H, d, Ar—H), 7.34-7.49 (6H, m, Ar—H), 7.88-8.08 (6H, m, Ar—H and NH), 9.61 (1H, s, —NH); MS m/z: 517.1 (M⁺ + 1). |
| 8 | 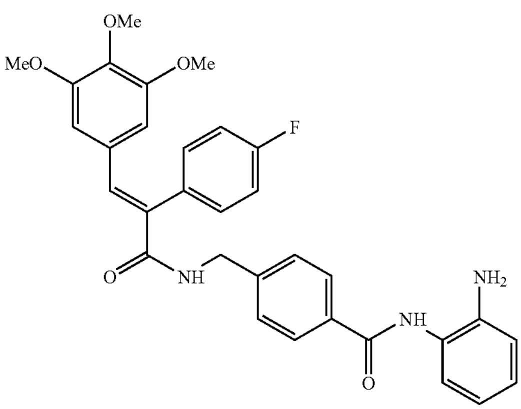 [SMILES: COc1cc(/C=C(/C(=O)NCc2ccc(C(=O)Nc3ccccc3N)cc2)c2ccc(F)cc2)cc(OC)c1OC] | ¹H NMR (DMSO-d₆) δ (ppm): 3.49 (6H, s, —OCH₃), 3.61 (3H, s, —CH₃), 4.41 (2H, d, —CH₂,), 4.96 (2H, s, —NH₂), 6.33 (2H, s, Ar—H), 6.61 (1H, t, Ar—H), 6.78 (1H, d, Ar—H), 6.97 (1H, t, Ar—H), 7.15 (1H, d, Ar—H), 7.30-7.38 (6H, m, Ar—H), 7.50 (1H, s, =CH), 7.91-8.01 (3H, m, Ar—H and NH), 9.63 (1H, s, —NH); MS m/z: 556.2 (M⁺ + 1). |
| 9 | 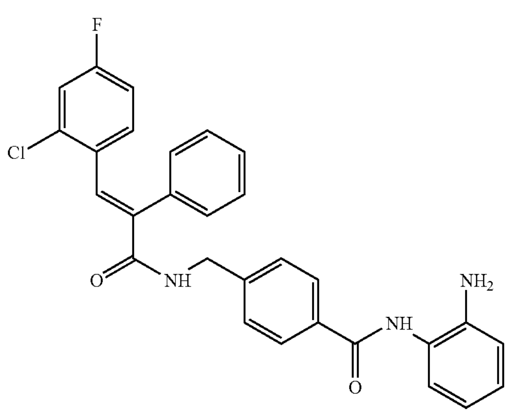 [SMILES: Nc1ccccc1NC(=O)c1ccc(CNC(=O)/C(=C/c2ccc(F)cc2Cl)c2ccccc2)cc1] | ¹H NMR (DMSO-d₆) δ (ppm): 4.43 (2H, d, —CH₂,), 4.96 (2H, s, —NH₂), 6.62 (1H, t, Ar—H), 6.76-6.81 (2H, m, Ar—H), 6.95-6.98 (2H, m, Ar—H), 6.96-6.97 (2H, d, Ar—H), 7.13 (1H, d, Ar—H), 7.34-7.50 (7H, m, Ar—H), 7.93-7.95 (2H, d, Ar—H), 8.30 (1H, t, —NH), 9.66 (1H, s, —NH); MS m/z: 500.1 (M⁺ + 1). |

| S. No | Structure | Analytical Data |
|---|---|---|
| 10 | (4-fluorophenyl, phenyl acrylamide linked to 4-(N-(2-aminophenyl)carbamoyl)benzyl) | $^1$H NMR (DMSO-d$_6$) δ (ppm): 4.41 (2H, d, —CH$_2$—), 4.89 (2H, s, —NH$_2$), 6.59 (1H, t, Ar—H), 6.76-6.78 (1H, d, Ar—H), 6.96-7.04 (4H, m, Ar—H), 7.15-7.23 (3H, m, Ar—H), 7.37-7.47 (7H, m, Ar—H), 7.91-7.93 (2H, d, Ar—H), 8.04 (1H, t, —NH), 9.62 (1H, s, —NH); MS m/z: 466.1 (M$^+$ + 1). |
| 11 | (4-methoxyphenyl, 4-fluorophenyl acrylamide linked to 4-(N-(2-aminophenyl)carbamoyl)benzyl) | $^1$H NMR (DMSO-d$_6$) δ (ppm): 3.70 (3H, s, OCH$_3$), 4.40 (2H, d, —CH$_2$—), 4.88 (2H, s, NH$_2$), 6.59 (1H, t, Ar—H), 6.76-6.78 (3H, m, Ar—H), 6.92-6.96 (3H, m, Ar—H), 7.15-7.17 (1H, m, Ar—H), 7.25-7.37 (6H, m, Ar—H), 7.48 (1H, s, =CH), 7.91-7.94 (3H, m, Ar—H), 9.61 (1H, s, NH); MS m/z: 496.2 (M$^+$ + 1). |
| 12 | (phenyl, phenyl acrylamide linked to 4-(N-(2-aminophenyl)carbamoyl)benzyl) | $^1$H NMR (DMSO-d$_6$) δ (ppm): 4.41-4.43 (2H, d, —CH$_2$—), 4.89 (2H, s, —NH$_2$), 6.59 (1H, t, Ar—H), 6.76-6.78 (1H, d, Ar—H), 6.94-7.00 (3H, m, Ar—H), 7.15-7.23 (7H, m, Ar—H), 7.37-7.47 (5H, m, Ar—H), 7.92-7.94 (2H, d, Ar—H), 8.05 (1H, t, —NH), 9.61 (1H, s, —NH); MS m/z: 448.1 (M$^+$ + 1). |
| 13 | (2,4,6-trifluorophenyl, 4-fluorophenyl acrylamide linked to 4-(N-(2-aminophenyl)carbamoyl)benzyl) | $^1$H NMR (DMSO-d$_6$) δ (ppm): 4.43 (2H, d, —CH$_2$—), 4.91 (2H, s, —NH$_2$), 6.60 (1H, t, Ar—H), 6.78 (1H, d, Ar—H), 6.97 (1H, t, Ar—H), 7.09 (1H, s, —Ar—H), 7.13-7.24 (7H, m, Ar—H), 7.41 (2H, d, Ar—H), 7.94 (2H, d, Ar—H), 8.55 (1H, s, —NH), 9.63 (1H, s, —NH) MS m/z: 520.1 (M$^+$ + 1). |

| S. No | Structure | Analytical Data |
|---|---|---|
| 14 | 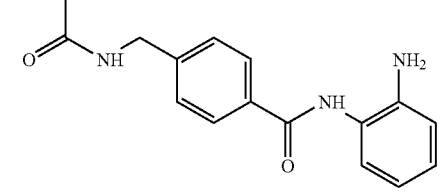 | $^1$H NMR (DMSO-d$_6$) δ (ppm): 0.62 (2H, m, CH$_2$), 0.81-0.82 (2H, m, CH$_2$), 1.27 (1H, m, CH), 4.02 (2H, d, —CH$_2$), 4.34 (2H, s, —NH$_2$), 6.04 (1H, d, Ar—H), 6.60 (1H, t, Ar—H), 6.77 (1H, t, Ar—H), 6.95 (1H, d, —Ar—H), 6.97 (1H, t, Ar—H) 7.16 (1H, d, Ar—H), 7.23-7.35 (6H, m, Ar—H), 7.88-7.91 (3H, m, Ar—H), 9.60 (1H, s, —NH) MS m/z: 430.1 (M$^+$ + 1). |
| 15 | 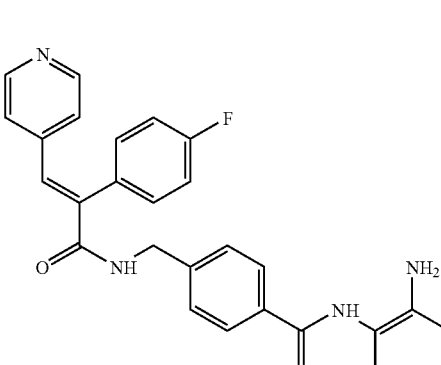 | $^1$H NMR (DMSO-d$_6$) δ (ppm): 4.42 (2H, d, —CH$_2$), 4.88 (2H, s, —NH$_2$), 6.59 (1H, t, Ar—H), 6.78 (1H, d, Ar—H), 6.93-6.98 (3H, m, Ar—H), 7.16 (1H, d, —Ar—H), 7.26 (4H, d, Ar—H) 7.38-7.42 (3H, m, Ar—H), 7.93 (2H, d, Ar—H), 8.33-8.41 (3H, m, Ar—H&NH), 9.62 (1H, s, —NH) MS m/z: 467.1 (M$^+$ + 1). |
| 16 | 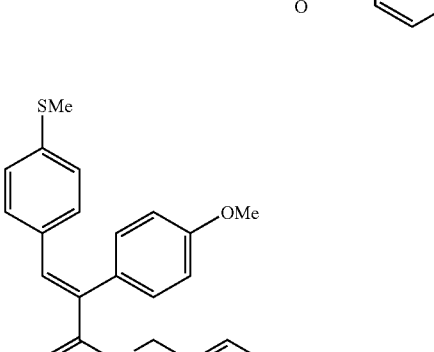 | $^1$H NMR (DMSO-d$_6$) δ (ppm): 2.41 (3H, s, —SCH$_3$), 3.79 (3H, s, —OCH$_3$), 4.39 (2H, d, —CH$_2$), 4.88 (2H, s, —NH$_2$), 6.60 (1H, t, —ArH), 6.77 (1H, d, —ArH), 6.94-7.17 (8H, m, —ArH), 7.36-7.38 (2H, m, —ArH), 7.41 (1H, s, =CH), 7.89-7.93 (3H, m, —ArH & —NH), 9.61 (1H, s, —NH). MS m/z: 524.2 (M$^+$ + 1). |
| 17 | 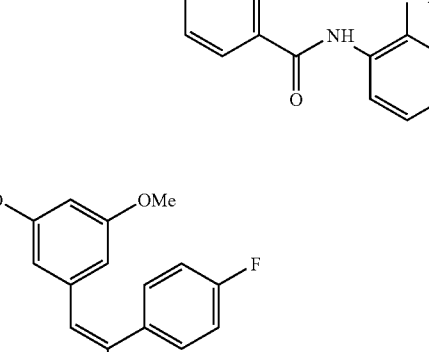 | $^1$H NMR (DMSO-d$_6$) δ (ppm): 3.53 (6H, s-OCH$_3$), 4.40 (2H, d, —CH$_2$), 4.89 (2H, s, —NH$_2$), 6.18 (2H, d, —ArH), 6.35 (1H, t, —ArH), 6.60 (1H, t, —ArH), 6.77 (1H, d, —ArH), 6.96 (1H, t, —ArH), 7.16 (1H, t, —ArH), 7.28-7.29 (4H, m, —ArH), 7.37 (2H, d, —ArH), 7.44 (1H, s, =CH), 7.92 (2H, d —ArH), 8.08-8.11 (1H, t, —NH), 9.61 (1H, s, —NH). MS m/z: 526.2 (M$^+$ + 1). |

| S. No | Structure | Analytical Data |
|---|---|---|
| 18 | 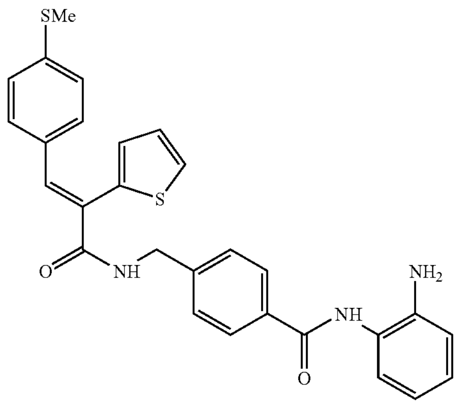 [SMILES: CSc1ccc(/C=C(/C(=O)NCc2ccc(C(=O)Nc3ccccc3N)cc2)c2cccs2)cc1] | $^1$H NMR (DMSO-d$_6$) δ (ppm): 2.44 (3H, s, —SCH$_3$), 4.43 (2H, d, —CH$_2$), 4.89 (2H, s, —NH$_2$), 6.58 (1H, t, —ArH), 6.77 (1H, d, —ArH), 6.96 (1H, t, —ArH), 7.05 (3H, m, —ArH), 7.11-7.15 (4H, m, —ArH), 7.39 (2H, d, —ArH), 7.51 (1H, s, =CH), 7.67 (1H, m, —ArH), 7.93 (2H, d, —ArH), 8.22 (1H, t, —NH), 9.62 (1H, s, —NH). MS m/z: 500.1 (M$^+$ + 1). |
| 19 | 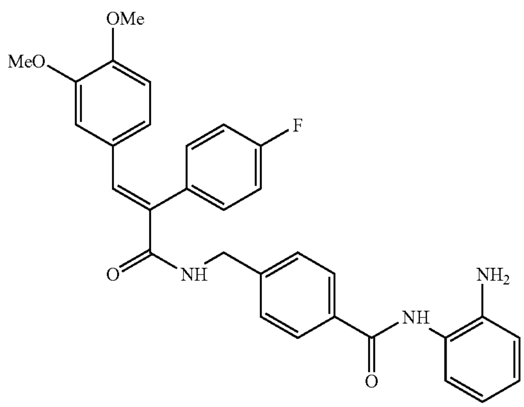 [SMILES: COc1ccc(/C=C(/C(=O)NCc2ccc(C(=O)Nc3ccccc3N)cc2)c2ccc(F)cc2)cc1OC] | $^1$H NMR (DMSO-d$_6$) δ (ppm): 3.43 (3H, s-OCH$_3$), 3.70 (3H, s, —OCH$_3$), 4.40 (2H, d, —CH$_2$), 4.88 (2H, s, —NH$_2$), 6.43 (1H, s, —ArH), 6.60 (1H, t, —ArH), 6.72 (1H, d, —ArH), 6.78 (1H, m, —ArH), 6.84 (1H, d, -ArH), 6.97 (1H, t, —ArH), 7.15 (1H, d —ArH), 7.28-7.31 (4H, m, —ArH), 7.37 (2H, m, —ArH), 7.49 (1H, s, =CH), 7.91-7.95 (3H, m, —ArH & —NH), 9.62 (1H, s, —NH). MS m/z: 526.2 (M$^+$ + 1). |
| 20 | 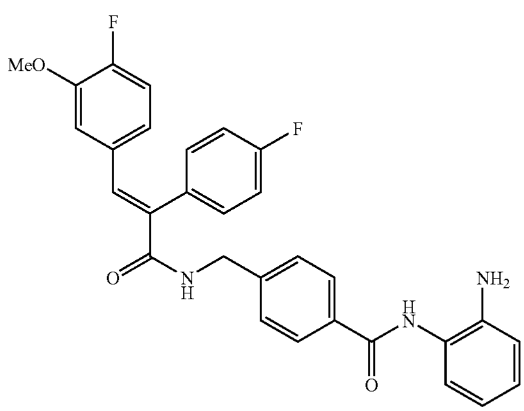 [SMILES: COc1cc(/C=C(/C(=O)NCc2ccc(C(=O)Nc3ccccc3N)cc2)c2ccc(F)cc2)ccc1F] | $^1$H NMR (DMSO-d$_6$) δ (ppm): 3.51 (3H, s-OCH$_3$), 4.41 (2H, d, —CH$_2$), 4.88 (2H, s, —NH$_2$), 6.60 (1H, t, —ArH), 6.67-6.71 (2H, m, —ArH), 6.78 (1H, d, —ArH), 6.97 (1H, t, —ArH), 7.08 (1H, m, —ArH), 7.16 (1H, d, —ArH) 7.28-7.31 (4H, m, —ArH), 7.38 (2H, d, —ArH), 7.50 (1H, s, =CH), 7.92 (2H, d, —ArH), 8.09 (1H, t, —NH), 9.63 (1H, s, —NH). MS m/z: 514.2 (M$^+$ + 1). |
| 21 | 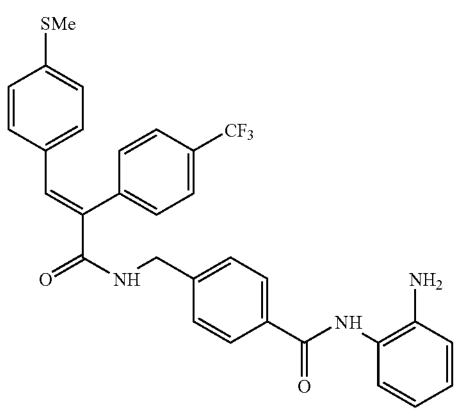 [SMILES: CSc1ccc(/C=C(/C(=O)NCc2ccc(C(=O)Nc3ccccc3N)cc2)c2ccc(C(F)(F)F)cc2)cc1] | $^1$H NMR (DMSO-d$_6$) δ (ppm): 2.41 (3H, s, —SCH$_3$), 4.41 (2H, d, —CH$_2$), 4.89 (2H, s, —NH$_2$), 6.60 (1H, t, —ArH), 6.78 (1H, t, —ArH), 6.91-6.96 (3H, m, —ArH), 7.08 (2H, m, —ArH), 7.16 (1H, m, —ArH), 7.38-7.46 (4H, m, —ArH) 7.52 (1H, s, =CH), 7.79 (2H, d, —ArH), 7.93 (2H, d, —ArH), 8.22 (1H, t, —NH), 9.62 (1H, s, —NH). MS m/z: 562.1 (M$^+$ + 1). |

| S. No | Structure | Analytical Data |
|---|---|---|
| 22 | (quinoline-substituted cinnamamide with 4-fluorophenyl group, N-benzyl amide linked to 2-aminoanilide) | $^1$H NMR (DMSO-d$_6$) δ (ppm): 4.50 (2H, d, —CH$_2$), 4.90 (2H, s, —NH$_2$), 6.71 (1H, t, Ar—H), 6.77-6.79 (1H, d, Ar—H), 6.94-6.95 (2H, m, Ar—H), 7.05-7.09 (2H, m, Ar—H), 7.14-7.18 (3H, m, Ar—H), 7.38-7.42 (2H, m, Ar—H), 7.62 (1H, t, Ar—H), 7.78 (1H, t, Ar—H), 7.87 (1H, s, =CH), 7.96-8.00 (3H, m, Ar—H), 8.17 (1H, d, Ar—H), 8.63 (1H, d, Ar—H), 8.67 (1H, t, —NH), 9.63 (1H, s, —NH), MS m/z: 517.2 (M$^+$ + 1). |
| 23 | (4-SMe-phenyl and 2-chlorophenyl cinnamamide, N-benzyl-2-aminoanilide) | $^1$H NMR (DMSO-d$_6$) δ (ppm): 2.41 (3H, s, —CH$_3$), 4.41 (2H, d, —CH$_2$), 4.89 (2H, s, —NH$_2$), 6.58-6.61 (1H, t, —ArH), 6.76-6.77 (1H, d, —ArH), 6.87-6.89 (2H, d, —ArH), 6.94-6.99 (1H, m, —ArH), 7.06-7.08 (2H, d, —ArH), 7.15-7.17 (1H, m, Ar—H), 7.23-7.25 (1H, m, —ArH), 7.37-7.40 (3H, t, —ArH & =CH), 7.45-7.50 (1H, m, —ArH), 7.60-7.62 (2H, t, —ArH), 7.91-7.93 (2H, d, —ArH), 8.06-8.08 (1H, t, —NH), 9.62 (1H, s, —NH). MS m/z: 529.1 (M$^+$ + 1). |
| 24 | (4-SMe-phenyl and 2-fluorophenyl cinnamamide, N-benzyl-2-aminoanilide) | $^1$H NMR (DMSO-d$_6$) δ (ppm): 2.42 (3H, s, —SCH$_3$), 4.41-4.42 (2H, d, —CH$_2$), 4.89 (2H, s, —NH$_2$), 6.59 (1H, s, =CH), 6.77-6.79 (1H, d, —ArH), 6.94-6.96 (3H, t, —ArH), 7.07-7.09 (2H, d, —ArH), 7.15-7.17 (1H, t, —ArH), 7.23-7.25 (2H, d, —ArH), 7.27-7.30 (2H, d, —ArH) 7.37-7.39 (1H, m, —ArH), 7.48 (1H, s, —NH), 7.59 (1H, s, —ArH), 7.92-7.94 (2H, d, —ArH), 8.25 (1H, s, —ArH), 9.62 (1H, s, —NH). MS m/z: 512.6 (M$^+$ + 1). |
| 25 | (4-SMe-phenyl and 4-methylphenyl cinnamamide, N-benzyl-2-aminoanilide) | $^1$H NMR (DMSO-d$_6$) δ (ppm): 2.36 (3H, s, —CH$_3$), 2.41 (3H, s, —SCH$_3$), 4.39-4.40 (2H, d, —CH$_2$), 4.89 (2H, s, —NH$_2$), 6.59 (1H, s, =CH), 6.77-6.79 (1H, d, —ArH), 6.93-6.96 (3H, t, —ArH), 7.04-7.06 (4H, d, —ArH), 7.10-7.15 (1H, t, —ArH), 7.25-7.27 (2H, d, —ArH), 7.36-7.42 (3H, d, —ArH), 7.89-7.93 (3H, m, —ArH), 9.62 (1H, s, —NH). MS m/z: 508.3 (M$^+$ + 1). |

| S. No | Structure | Analytical Data |
|---|---|---|
| 26 | 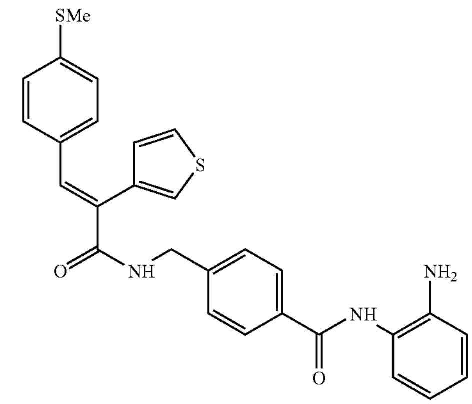 [SMILES: CSc1ccc(/C=C(/C(=O)NCc2ccc(C(=O)Nc3ccccc3N)cc2)c2ccsc2)cc1] | $^1$H NMR (DMSO-d$_6$) δ (ppm): 2.43 (3H, s, —SCH$_3$), 4.41-4.42 (2H, d, —CH$_2$), 4.89 (2H, s, —NH$_2$), 6.59 (1H, s, —ArH), 6.76-6.78 (1H, d, —ArH), 6.93-6.98 (3H, m, —ArH), 7.08-7.10 (2H, d, —ArH), 7.15-7.17 (1H, d, —ArH), 7.37-7.39 (2H, d, —ArH), 7.45 (2H, s, —ArH), 7.67 (1H, s, =CH), 7.91-7.93 (2H, d, —ArH), 7.97-8.00 (1H, d, —ArH), 8.49 (1H, t, —NH), 9.62 (1H, s, —NH). MS m/z: 499.9 (M$^+$ + 1). |
| 27 | 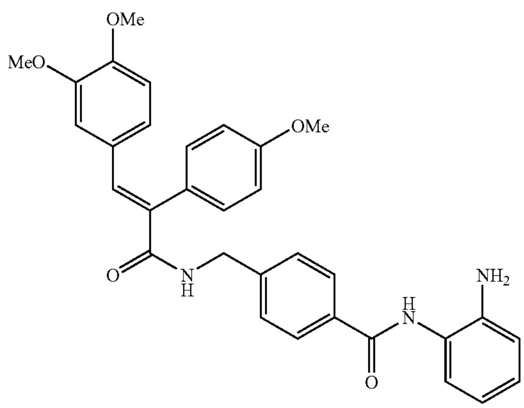 [SMILES: COc1ccc(/C(=C\c2ccc(OC)c(OC)c2)C(=O)NCc2ccc(C(=O)Nc3ccccc3N)cc2)cc1] | $^1$H NMR (DMSO-d$_6$) δ (ppm): 3.34 (3H, s, —OCH$_3$), 3.70 (3H, s, —OCH$_3$), 3.84 (3H, s, —OCH$_3$), 4.39-4.40 (2H, d, —CH$_2$), 4.89 (2H, s, —NH$_2$), 6.46 (1H, s, —ArH), 6.59 (1H, s, =CH), 6.72-6.83 (3H, m, —ArH), 6.95-6.96 (1H, d, —ArH), 7.04-7.06 (2H, d, —ArH), 7.16-7.18 (3H, m, ArH), 7.36-7.38 (2H, d, —ArH), 7.47 (1H, s, —ArH), 7.79 (1H, s, —ArH), 7.91-7.93 (2H, d, —ArH), 9.6 (1H, s, —NH). MS m/z: 538.2 (M$^+$ + 1). |
| 28 | 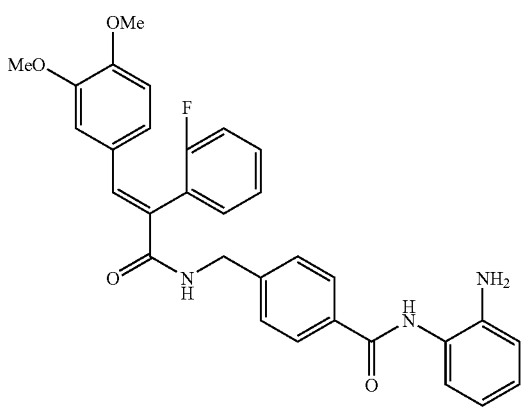 [SMILES: COc1ccc(/C=C(/C(=O)NCc2ccc(C(=O)Nc3ccccc3N)cc2)c2ccccc2F)cc1OC] | $^1$H NMR (DMSO-d$_6$) δ (ppm): 3.34 (3H, s, —OCH$_3$), 3.72 (3H, s, —OCH$_3$), 4.40-4.42 (2H, d, —CH$_2$), 4.89 (2H, s, —NH$_2$), 6.45 (1H, s, —ArH), 6.59 (1H, s, =CH), 6.74-6.79 (2H, m, —ArH), 6.83-6.86 (1H, d, —ArH), 6.95-6.98 (1H, d, —ArH), 7.15-7.17 (1H, d, —ArH), 7.21-7.39 (5H, m, ArH), 7.49 (1H, s, ArH), 7.60 (1H, s, —ArH), 7.91-7.93 (2H, d, —ArH), 8.15 (1H, s, —ArH), 9.62 (1H, s, —NH). MS m/z: 526.2 (M$^+$ + 1). |
| 29 | 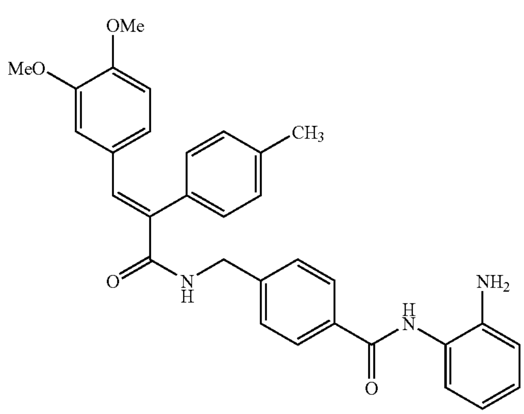 [SMILES: COc1ccc(/C=C(/C(=O)NCc2ccc(C(=O)Nc3ccccc3N)cc2)c2ccc(C)cc2)cc1OC] | $^1$H NMR (DMSO-d$_6$) δ (ppm): 2.36 (3H, s, —CH$_3$), 3.31 (3H, s, —OCH$_3$), 3.72 (3H, s, —OCH$_3$), 4.39-4.41 (2H, d, —NCH$_2$), 4.89 (2H, s, —NH$_2$), 6.40 (1H, s, —ArH), 6.41-6.48 (1H, s, —ArH) 6.79-6.80 (1H, s, =CH), 6.81-6.82 (2H, s, —ArH), 6.83-6.97 (1H, s, ArH), 7.13-7.15 (3H, m, —ArH), 7.29-7.31 (2H, d, —ArH), 7.35-7.37 (2H, d, —ArH), 7.46 (1H, s, —ArH), 7.50-7.86 (1H, s, —ArH) 7.91-7.93 (2H, d, —ArH), 9.61 (1H, s, —NH). MS m/z = 522.2 (M$^+$ + 1) |

| S. No | Structure | Analytical Data |
|---|---|---|
| 30 | 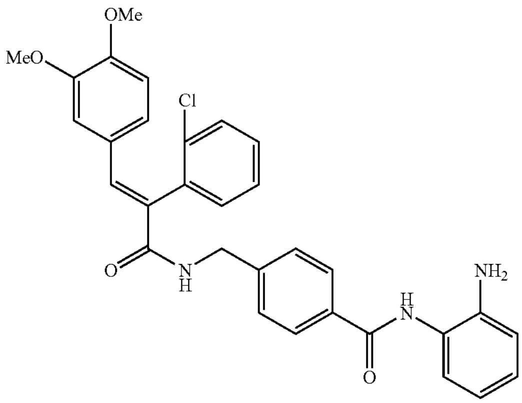 [SMILES: COc1ccc(/C=C(/C(=O)NCc2ccc(C(=O)Nc3ccccc3N)cc2)c2ccccc2Cl)cc1OC] | ¹H NMR (DMSO-d₆) δ (ppm): 3.36 (3H, s, —OCH₃), 3.75 (3H, s, —OCH₃), 4.44 (2H, d, —NCH₂), 4.89 (2H, s, —NH₂), 6.38 (1H, s, —ArH), 6.60-6.62 (1H, d, —ArH), 6.71-6.73 (3H, m, —ArH), 6.77-6.79 (1H, s, —ArH), 6.84-6.86 (1H, d, —ArH), 6.97-6.99 (1H, d, —ArH), 7.16-7.17 (1H, d, —ArH), 7.38-7.65 (5H, m, —ArH), 7.92-7.98 (3H, m, —ArH), 9.62 (1H, s, —NH). MS m/z = 541.8 (m⁺ + 1) |
| 31 | 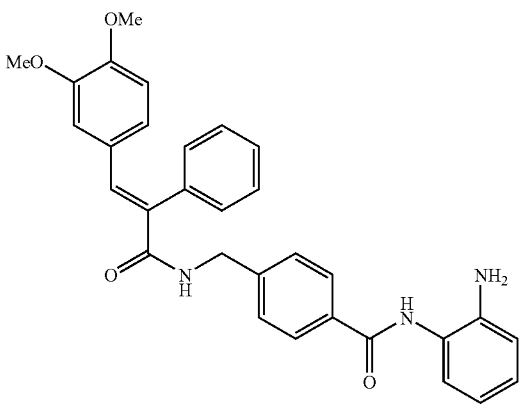 [SMILES: COc1ccc(/C=C(/C(=O)NCc2ccc(C(=O)Nc3ccccc3N)cc2)c2ccccc2)cc1OC] | ¹H NMR (DMSO-d₆) δ (ppm): 3.34 (3H, s, —OCH₃), 3.69 (3H, s, —OCH₃), 4.40-4.42 (2H, d, —NCH₂), 4.89 (2H, s, —NH₂), 6.38 (1H, s, —ArH), 6.58-6.61 (1H, s, =CH), 6.72-6.82 (3H, m, —ArH), 6.94-6.98 (1H, d, —ArH), 7.15-7.17 (1H, d, —ArH), 7.25-7.27 (2H, m, —ArH), 7.36-7.43 (2H, m, —ArH), 7.47-7.50 (1H, m, —ArH), 7.84-7.87 (3H, m, —ArH), 7.91-7.93 (3H, m, —ArH), 9.61 (1H, s, —NH). MS m/z = 507.9 (m⁺ + 1) |
| 32 | 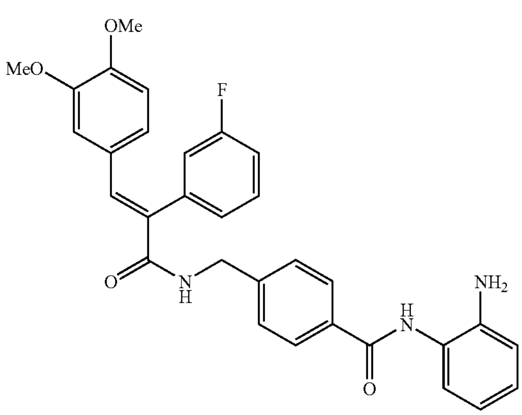 [SMILES: COc1ccc(/C=C(/C(=O)NCc2ccc(C(=O)Nc3ccccc3N)cc2)c2cccc(F)c2)cc1OC] | ¹H NMR (DMSO-d₆) δ (ppm): 3.34 (3H, s, —OCH₃), 3.72 (3H, s, —OCH₃), 4.40-4.42 (2H, d, —NCH₂), 4.89 (2H, s, —NH₂), 6.45 (1H, d, —ArH), 6.79 (1H, s, =CH), 6.84-6.86 (1H, d, —ArH), 6.9-6.93 (1H, d, —ArH), 7-7.05 (1H, m, —ArH), 7.09-7.10 (3H, m, ArH), 7.21-7.28 (2H, d, —ArH), 7.37-7.39 (2H, s, —ArH), 7.51 (2H, s, —ArH), 7.92-7.94 (3H, m, —ArH), 9.63 (1H, s, —NH). MS m/z = 525.8 (m⁺ + 1) |

| S. No | Structure | Analytical Data |
|---|---|---|
| 33 | (structure with methyl benzoate, 3-chlorophenyl, acrylamide linker, benzyl, benzamide, 2-aminophenyl) | ¹H NMR (DMSO-d₆) δ (ppm): 3.81 (3H, s, —OCH₃); 4.43-4.44 (2H, d, —CH₂); 4.88 (2H, s, —NH₂); 6.6 (1H, s, ArH); 6.77-6.79 (1H, d, ArH); 6.98 (1H, s, ArH); 7.15-7.17 (4H, m, —ArH); 7.27 (1H, s, ArH); 7.39-7.47 (4H, m, —ArH); 7.54 (1H, s, =CH); 7.77-7.79 (2H, d, ArH); 7.93-7.95 (2H, d, —ArH), 8.42 (1H, t, —NH), 9.66 (1H, s, —NH). MS m/z = 539.8 (M⁺ + 1) |
| 34 | (structure with methyl benzoate, 2-fluorophenyl, acrylamide linker, benzyl, benzamide, 2-aminophenyl) | ¹H NMR (DMSO-d₆) δ (ppm): 3.80 (3H, s, —OCH₃); 4.43-4.44 (2H, d, —CH₂); 4.90 (2H, s, —NH₂); 6.60 (1H, s, ArH); 6.77-6.79 (1H, d, ArH); 6.97 (1H, s, ArH); 7.16-7.23 (6H, m, —ArH); 7.29 (2H, s, ArH); 7.39-7.41 (1H, d, —ArH); 7.67 (1H, s, =CH); 7.76-7.78 (2H, d, ArH); 7.93-7.95 (2H, d, —ArH), 8.47 (1H, t, —NH), 9.64 (1H, s, —NH). MS m/z = 523.8 (M⁺ + 1) |
| 35 | (structure with methyl benzoate, 4-methoxyphenyl, acrylamide linker, benzyl, benzamide, 2-aminophenyl) | ¹H NMR (DMSO-d₆) δ (ppm): 3.78 (3H, s, —OCH₃); 3.80 (3H, s, —OCH₃); 4.41-4.43 (2H, d, —CH₂); 4.89 (2H, s, —NH₂); 6.60-6.62 (1H, t, ArH); 6.77-6.79 (1H, d, ArH); 6.95-6.99 (3H, d, ArH); 7.10-7.18 (5H, m, —ArH); 7.38-7.44 (3H, d, ArH); 7.75-7.77 (2H, d, ArH); 7.92-7.94 (2H, d, ArH); 8.19 (1H, t, —NH), 9.64 (1H, s, —NH). MS m/z 536.1 = (M⁺ + 1) |

| S. No | Structure | Analytical Data |
|---|---|---|
| 36 | 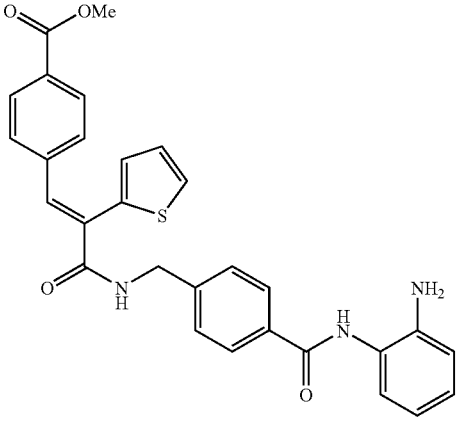 [SMILES: COC(=O)c1ccc(/C=C(/C(=O)NCc2ccc(C(=O)Nc3ccccc3N)cc2)c2cccs2)cc1] | ¹H NMR (DMSO-d₆) δ (ppm): 3.81 (3H, s, —OCH₃); 4.45 (2H, d, —CH₂); 4.88 (2H, s, —NH₂); 6.58 (1H, s, ArH); 6.75-6.77 (1H, d, ArH); 6.95 (1H, s, ArH); 7.00 (1H, d, —ArH); 7.07-7.08 (1H, d, ArH); 7.14 (1H, s, =CH); 7.26-7.28 (2H, d, ArH); 7.39-7.41 (2H, d, ArH); 7.48 (1H, s, ArH); 7.63-7.64 (1H, d, ArH); 7.81-7.83 (2H, d, ArH); 7.92-7.94 (2H, d, —ArH), 8.55 (1H, t, —NH), 9.62 (1H, s, —NH). MS m/z 512.8 = (M⁺ + 1) |
| 37 | 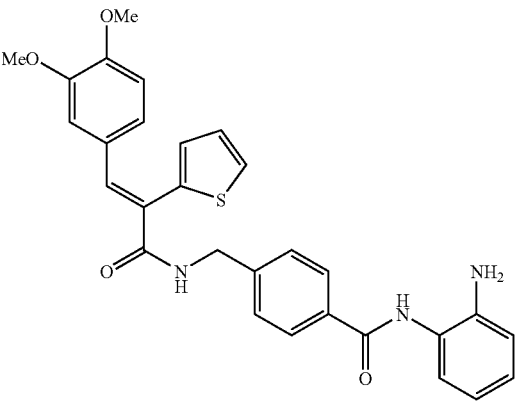 [SMILES: COc1ccc(/C=C(/C(=O)NCc2ccc(C(=O)Nc3ccccc3N)cc2)c2cccs2)cc1OC] | ¹H NMR (DMSO-d₆) δ (ppm): 3.45 (3H, s, —OCH₃), 3.73 (3H, s, —OCH₃), 4.43 (2H, d, —NCH₂), 4.89 (2H, s, —NH₂), 6.58-6.59 (2H, d, —ArH), 6.61-6.79 (1H, m, —ArH), 6.84-6.89 (2H, m, —ArH), 6.96 (1H, s, —ArH), 7.06-7.08 (1H, d, —ArH), 7.15-7.20 (2H, m, —ArH), 7.37-7.39 (2H, d, —ArH), 7.58 (1H, s, =CH), 7.71-7.72 (1H, d, —ArH), 7.92-7.93 (2H, d, —ArH), 8.06 (1H, s, —ArH), 9.6 (1H, s, —NH). MS m/z = 513.8 (m⁺ + 1) |
| 38 | 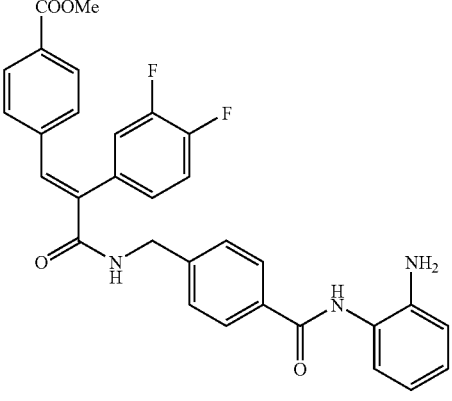 [SMILES: COC(=O)c1ccc(/C=C(/C(=O)NCc2ccc(C(=O)Nc3ccccc3N)cc2)c2ccc(F)c(F)c2)cc1] | ¹H NMR (DMSO-d₆) δ (ppm): 3.81 (3H, s, —OCH₃), 4.42-4.44 (2H, d, —NCH₂), 4.89 (2H, s, —NH₂), 6.60-6.62 (1H, s, —ArH), 6.77-6.79 (1H, s, —ArH), 6.95-6.99 (1H, m, —ArH), 7.03 (1H, m, —ArH), 7.15-7.18 (3H, m, —ArH), 7.33-7.41 (3H, m, —ArH), 7.46-7.49 (1H, m, =CH), 7.59 (1H, d, —ArH), 7.79-7.81 (2H, d, —ArH), 7.92-7.94 (2H, d, ArH), 8.27-8.30 (1H, s, —ArH), 9.63 (1H, s, —NH). MS m/z = 541.8 (m⁺ + 1) |

| S. No | Structure | Analytical Data |
|---|---|---|
| 39 | 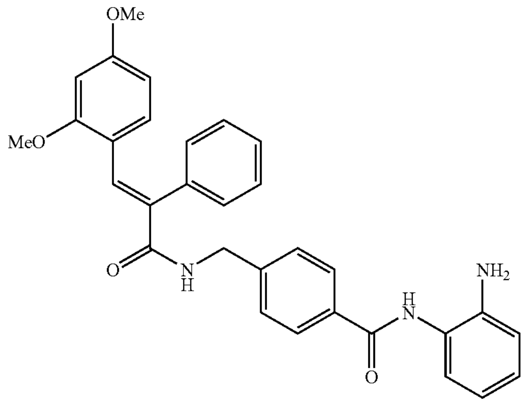 [SMILES: COc1ccc(/C=C(/C(=O)NCc2ccc(C(=O)Nc3ccccc3N)cc2)c2ccccc2)c(OC)c1] | ¹H NMR (DMSO-d₆) δ (ppm): 3.70 (3H, s, —OCH₃), 3.82 (3H, s, —OCH₃), 4.39- 4.40 (2H, d, —NCH₂), 4.89 (2H, s, —NH₂), 6.16-6.19 (1H, s, —ArH), 6.42-6.44 (1H, d, —ArH), 6.53-6.54 (2H, d, —ArH), 6.60-6.62 (2H, d, —ArH), 6.77-6.79 (1H, d, —ArH), 6.95-6.97 (1H, m, —ArH), 7.15-7.18 (3H, m, —ArH), 7.36-7.42 (5H, m, —ArH), 7.65 (1H, s, —ArH), 7.86-7.93 (1H, m, —ArH), 9.63 (1H, s, —NH). MS m/z 507.9 = (m⁺ + 1) |
| 40 | 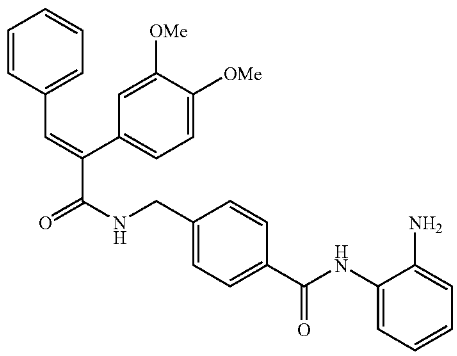 [SMILES: COc1ccc(/C(=C\c2ccccc2)C(=O)NCc2ccc(C(=O)Nc3ccccc3N)cc2)cc1OC] | ¹H NMR (DMSO-d₆) δ (ppm): 3.34 (3H, s, —OMe), 3.69 (3H, s, OMe), 4.40-4.42 (2H, s, CH₂), 4.89 (2H, s, —NH₂), 6.38 (1H, s, ArH), 6.58-6.61 (1H, m, ArH), 6.73- 6.83 (3H, m, ArH), 6.94-6.98 (1H, m, ArH), 7.15-7.17 (2H, d, ArH), 7.25-7.27 (2H, d, ArH), 7.36-7.51 (4H, m, ArH), 7.84-7.93 (3H, m, ArH and —NH), 9.62 (1H, s, —NH). MS m/z = 507.2 (m⁺ + 1) |
| 41 | 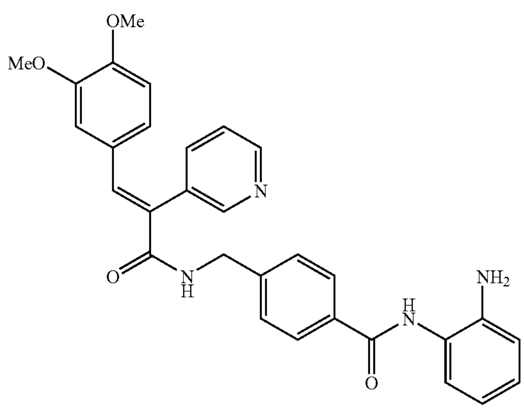 | ¹H NMR (DMSO-d₆) δ (ppm): 3.34 (3H, s, —OMe), 3.71 (3H, s, OMe), 4.40-4.43 (2H, s, CH₂), 4.89 (2H, s, —NH₂) 6.42 (1H, s, ArH), 6.58-6.61 (1H, m, ArH), 6.68-6.69 (1H, d, ArH), 6.77-6.79 (1H, d, ArH), 6.83-6.85 (1H, d, ArH), 6.95-6.99 (1H, t, ArH), 7.16-7.17 (1H, d, ArH), 7.38-7.40 (2H, d, ArH), 7.48-7.51 (1H, t, ArH), 7.58 (1H, s, =CH), 7.69-7.71 (1H, d, —ArH), 7.92-7.94 (2H, d, ArH), 8.20-8.24 (1H, t, —NH), 8.39 (1H, s, —ArH), 8.59-8.60 (1H, d, ArH), 9.82 (1H, s, —NH). MS m/z 508.8 = (m⁺ + 1) |
| 42 | 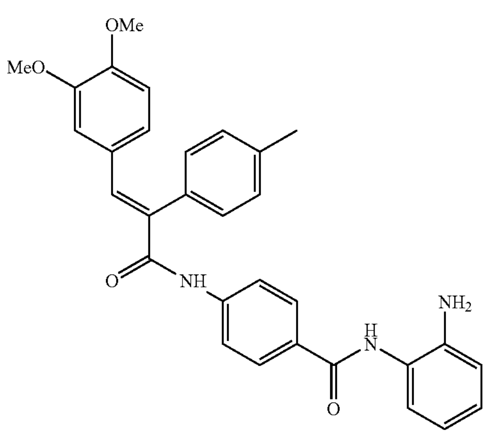 [SMILES: COc1ccc(/C=C(/C(=O)Nc2ccc(C(=O)Nc3ccccc3N)cc2)c2ccc(C)cc2)cc1OC] | ¹H NMR (DMSO-d₆) δ (ppm): 2.36 (3H, s, —CH₃), 3.35 (3H, s, —OCH₃), 3.73 (3H, s, —OMe ), 4.40-4.43 (2H, s, CH₂), 4.88 (2H, s, —NH₂), 6.52 (1H, s, —ArH), 6.59-6.62 (1H, t, —ArH), 6.77-6.87 (3H, m, —ArH), 6.94-6.97 (1H, t, —ArH), 7.15-7.19 (3H, t, —ArH), 7.27- 7.29 (2H, d, —ArH), 7.40 (1H, s, =CH), 7.79-7.82 (2H, d, —ArH), 7.95-7.97 (2H, d, ArH), 9.59 (1H, s, —NH), 9.96 (1H, s, —NH). MS m/z = 508.2 (m⁺ + 1) |

| S. No | Structure | Analytical Data |
|---|---|---|
| 43 | 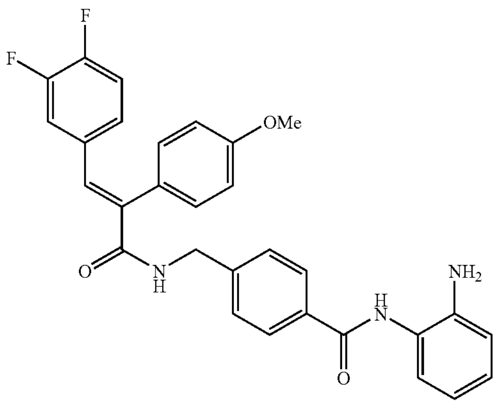 [SMILES: COc1ccc(/C(=C\c2ccc(F)c(F)c2)C(=O)NCc2ccc(C(=O)Nc3ccccc3N)cc2)cc1] | ¹H NMR (DMSO-d₆) δ (ppm): 3.79 (3H, s, —OCH₃), 4.39-4.41 (2H, d, —NCH₂), 4.89 (2H, s, —NH₂), 6.58-6.61 (1H, t, —ArH), 6.77-6.79 (1H, d, —ArH), 6.95-7.04 (5H, m, —ArH), 7.13-7.17 (3H, m, —ArH), 7.25-7.38 (3H, m, —ArH), 7.41 (1H, s, =CH), 7.92-7.94 (2H, m, ArH), 8.04 (1H, t, —NH), 9.63 (1H, s, —NH). MS m/z = 514.2 (m⁺ + 1) |
| 44 | 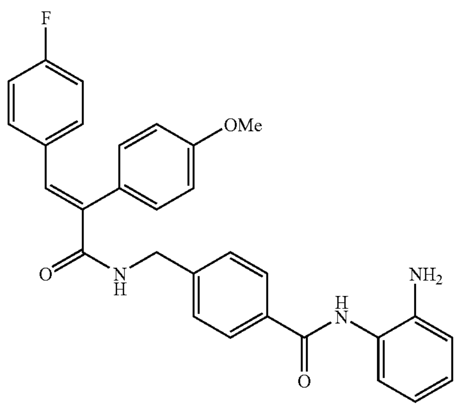 [SMILES: COc1ccc(/C(=C\c2ccc(F)cc2)C(=O)NCc2ccc(C(=O)Nc3ccccc3N)cc2)cc1] | ¹H NMR (DMSO-d₆) δ (ppm): 3.79 (3H, s, OCH₃), 4.39-4.41 (2H, d, —NCH₂), 4.89 (2H, s, —NH₂), 6.59 (1H, t, —ArH), 6.77- 6.79 (1H, d, —ArH), 6.97-7.07 (7H, m, —ArH), 7.13-7.17 (3H, m, —ArH), 7.36-7.39 (2H, d, —ArH), 7.45 (1H, s, =CH), 7.92- 7.97 (3H, m, —ArH and —NH), 9.62 (1H, s, —NH). MS m/z = 496.2 (m⁺ + 1) |
| 45 | 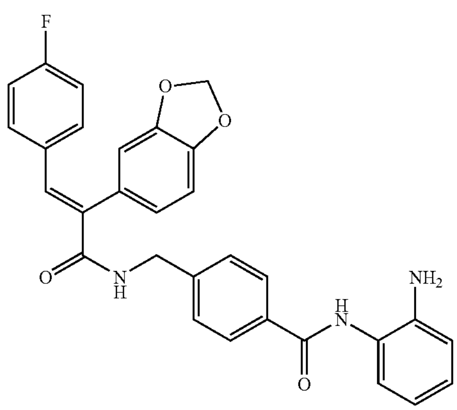 [SMILES: Nc1ccccc1NC(=O)c1ccc(CNC(=O)/C(=C/c2ccc(F)cc2)c2ccc3c(c2)OCO3)cc1] | ¹H NMR (DMSO-d₆) δ (ppm): 4.39-4.41 (2H, d, —NCH₂), 4.89 (2H, s, —NH₂), 6.08 (2H, s, —OCH₂), 6.58-6.61 (1H, t, —ArH), 6.68-6.71 (1H, d, —ArH), 6.78-6.79 (2H, m, —ArH), 6.97-6.99 (2H, m, —ArH), 7.08-7.12 (5H, m, —ArH), 7.36-7.39 (2H, d, —ArH), 7.48 (1H, s, =CH), 7.91-7.93 (3H, m, ArH and —NH), 9.62 (1H, s, —NH). MS m/z 510.2 (m⁺ + 1) |
| 46 | 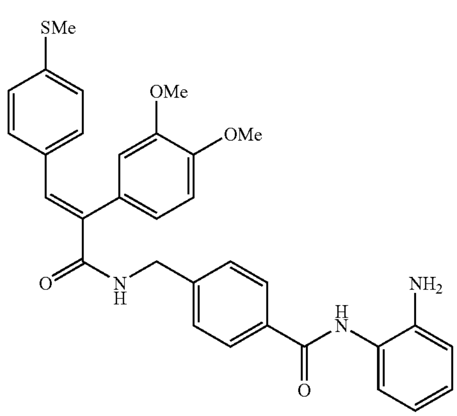 [SMILES: COc1ccc(/C(=C\c2ccc(SC)cc2)C(=O)NCc2ccc(C(=O)Nc3ccccc3N)cc2)cc1OC] | ¹H NMR (DMSO-d₆) δ (ppm): 2.42 (3H. s, —SCH₃), 3.69 (3H, s, —OCH₃), 3.79 (3H, s, —OCH₃), 4.39-4.41 (2H, d, —NCH₂), 4.89 (2H, s, —NH₂), 6.58-6.62 (1H, t, —ArH), 6.72-6.74 (1H, d, —ArH), 6.77-6.81 (2H, d, —ArH), 6.95-7.03 (4H, m, —ArH), 7.07-7.09 (2H, d, —ArH), 7.15-7.17(1H, d, —ArH); 7.36-7.38 (2H, d, —ArH), 7.45 (1H, s, =CH), 7.77-7.80 (1H, t, —NH and —NH), 7.91-7.93 (2H, d, —ArH), 9.62 (1H, s, —NH). MS m/z = 554.2 (m⁺ + 1) |

| S. No | Structure | Analytical Data |
|---|---|---|
| 47 | 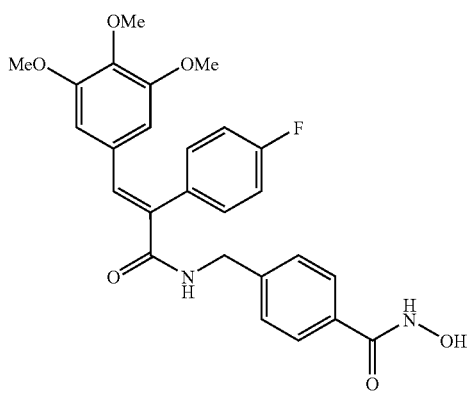 | $^1$H NMR (DMSO-d$_6$) δ (ppm): 2.42 (3H, s, —SCH$_3$), 4.39-4.41 (2H, d, —NCH$_2$), 4.89 (2H, s, —NH$_2$), 6.08 (2H, s, —OCH$_2$), 6.58-6.61 (1H, t, —ArH), 6.66-6.68 (1H, d, —ArH), 6.72-6.74 (1H, d, —ArH), 6.78-6.79 (2H, m, —ArH), 6.94-7.01 (4H, m, —ArH), 7.15-7.17 (1H, m, —ArH), 7.44 (1H, s, =CH), 7.87-7.92 (3H, m, ArH and —NH), 9.61 (1H, s, —NH). MS m/z = 536.3 (m$^+$ + 1) |

EXAMPLE 48

Synthesis of 4-((2-(4-fluorophenyl)-3-(3,4,5 trimethoxy phenyl)acrylamido) methyl)-N-hydroxybenzamide

Step 1

Preparation of 3-(3,4,5-trimethoxyphenyl)-2-(4-fluorophenyl)acrylic acid

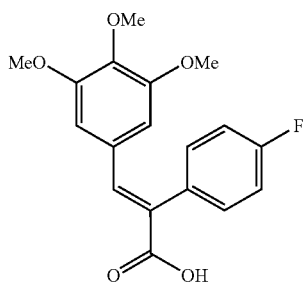 [SMILES: COc1cc(/C=C(/C(=O)O)c2ccc(F)cc2)cc(OC)c1OC]

A mixture of 4-fluoro phenyl acetic acid (2 g, 13 mmol), 3,4,5 trimethoxybenzaldehyde (2.5 g, 13 mmol), Ac$_2$O (10 mL) and DIPEA (2.9 mL, 16.8 mmol) was stirred at room temperature for 12 hours. Upon completion, as monitored by TLC using DCM:MeOH (9:1) as the eluent, 10% aqueous HCl (10 mL) was added to the reaction mixture; the precipitate formed was filtered and dissolved in DCM (100 mL). The organic layer was washed with 10% aqueous NaOH (3×50 mL) and the basic aqueous solution was acidified with 10% aqueous HCl to pH 3. The precipitate formed was filtered, washed with 100 mL water and dried to get the product (2.4 g, 56% yield).

Step 2

Preparation of ethyl 4-((2-(4-fluorophenyl)-3-(3,4,5 trimethoxyphenyl)acrylamido) methyl)benzoate

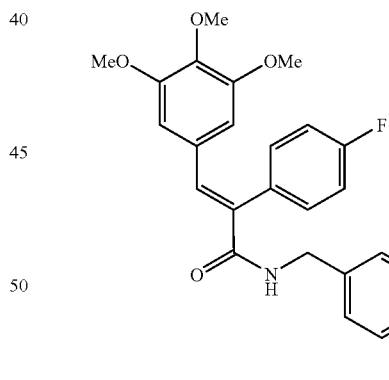

To a solution of 3-(3,4,5-trimethoxyphenyl)-2-(4-fluorophenyl)acrylic acid (0.6 g, 18 mmol) in DMF (5 mL) was added ethyl-4-aminomethylbenzoate.HCl (0.375 g, 21.6 mmol), EDCI (0.69 g, 36 mmol) and HOBt (0.24 g, 18 mmol). TEA (0.75 mL, 36 mmol) was added dropwise with constant stirring to the above reaction mixture and stirred overnight at room temperature. Subsequently the reaction mixture was evaporated to dryness, the residue was dissolved in ethyl acetate and washed successively with 1N HCl (3×50 mL), saturated NaHCO$_3$ (3×50 mL) and brine solution (3×50 mL). The organic layer was dried over Na$_2$SO$_4$ and concentrated to give the pure compound (0.4 g, 50% yield).

Step 3

Preparation of 4-((2-(4-fluorophenyl)-3-(3,4,5-trimethoxyphenyl)acrylamido)methyl)-N-hydroxybenzamide

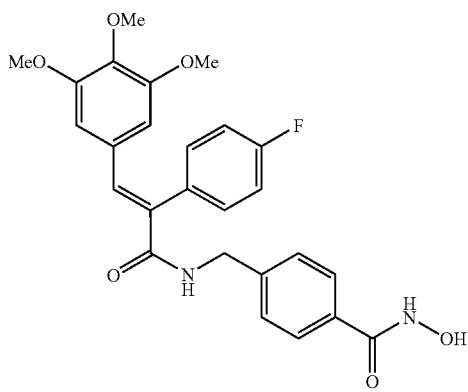 [SMILES: COc1cc(/C=C(/C(=O)NCc2ccc(C(=O)NO)cc2)c2ccc(F)cc2)cc(OC)c1OC]

Hydroxylamine hydrochloride (1.25 g, 18 mmol) in methanol (3 mL) was mixed with KOH (1.0 g, 18 mmol) in methanol (6 mL) at 0° C. and the reaction mixture was sonicated for 5 minutes. A white precipitate was formed which was filtered. The filtrate was immediately added to the ethyl 4-((2-(4-fluorophenyl)-3-(3,4,5-trimethoxyphenyl)acrylamido)methyl)benzoate (0.4 g, 1 mmol) followed by the addition of KOH (0.084 g, 1.5 mmol) and the mixture was stirred at room temperature for 1 hour. Around 20 mL of water was added to the reaction mixture and it was neutralized to pH 7 by addition of dilute acetic acid. Upon standing, a colorless precipitate was formed, it was filtered, dried and triturated with dichloromethane/hexanes (1:1, 20 mL), to afford the required compound as a pure colorless solid (0.254 g, 38% yield). $^1$H NMR (DMSO-$d_6$) δ (ppm): 3.49 (6I-1, s, —OCH$_3$), 3.60 (3H, s, —OCH$_3$), 4.36 (2H, d, —CH$_2$), 6.32 (2H, s, Ar—H), 7.29-7.39 (6H, d, Ar—H), 7.48 (1H, s, =CH), 7.69 (2H, d, Ar—H), 7.96 (1H, t, —NH), 8.99 (1H, s, —OH), 11.16 (1H, s, —NH); MS m/z: 497.1 (M$^+$+1).

The following compounds were prepared according to the above procedure

| S. No | Structure | Analytical Data |
|---|---|---|
| 49 | 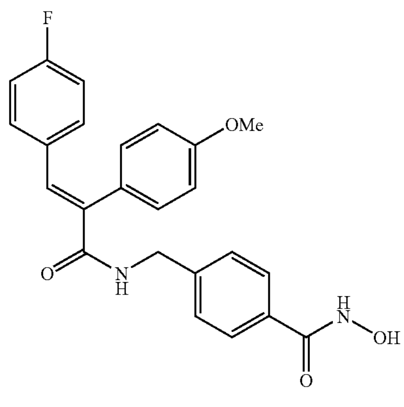 [SMILES: COc1ccc(/C(=C\c2ccc(F)cc2)C(=O)NCc2ccc(C(=O)NO)cc2)cc1] | $^1$H NMR (DMSO-$d_6$) δ (ppm): 3.78 (3H, s, —OCH$_3$), 4.34 (2H, d, —CH$_2$), 6.98-7.13 (8H, m, Ar—H), 7.30 (2H, d, Ar—H), 7.43 (1H, s, =CH), 7.68 (2H, d, Ar—H), 7.93 (1H, t, NH), 8.99 (1H, s, —OH), 11.16 (1H, s, —NH); MS m/z: 421.1 (M$^+$ + 1). |
| 50 | 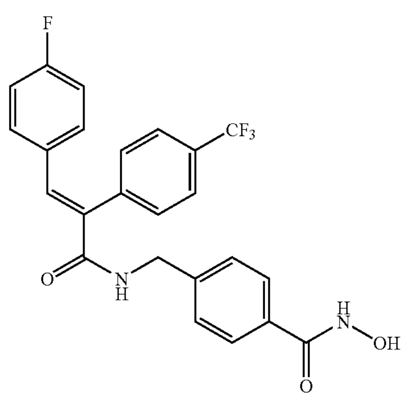 [SMILES: O=C(NCc1ccc(C(=O)NO)cc1)/C(=C/c1ccc(F)cc1)c1ccc(C(F)(F)F)cc1] | $^1$H NMR (DMSO-$d_6$) δ (ppm): 4.37-4.39 (2H, d, —CH$_2$), 7.02-7.10 (4H, m, Ar—H), 7.32-7.34 (2H, d, Ar—H), 7.43-7.45 (2H, d, Ar—H), 7.55 (1H, s, =CH), 7.69-7.71 (2H, d, Ar—H), 7.77-7.79 (2H, d, Ar—H), 8.25 (1H, t, NH), 9.01 (1H, s, —OH), 11.18 (1H, s, —NH); MS m/z: 459.1 (M$^+$ + 1). |

| S. No | Structure | Analytical Data |
|---|---|---|
| 51 | (4-fluorophenyl, phenyl substituted acrylamide with N-benzyl hydroxamic acid) | ¹H NMR (DMSO-d₆) δ: 4.36-4.38 (2H, d, —CH₂), 7.02-7.04 (4H, d, Ar—H), 7.20-7.22 (2H, d, Ar—H), 7.31-7.33 (2H, d, Ar—H), 7.40-7.49 (4H, m, Ar—H & =CH), 7.68-7.70 (2H, d, Ar—H), 8.02 (1H, t, NH), 9.00 (1H, s, —OH), 11.16 (1H, s, —NH); MS m/z: 391.1 (M⁺ + 1). |
| 52 | (4-SMe-phenyl, 4-fluorophenyl acrylamide with N-benzyl hydroxamic acid) | ¹H NMR (DMSO-d₆) δ (ppm): 2.42 (3H, s, —SCH₃), 4.35-4.37 (2H, d, —CH₂), 6.92-6.94 (2H, d, Ar—H), 7.07-7.09 (2H, d, Ar—H), 7.25-7.32 (6H, m, Ar—H), 7.46 (1H, s, =CH), 7.68-7.70 (2H, d, Ar—H), 8.02 (1H, t, NH), 9.00 (1H, s, —OH), 11.17 (1H, s, —NH); MS m/z: 437.1 (M⁺ + 1). |
| 53 | (4-OMe-phenyl, 4-fluorophenyl acrylamide with N-benzyl hydroxamic acid) | ¹H NMR (DMSO-d₆) δ (ppm): 3.70 (3H, s, —OCH₃), 4.35-4.36 (2H, d, —CH₂), 6.76-6.78 (2H, d, Ar—H), 6.92-6.94 (2H, d, Ar—H), 7.24-7.47 (6H, m, Ar—H), 7.47 (1H, s, =CH), 7.68-7.70 (2H, d, Ar—H), 7.92 (1H, t, NH), 9.00 (1H, s, —OH), 11.16 (1H, s, —NH); MS m/z: 421.1 (M⁺ + 1). |
| 54 | (2,4,6-trifluorophenyl, 4-fluorophenyl acrylamide with N-benzyl hydroxamic acid) | ¹H NMR (DMSO-d₆) δ (ppm): 4.39-4.40 (2H, d, —CH₂), 7.08-7.13 (7H, m, Ar—H), 7.34-7.36 (2H, d, Ar—H), 7.70-7.72 (2H, d, Ar—H), 8.52 (1H, t, NH), 9.00 (1H, s, —OH), 11.18 (1H, s, —NH); MS m/z: 445.1 (M⁺ + 1). |

| S. No | Structure | Analytical Data |
|---|---|---|
| 55 | (structure with SMe-phenyl, pyridin-3-yl, acrylamide-CH2-C6H4-C(O)NHOH) | ¹H NMR (DMSO-d₆) δ (ppm): 2.42 (3H, s, —SMe), 4.38-4.39 (2H, d, —NCH₂), 6.91-6.92 (2H, d, —ArH), 7.07-7.09 (2H, d, —ArH), 7.33-7.35 (2H, d, —ArH), 7.45-7.48 (1H, t, ArH), 7.56 (1H, s, =CH), 7.66-7.71 (3H, m, —ArH), 7.95 (2H, s, —ArH), 8.30-8.35 (1H, m, —ArH) 9.02 (1H, s, —OH), 11.19 (1H, s, —NH). MS m/z = 420.1 (M⁺ + 1) |
| 56 | (structure with SMe-phenyl, 2-chlorophenyl, acrylamide-CH2-C6H4-C(O)NHOH) | ¹H NMR (DMSO-d₆) δ (ppm): 2.41 (3H, s, —SMe), 4.36-4.39 (2H, d, —NCH₂), 6.87-6.89 (2H, d, —ArH), 7.05-7.07 (2H, d, —ArH), 7.22-7.24 (1H, d, —ArH), 7.30-7.33 (2H, d, ArH), 7.39 (1H, s, =CH), 7.47 (1H, s, —ArH), 7.59-7.61 (2H, d, —ArH), 7.67-7.69 (2H, d, —ArH), 8.02 (1H, s, —OH), 8.99 (1H, s, —NH) 11.19 (1H, s, —NH),. MS m/z = 452.95 (M⁺ + 1) |
| 57 | (structure with SMe-phenyl, 4-methoxyphenyl, acrylamide-CH2-C6H4-C(O)NHOH) | ¹H NMR (DMSO-d₆) δ (ppm): 2.50 (3H, s, —CH₃), 3.79 (3H, s, —OMe), 4.35-4.37 (2H, d, —NCH₂), 6.94-6.96 (2H, d, —ArH), 6.99-7.01 (2H, d, —ArH), 7.05-7.07 (2H, d, ArH), 7.12-7.14 (2H, d, —ArH), 7.26 (2H, s, —ArH), 7.40 (1H, s, =CH), 7.67-7.69 (2H, m, —ArH), 7.85-7.88 (1H, m, —ArH), 8.99 (1H, s, —OH), 11.16 (1H, s, —NH), MS m/z = 447.1 (M⁺ + 1) |
| 58 | (structure with SMe-phenyl, 4-methylphenyl, acrylamide-CH2-C6H4-C(O)NHOH) | ¹H NMR (DMSO-d₆) δ (ppm): 2.41 (3H, s, —CH₃), 2.49 (3H, s, —SMe), 4.35-4.37 (2H, d, —NCH₂), 6.93-6.94 (2H, d, —ArH), 7.04-7.06 (2H, d, —ArH), 7.09-7.11 (2H, d, —ArH), 7.24-7.26 (2H, d, —ArH), 7.29-7.30 (2H, d, —ArH), 7.41 (1H, s, =CH), 7.68-7.69 (2H, d, —ArH), 7.85-7.87 (1H, m, —ArH) 9.00 (1H, s, —OH), 11.17 (1H, s, —NH), MS m/z = 432.5 (M⁺ + 1) |

| S. No | Structure | Analytical Data |
|---|---|---|
| 59 | 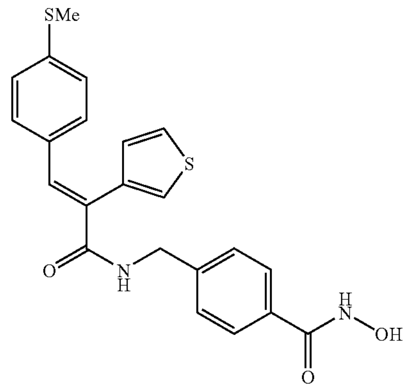 [SMILES: CSc1ccc(/C=C(/C(=O)NCc2ccc(C(=O)NO)cc2)c2ccsc2)cc1] | ¹H NMR (DMSO-d₆) δ (ppm): 2.43 (3H, s, —SCH₃), 4.37-4.38 (2H, d, —CH₂), 6.92-6.93 (1H, d, —ArH), 6.96-6.98 (2H, d, —ArH), 7.07-7.09 (2H, d, —ArH), 7.30-7.32 (2H, d, —ArH), 7.44-7.50 (2H, t, —ArH), 7.65-7.70 (3H, m, —ArH & =CH), 7.94-7.97 (1H, t, —NH), 8.99 (1H, t, —OH), 11.17 (1H, s, —NH). MS m/z = 425.1 (M⁺ + 1). |
| 60 | 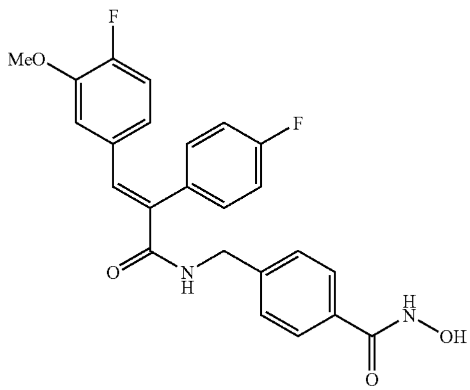 [SMILES: COc1cc(/C=C(/C(=O)NCc2ccc(C(=O)NO)cc2)c2ccc(F)cc2)ccc1F] | ¹H NMR (DMSO-d₆) δ (ppm): 3.51 (3H, s, —OCH₃), 4.36-4.37 (2H, d, —CH₂), 6.64-6.70 (2H, m, —ArH), 7.05-7.10 (1H, m, —ArH), 7.27-7.30 (4H, m, —ArH), 7.30-7.32 (2H, d, —ArH), 7.49 (1H, s, =CH), 7.68-7.70 (2H, d, —ArH), 8.04-8.05 (1H, t, —NH), 9.00 (1H, s, —OH), 11.17 (1H, s, —NH). MS m/z = 439.1 (M⁺ + 1). |
| 61 | 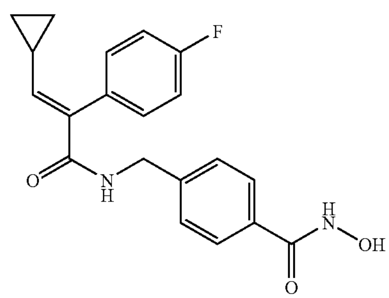 [SMILES: O=C(NCc1ccc(C(=O)NO)cc1)/C(=C/C1CC1)c1ccc(F)cc1] | ¹H NMR (DMSO-d₆) δ (ppm): 0.60-0.61 (2H, m, —CH₂), 0.80-0.83 (2H, m, —CH₂), 1.24-1.27 (1H, t, —CH), 4.29-4.31 (2H, d, —CH₂), 6.01-6.04 (1H, d, =CH), 7.22-7.32 (6H, m, —ArH), 7.66-7.68 (2H, d, —ArH), 7.84-7.87 (1H, t, —NH), 9.00 (1H, s, —OH), 11.17 (1H, s, —NH). MS m/z: 355.1 (M⁺ + 1). |
| 62 | 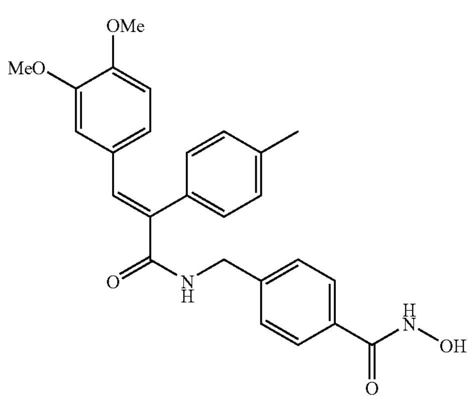 [SMILES: COc1ccc(/C=C(/C(=O)NCc2ccc(C(=O)NO)cc2)c2ccc(C)cc2)cc1OC] | ¹H NMR (DMSO-d₆) δ (ppm): 2.35 (3H, s, —CH₃), 3.38 (3H, s, —OCH₃), 3.69 (3H, s, —OMe), 4.35-4.37 (2H, d, —NCH₂), 6.39 (1H, s, —ArH), 6.71-6.73 (1H, d, —ArH), 6.79-6.82 (1H, d, —ArH), 7.12-7.13 (2H, d, —ArH), 7.28-7.30 (4H, m, —ArH) 7.45 (1H, s, =CH), 7.67-7.69 (2H, d, —ArH), 7.72-7.75 (1H, t, —NH), 9.01 (1H, s, —NH), 11.16 (1H, s, —OH). MS m/z = 447.2 (m⁺ + 1) |

| S. No | Structure | Analytical Data |
|---|---|---|
| 63 | 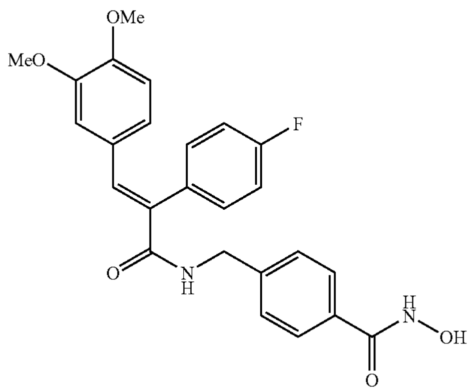 [SMILES: COc1ccc(/C=C(/C(=O)NCc2ccc(C(=O)NO)cc2)c2ccc(F)cc2)cc1OC] | $^1$H NMR (DMSO-d$_6$) δ (ppm): 3.38 (3H, s, —OCH$_3$), 3.70 (3H, s, —OMe), 4.35-4.37 (2H, d, —NCH$_2$), 6.44 (1H, s, —ArH), 6.69-6.71 (1H, d, —ArH), 6.82-6.85 (1H, d, ArH), 7.28-7.32 (6H, m, —ArH), 7.48 (1H, s, —ArH), 7.68-7.69 (2H, d, —ArH), 7.91 (1H, t, —NH), 8.99 (1H, s, —NH), 11.16 (1H, s, —OH). MS m/z = 451.2 (m$^+$ + 1) |
| 64 | 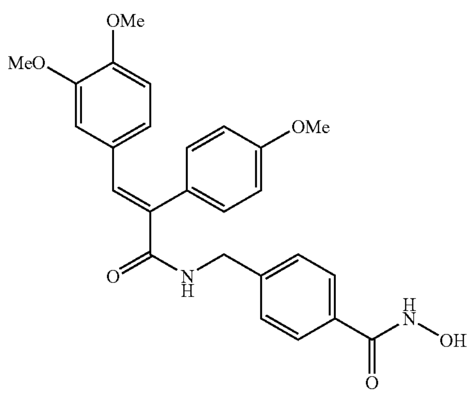 [SMILES: COc1ccc(/C(=C\c2ccc(OC)c(OC)c2)C(=O)NCc2ccc(C(=O)NO)cc2)cc1] | $^1$H NMR (DMSO-d$_6$) δ (ppm): 3.36 (3H, s, —OCH$_3$), 3.70 (3H, s, —OCH$_3$), 3.79 (3H, s, —OMe), 4.35-4.36 (2H, d, —NCH$_2$), 6.45 (1H, s, —ArH), 6.71-6.73 (1H, d, —ArH), 6.80-6.83 (1H, d, ArH), 7.03-7.05 (2H, d, —ArH), 7.14-7.17 (2H, d, —ArH), 7.29-7.31 (2H, d, —ArH), 7.44 (1H, s, =CH), 7.68-7.69 (2H, d, —ArH), 7.74-7.77 (1H, t, —NH), 9.00 (1H, s, —NH), 11.16 (1H, s, —OH). MS m/z = 463.2 (m$^+$ + 1) |
| 65 | 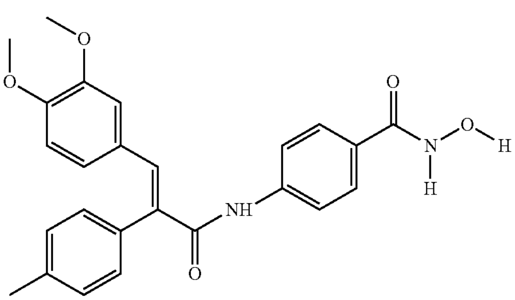 [SMILES: COc1ccc(/C=C(/C(=O)Nc2ccc(C(=O)NO)cc2)c2ccc(C)cc2)cc1OC] | $^1$H NMR (DMSO-d$_6$) δ (ppm): 2.35 (3H, s, —CH$_3$), 3.36 (3H, s, —OCH$_3$), 3.72 (3H, s, —OMe), 6.52 (1H, s, —ArH), 6.78-6.86 (2H, m, —ArH), 7.15-7.17 (2H, d, —ArH), 7.26-7.28 (2H, d, —ArH), 7.37 (1H, s, =CH), 7.69-7.75 (4H, m, —ArH), 8.95 (1H, t, —NH), 9.90 (1H, s, —NH), 11.11 (1H, s, —OH). MS m/z = 433.2 (m$^+$ + 1) |
| 66 | 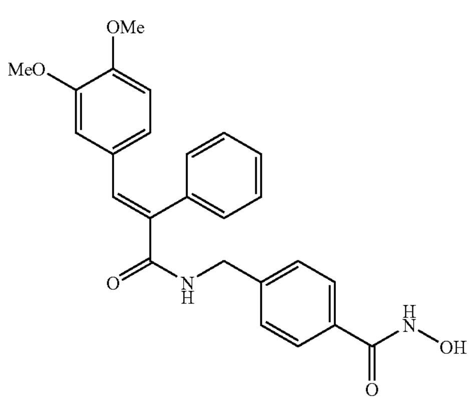 [SMILES: COc1ccc(/C=C(/C(=O)NCc2ccc(C(=O)NO)cc2)c2ccccc2)cc1OC] | $^1$H NMR (DMSO-d$_6$) δ (ppm): 3.29 (3H, s, —OCH$_3$), 3.69 (3H, s, —OMe), 4.36-4.38 (2H, d, —NCH$_2$), 6.72-6.74 (1H, d, —ArH), 6.80-6.82 (1H, d, ArH), 7.24-7.32 (4H, m, —ArH), 7.39-7.50 (5H, m, —ArH), 7.68-7.69 (2H, d, —ArH), 7.82-7.85 (1H, t, —NH), 8.99 (1H, s, —NH), 11.16 (1H, s, —OH). MS m/z = 433.2 (m$^+$ + 1) |

| S. No | Structure | Analytical Data |
|---|---|---|
| 67 | 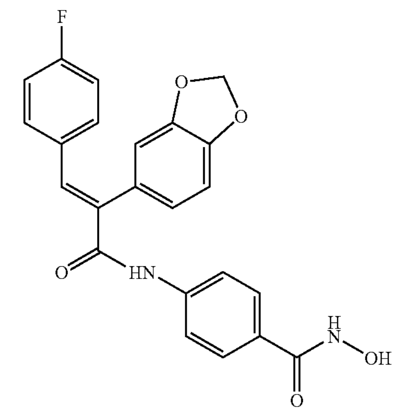 [SMILES: O=C(Nc1ccc(C(=O)NO)cc1)/C(=C/c1ccc(F)cc1)c1ccc2c(c1)OCO2] | $^1$H NMR (DMSO-d$_6$) δ (ppm): 6.07 (2H, s, —OCH$_2$), 6.69-6.71 (1H, d, —ArH), 6.78 (1H, s, ArH), 6.94-6.97 (1H, d, —ArH), 7.09-7.21 (4H, m, —ArH), 7.38 (1H, s, =CH), 7.71-7.76 (4H, m, —ArH), 8.96 (1H, s, —NH), 9.97 (1H, s, —NH), 11.13 (1H, s, —OH). MS m/z = 419.1 (m$^+$ − 1) |
| 68 | 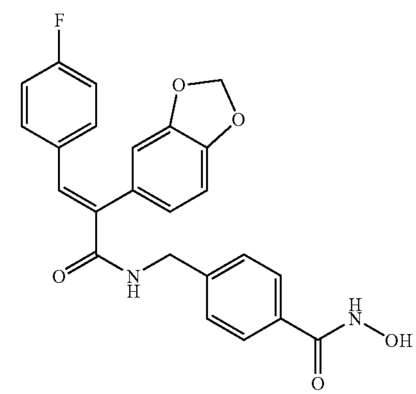 [SMILES: O=C(NCc1ccc(C(=O)NO)cc1)/C(=C/c1ccc(F)cc1)c1ccc2c(c1)OCO2] | $^1$H NMR (DMSO-d$_6$) δ (ppm): 4.35-4.37 (2H, d, —NCH$_2$), 6.07 (2H, s, —OCH$_2$), 6.65-6.67 (1H, d, —ArH), 6.77 (1H, s, ArH), 6.97-6.99 (1H, d, —ArH), 7.05-7.13 (4H, m, —ArH), 7.29-7.34 (2H, t, —ArH), 7.47 (1H, s, =CH), 7.68-7.69 (2H, d, —ArH), 7.91-7.94 (1H, t, —NH), 9.36 (1H, s, —NH), 10.5 (1H, s, —OH). MS m/z = 435.2 (m$^+$ + 1) |
| 69 | 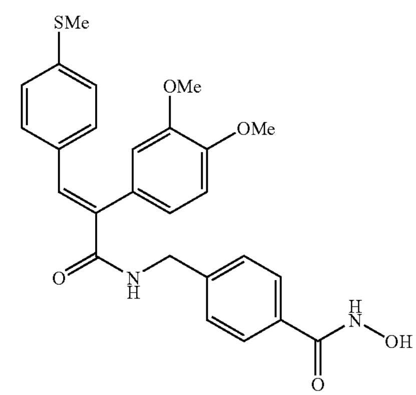 [SMILES: COc1ccc(/C(=C\c2ccc(SC)cc2)C(=O)NCc2ccc(C(=O)NO)cc2)cc1OC] | $^1$H NMR (DMSO-d$_6$) δ (ppm): 2.4 (3H, s, SMe), 3.68 (3H, s, —OCH$_3$), 3.79 (3H, s, —OMe), 4.35-4.37 (2H, d, —NCH$_2$), 6.70-6.72 (1H, d, —ArH), 6.79 (1H, s, —ArH), 6.97-7.02 (3H, m, —ArH), 7.06-7.08 (2H, d, —ArH), 7.29-7.32 (2H, d, —ArH), 7.44 (1H, s, =CH), 7.68-7.69 (2H, d, —ArH), 7.74-7.77 (1H, t, —NH), 9.00 (1H, s, —NH), 11.16 (1H, s, —OH). MS m/z = 479.0 (m$^+$ + 1) |
| 70 | 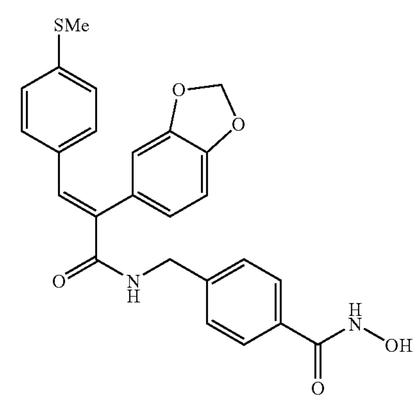 [SMILES: CSc1ccc(/C=C(/C(=O)NCc2ccc(C(=O)NO)cc2)c2ccc3c(c2)OCO3)cc1] | $^1$H NMR (DMSO-d$_6$) δ (ppm): 2.4 (3H, s, —SMe), 4.35-4.37 (2H, d, —NCH$_2$), 6.07 (2H, s, —OCH$_2$), 6.65-6.67 (1H, s, —ArH), 6.77 (1H, s, ArH), 6.96-7.00 (3H, m, —ArH), 7.08-7.10 (2H, d, —ArH), 7.29-7.31 (2H, d, —ArH), 7.43 (1H, s, =CH), 7.67-7.69 (2H, d, —ArH), 7.86 (1H, s, —NH), 8.99 (1H, s, —NH), 11.16 (1H, s, —OH). MS m/z = 463.2 (m$^+$ + 1) |

| S. No | Structure | Analytical Data |
|---|---|---|
| 71 | (structure) | $^1$H NMR (DMSO-d$_6$) δ (ppm): 3.79 (3H, s, —OCH$_3$), 4.37-4.38 (2H, d, —NCH$_2$), 6.99-7.01 (2H, d, —ArH), 7.13-7.15 (2H, d, —ArH), 7.20-7.23 (1H, m, —ArH), 7.29-7.33 (3H, t, —ArH), 7.44 (1H, s, =CH), 7.69-7.71 (2H, d, —ArH), 8.05-8.07 (1H, t, —NH), 8.27 (1H, s, —ArH), 8.35-8.36 (1H, d, ArH), 9.00 (1H, s, —NH), 11.17 (1H, s, —OH). MS m/z = 404.0 (m$^+$ + 1) |
| 72 | (structure) | $^1$H NMR (DMSO-d$_6$) δ (ppm): 4.38-4.39 (2H, d, —NCH$_2$), 7.21-7.27 (6H, m, —ArH), 7.32-7.34 (2H, m, ArH), 7.5 (1H, s, —ArH), 7.68-7.70 (2H, d, —ArH), 8.17-8.19 (1H, t, —NH), 8.27 (1H, s, =CH) 8.37-8.38 (1H, d, —ArH), 9.01 (1H, s, —NH), 11.18 (1H, s, —OH). MS m/z = 392.0 (m$^+$ + 1) |
| 73 | (structure) | $^1$H NMR (DMSO-d$_6$) δ (ppm): 3.79 (3H, s, —OCH$_3$), 4.36-4.37 (2H, d, —NCH$_2$), 6.91-6.95 (2H, m, —ArH), 6.96-7.00 (2H, d, —ArH), 7.12-7.14 (2H, d, —ArH), 7.27-7.33 (3H, d, —ArH), 7.41 (1H, s, =CH), 7.69-7.71 (2H, d, —ArH), 7.97-8.00 (1H, t, —NH), 9.00 (1H, s, —NH), 11.17 (1H, s, —OH). MS m/z = 437.0 (m$^+$ + 1) |
| 74 | (structure) | $^1$H NMR (DMSO-d$_6$) δ (ppm): 2.4 (3H, s, —SMe), 4.36-4.38 (2H, d, —NCH$_2$), 6.89-6.92 (2H, d, —ArH), 7.03-7.05 (2H, d, —ArH), 7.20-7.22 (2H, d, —ArH), 7.30-7.32 (2H, d, —ArH), 7.39-7.46 (4H, m, —ArH), 7.69-7.71 (2H, d, —ArH), 7.94-7.97 (1H, s, —NH), 9.00 (1H, s, —NH), 11.17 (1H, s, —OH). MS m/z = 419.0 (m$^+$ + 1) |

EXAMPLE 75

Synthesis of N-(4-((1E)-3-(hydroxyamino)-3-oxo-prop-1-enyl)benzyl)-2,3-diphenyl acrylamide

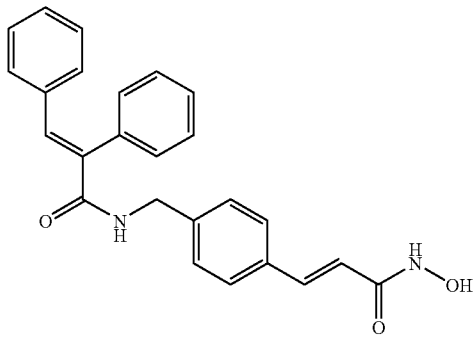 [SMILES: O=C(/C=C/c1ccc(CNC(=O)/C(=C/c2ccccc2)c2ccccc2)cc1)NO]

Step 1

Preparation of ethyl 3(E)-(4-((2,3 diphenylacrylamido)methyl)phenyl)acrylate

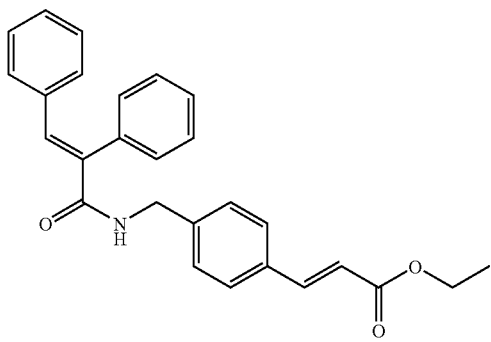 [SMILES: CCOC(=O)/C=C/c1ccc(CNC(=O)/C(=C/c2ccccc2)c2ccccc2)cc1]

To a solution of 2,3-diphenylacrylic acid (0.4 g, 1.3 mmol) (prepared according to procedure given in example 1) in DMF (5 mL) was added ethyl-4-aminomethylphenylacryate-.HCl (0.32 g, 1.3 mmol), EDCI (0.51 g, 2.6 mmol) and HOBt (0.18 g, 1.3 mmol). TEA (0.6 mL, 3.9 mmol) was added dropwise with constant stirring to the above reaction mixture and stirred further for 2 hours at room temperature. Reaction mixture was diluted with water (100 mL), extracted with ethyl acetate (2×100 mL). The combined organic layer was washed successively with water (3×50 mL), and brine solution (1×50 mL). The organic layer was dried over $Na_2SO_4$ and concentrated to afford the crude compound. The crude compound was purified by column chromatography using 1.4% ethylacetate in hexane as an eluent, concentrate the pure fraction to afford the title compound as white solid (0.4 g, 57% yield).

Step 2

Preparation of N-(4-((1E)-3-(hydroxyamino)-3-oxo-prop-1-enyl)benzyl)-2,3-diphenyl acrylamide

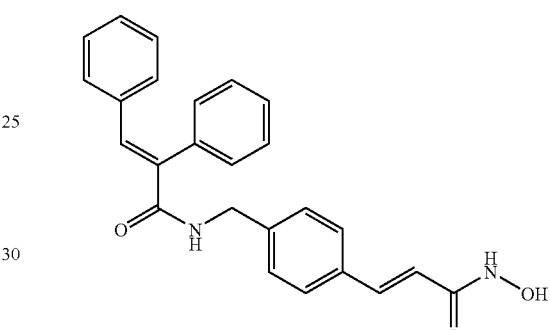

Hydroxylamine hydrochloride (1.2 g, 17.5 mmol) in methanol (7.5 mL) was mixed with KOH (1.2 g, 17.5 mmol) in methanol (4 mL) at 0° C. and the reaction mixture was sonicated for 5 minutes. A white precipitate was formed which was filtered. The filtrate was immediately added to the ethyl-3-(4-((2,3-diphenylacrylamido)methyl)phenyl)acrylate (0.4 g, 0.9 mmol) followed by the addition of KOH. (0.14 g, 2.4 mmol) and the mixture was stirred at room temperature for 1 hour. Reaction mixture was diluted with water 20 mL and extracted with ethyl acetate, (100 mL). The organic layer was washed successively with water (3×50 mL) and brine solution (3×50 mL). The organic layer was dried over $Na_2SO_4$ and concentrated to give the crude compound, triturated with dichloromethane (20 mL), to afford the title compound as a pure colorless solid (0.040 g, 10% yield). $^1H$ NMR (DMSO-$d_6$) δ (ppm): 4.02-4.04 (2H, d, —$CH_2$), 6.41-6.45 (1H, d, =CH), 7.01-7.03 (2H, d, Ar—H), 7.17-7.22 (5H, m, Ar—H), 7.28-7.30 (2H, d, Ar—H), 7.41-7.46 (4H, m, Ar—H & =CH), 7.46 (1H, s, =CH), 7.50-7.52 (2H, d, Ar—H), 7.99-8.01 (1H, t, —NH), 9.03 (1H, s, —OH), 10.74 (1H, s, —NH). MS m/z: 399.1 ($M^+$+1).

The following compounds were prepared according to the above procedure

| S. No | Structure | Analytical Data |
|---|---|---|
| 76 | 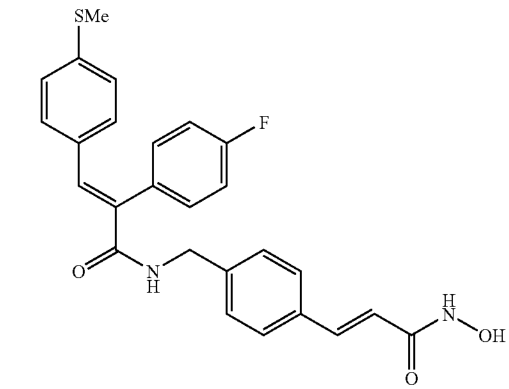 [SMILES: CSc1ccc(/C=C(/C(=O)NCc2ccc(/C=C/C(=O)NO)cc2)c2ccc(F)cc2)cc1] | ¹HNMR (DMSO-d₆) δ (ppm): 2.41 (3H, s, —CH₃), 4.33-4.34 (2H, d, —CH₂), 6.40-6.44 (1H, d, =CH), 6.91-6.93 (2H, d, Ar—H), 7.06-7.08 (2H, d, Ar—H), 7.23-7.29 (6H, m, Ar—H), 7.45-7.51 (4H, m, Ar—H & =CH), 8.00 (1H, t, —NH), 9.0 (1H, s, —OH), 10.6-10.8 (1H, s, —NH). MS m/z: 463.1 (M⁺ + 1). |
| 77 | 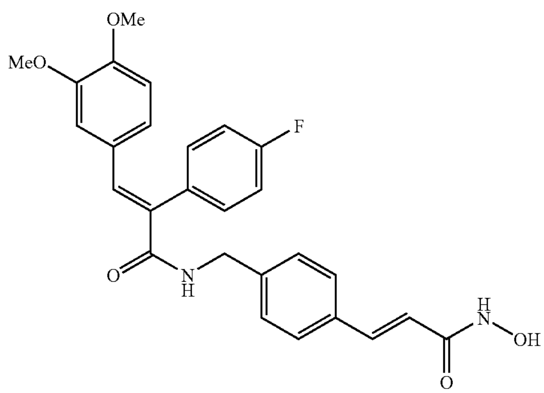 [SMILES: COc1ccc(/C=C(/C(=O)NCc2ccc(/C=C/C(=O)NO)cc2)c2ccc(F)cc2)cc1OC] | ¹HNMR (DMSO-d₆) δ (ppm): 3.39 (3H, s, —OCH₃), 3.71 (3H, s, —OCH₃), 4.34-4.35 (2H, d, —CH₂), 6.41-6.45 (2H, t, Ar—H & =CH), 6.69-6.71 (1H, d, Ar—H), 6.82-6.85 (1H, d, Ar—H), 7.28-7.33 (6H, m, Ar—H), 7.41-7.45 (1H, d, =CH), 7.49-7.52 (3H, t, Ar—H & =CH), 7.88-7.91 (1H, t, —NH), 9.03 (1H, s, —OH), 10.74 (1H, s, —NH). MS m/z: 476.8 (M⁺ + 1). |
| 78 | 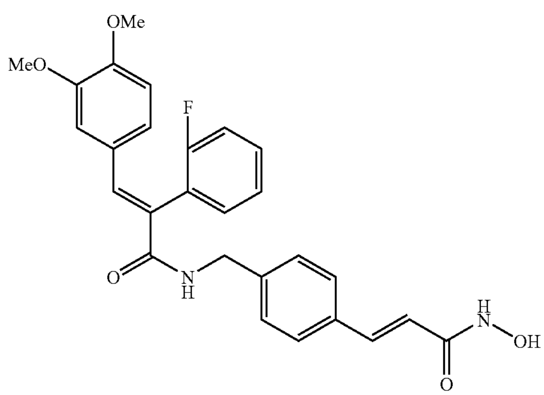 [SMILES: COc1ccc(/C=C(/C(=O)NCc2ccc(/C=C/C(=O)NO)cc2)c2ccccc2F)cc1OC] | ¹HNMR (DMSO-d₆) δ (ppm): 3.35 (3H, s, —OCH₃), 3.71 (3H, s, —OCH₃), 4.35-4.36 (2H, d, —CH₂), 6.41-6.45 (2H, t, Ar—H & =CH), 6.73-6.75 (1H, dd, Ar—H), 6.83-6.86 (1H, d, Ar—H), 7.28-7.32 (5H, m, Ar—H), 7.41-7.45 (1H, d, =CH), 7.48-7.52 (3H, t, Ar—H), 7.59 (1H, s, =CH), 8.10 (1H, t, —NH), 9.04 (1H, s, —OH), 10.74 (1H, s, —NH). MS m/z: 476.8 (M⁺ + 1). |
| 79 | 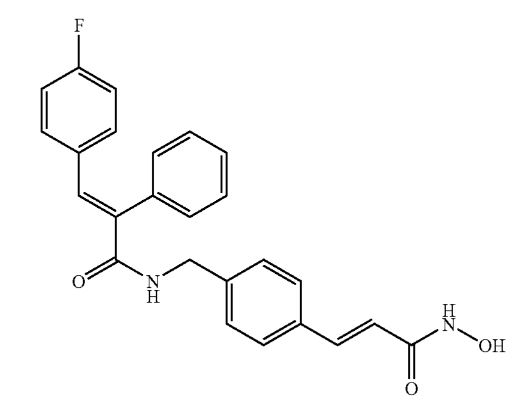 [SMILES: O=C(/C=C/c1ccc(CNC(=O)/C(=C/c2ccc(F)cc2)c2ccccc2)cc1)NO] | ¹HNMR (DMSO-d₆) δ (ppm): 4.35-4.36 (2H, m, —CH₂), 6.41-6.45 (1H, m, Ar—H), 7.01-7.03 (4H, d, Ar—H), 7.20-7.22 (2H, dd, Ar—H), 7.28-7.30 (2H, d, Ar—H), 7.39-7.52 (7H, m, Ar—H & =CH), 7.98-8.01 (1H, t, —NH), 9.03 (1H, m, —OH), 10.74 (1H, s, —NH). M⁺ 1 = 417.1 |

| S. No | Structure | Analytical Data |
|---|---|---|
| 80 | 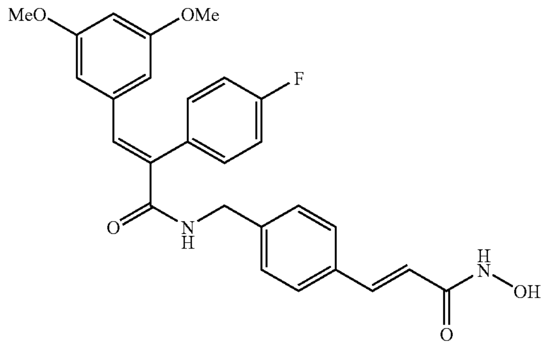 [SMILES: COc1cc(/C=C(/C(=O)NCc2ccc(/C=C/C(=O)NO)cc2)c2ccc(F)cc2)cc(OC)c1] | ¹HNMR (DMSO-d₆) δ (ppm): 3.54 (6H, s, —OCH₃), 4.34-4.35 (2H, d, —CH₂), 6.17-6.18 (2H, d, Ar—H), 6.35-6.36 (1H, t, Ar—H), 6.41-6.45 (1H, d, =CH), 7.24-7.30 (6H, m, Ar—H), 7.41-7.45 (2H, t, Ar—H), 7.50-7.52 (2H, d, Ar—H), 8.04-8.07 (1H, t, —NH), 9.04 (1H, s, —OH), 10.74 (1H, s, —NH). M⁺ 1 = 477.2 |
| 81 | 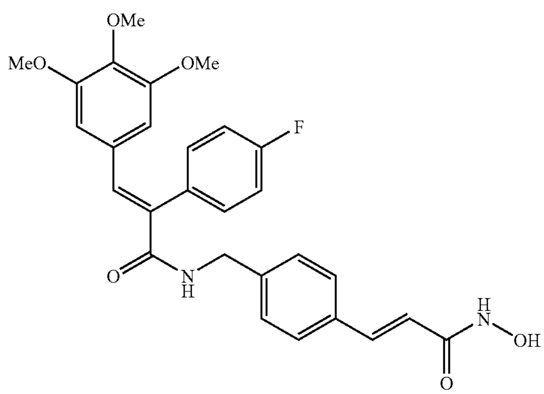 [SMILES: COc1cc(/C=C(/C(=O)NCc2ccc(/C=C/C(=O)NO)cc2)c2ccc(F)cc2)cc(OC)c1OC] | ¹HNMR (DMSO-d₆) δ (ppm): 3.49 (6H, s, —OCH₃), 3.61 (3H, s, —OCH₃), 4.34-4.36 (2H, d, —CH₂), 6.33 (2H, s, Ar—H), 6.40-6.44 (1H, d, =CH), 7.27-7.32 (6H, m, Ar—H), 7.41-7.45 (1H, d, =CH), 7.49-7.52 (2H, m, Ar—H & =CH), 7.93-7.96 (1H, t, —NH), 9.03 (1H, m, —NH), 10.74 (1H, s, —OH). M⁺ 1 = 507.2 |
| 82 | 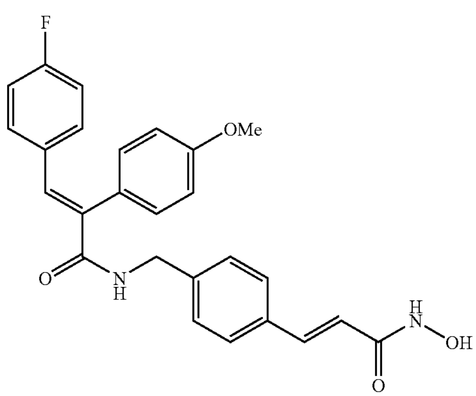 [SMILES: COc1ccc(/C(=C\c2ccc(F)cc2)C(=O)NCc2ccc(/C=C/C(=O)NO)cc2)cc1] | ¹HNMR (DMSO-d₆) δ (ppm): 3.79 (3H, s, —OCH₃), 4.34-4.35 (2H, d, —CH₂), 6.40-6.44 (1H, d, =CH), 6.98-7.00 (2H, d, Ar—H), 7.05-7.07 (3H, m, Ar—H), 7.11-7.13 (2H, d, Ar—H), 7.27-7.29 (2H, d, Ar—H), 7.41-7.51 (4H, m, Ar—H & s = CH), 7.89-7.91 (1H, t, —NH), 9.03 (1H, s, —OH), 10.74 (1H, s, —NH). M⁺ 1 = 447.2 |

EXAMPLE 83

Synthesis of
(2E)-7-(2,3-diphenylacrylamido)-N-hydroxy heptanamide

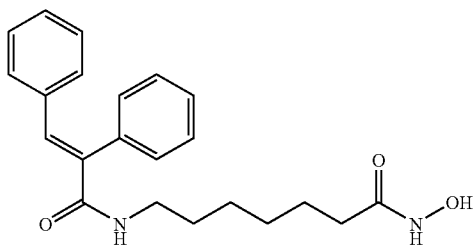 [SMILES: O=C(CCCCCCNC(=O)/C(=C/c1ccccc1)c1ccccc1)NO]

Step 1

Preparation of methyl
(2E)-7-(2,3-diphenylacrylamido)heptanoate

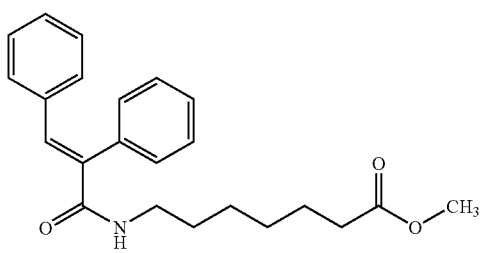 [SMILES: COC(=O)CCCCCCNC(=O)/C(=C/c1ccccc1)c1ccccc1]

To a solution of (2E)-2,3-diphenylacrylic acid (0.32 g, 1.4 mmol) (prepared according to procedure given in example 1) in DMF (5 mL) was added Methyl-7-aminoheptanoate (0.25 g, 1.3 mmol), EDCI (0.55 g, 2.8 mmol) and HOBt (0.19 g, 1.4 mmol). TEA (0.6 mL, 4.3 mmol) was added dropwise with constant stirring to the above reaction mixture and it was stirred for 2 hours at room temperature. Reaction mixture was diluted with water (100 mL), extracted with ethyl acetate (2×100 mL). The organic layer was washed successively with water (3×50 mL), and brine solution (1×50 mL). The organic layer was dried over $Na_2SO_4$ and concentrated to afford the title compound (0.4 g, 61% yield).

Step 2

Preparation of
(2E)-7-(2,3-diphenylacrylamido)-N-hydroxy heptanamide

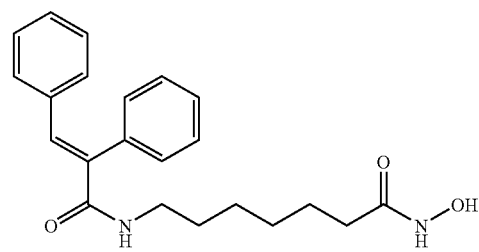 [SMILES: O=C(CCCCCCNC(=O)/C(=C/c1ccccc1)c1ccccc1)NO]

Hydroxylamine hydrochloride (1.4 g, 19.7 mmol) in methanol (3 mL) was mixed with KOH (1.1 g, 19.7 mmol) in methanol (2.5 mL) at 0° C. and the reaction mixture was sonicated for 5 minutes. A white precipitate was formed which was filtered. The filtrate was immediately added to the methyl-(2E)-7-(2,3-diphenylacrylamido)heptanoate (0.4 g, 1.1 mmol) in dichloromethane (1 mL) and the mixture was stirred at room temperature for 30 min. Reaction mixture was diluted with water (20 mL) and extracted with ethyl acetate, (200 mL). The organic layer was washed successively with water (3×50 mL) and brine solution (3×50 mL). The organic layer was dried over $Na_2SO_4$ and concentrated to give the crude compound, triturated with dichloromethane (20 mL), to afford the title compound as a pure colorless solid (0.230g, 58% yield). $^1$H NMR (DMSO-$d_6$) δ (ppm): 1.23 (4H, m, —$CH_2$), 1.42-1.49 (41-1, m, —$CH_2$), 1.91-1.94 (2H, t, —$CH_2$), 3.09-3.14 (2H, q, —$CH_2$), 6.96-6.98 (2H, t, Ar—H), 7.15-7.17 (5H, m, Ar—H), 7.34 (1H, s, =CH), 7.36-7.44 (4H, m, Ar—H & —NH), 9.00 (1H, s, —NH), 10.34 (1H, s, —NH). MS m/z: 367.0 ($M^+$+1).

The following compounds were prepared according to the above procedure

| S. No | Structure | Analytical Data |
|---|---|---|
| 84 | (4-SMe-phenyl)/(4-F-phenyl) acrylamide-N-hexanoyl hydroxamic acid | ¹HNMR (DMSO-d₆) δ (ppm): 1.23 (4H, m, —CH₂), 1.41-1.47 (4H, m, —CH₂), 1.91-1.94 (2H, t, —CH₂), 3.09-3.14 (2H, m, CH₂), 6.90-6.92 (2H, d, Ar—H), 7.06-7.08 (2H, d, Ar—H), 7.19-7.27 (4H, m, Ar—H), 7.34 (1H, s, =CH), 7.45 (1H, s, —NH), 9.02 (1H, s, —NH), 10.35 (1H, s, —NH). MS m/z: 431.0 (M⁺ + 1). |
| 85 | diphenyl acrylamide-N-hexanoyl hydroxamic acid | ¹HNMR (DMSO-d₆) δ (ppm): 1.18 (4H, m, —CH₂), 1.40-1.43 (4H, m, —CH₂), 1.90-1.94 (2H, t, —CH₂), 3.14-3.15 (2H, d, CH₂), 7.03 (1H, s, =CH), 7.27-7.29 (1H, d, Ar—H), 7.31-7.36 (3H, m, Ar—H), 7.39-7.42 (2H, t, Ar—H), 7.50-7.53 (4H, t, Ar—H), 8.40 (1H, s, —NH), 8.69 (1H, s, —OH), 10.36 (1H, s, —NH). MS m/z: 366.9 (M⁺ + 1). |
| 86 | (4-OMe-phenyl)/(4-F-phenyl) acrylamide-N-pentanoyl hydroxamic acid | ¹HNMR (DMSO-d₆) δ (ppm): 1.18-1.23 (2H, m, —CH₂), 1.39-1.49 (4H, m, —CH₂), 1.91-1.95 (2H, t, —CH₂), 3.08-3.12 (2H, m, —CH₂), 3.69 (3H, s, —OCH₃), 6.76-6.78 (2H, d, Ar—H), 6.90-6.93 (2H, d, Ar—H), 7.17-7.27 (4H, m, Ar—H), 7.32-7.36 (2H, m, =CH & —NH), 8.67 (1H, s, —NH), 10.33 (1H, s, —NH). MS m/z: 401.2 (M⁺ + 1). |
| 87 | (4-SO₂Me-phenyl)/(4-F-phenyl) acrylamide-N-pentanoyl hydroxamic acid | ¹HNMR (DMSO-d₆) δ (ppm): 1.23-1.24 (2H, m, —CH₂), 1.42-1.51 (4H, m, —CH₂), 1.92-1.94 (2H, t, —CH₂), 3.13-3.15 (2H, m, —CH₂), 3.33 (3H, s, —CH₃), 7.18-7.26 (6H, m, Ar—H), 7.27 (1H, s, =CH), 7.69-7.75 (2H, m, Ar—H & —NH), 8.67 (1H, s, —NH), 10.33 (1H, s, —NH). MS m/z: 449.1 (M⁺ + 1). |
| 88 | diphenyl acrylamide-N-pentanoyl hydroxamic acid | ¹H NMR (DMSO-d₆) δ (ppm): 1.21-1.23 (2H, m, —CH₂), 1.41-1.50 (4H, m, —CH₂), 1.92-1.95 (2H, t, —CH₂), 3.11-3.13 (2H, m, —CH₂), 6.97-6.99 (2H, d, Ar—H), 7.16-7.17 (4H, m, Ar—H), 7.35 (1H, s, =CH), 7.39-7.42 (4H, m, Ar—H & —NH), 8.67 (1H, s, —OH), 10.34 (1H, s, —NH). MS m/z: 353.2 (M⁺ + 1). |

-continued

| S. No | Structure | Analytical Data |
|---|---|---|
| 89 | 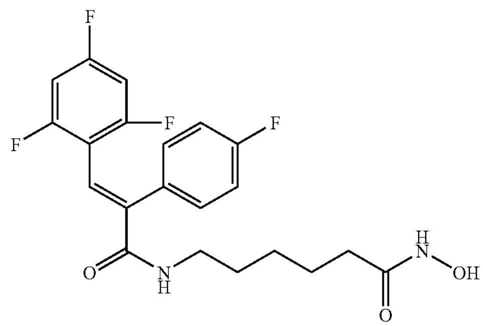 [SMILES: O=C(CCCCCNC(=O)/C(=C/c1c(F)cc(F)cc1F)c1ccc(F)cc1)NO] | $^1$H NMR (DMSO-d$_6$) δ (ppm): 1.23-1.26 (2H, t, —CH$_2$), 1.44-1.51 (4H, m, —CH$_2$), 1.93-1.96 (2H, t, —CH$_2$), 3.13-3.14 (2H, d, —CH$_2$), 6.97 (1H, s, —ArH), 7.05-7.18 (6H, m, ArH), 7.92-7.95 (1H, t, ArH), 7.92-7.95 (1H, t, ArH), 9.02 (1H, s, —OH), 10.36 (1H, s, —NH). MS m/z = 425.1 (M$^+$ + 1). |
| 90 | 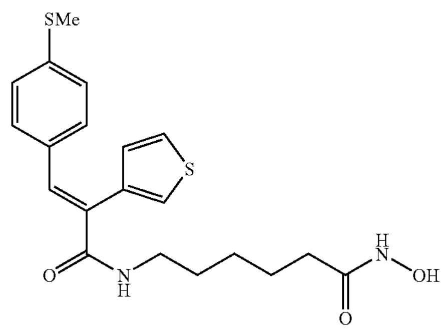 [SMILES: CSc1ccc(/C=C(/C(=O)NCCCCCC(=O)NO)c2ccsc2)cc1] | $^1$H NMR (DMSO-d$_6$) δ (ppm): 1.20-1.22 (2H, t, —CH$_2$), 1.39-1.49 (4H, m, —CH$_2$), 1.91-1.95 (2H, t, —CH$_2$), 2.43 (3H, s, SMe), 3.10-3.12 (2H, t, —CH$_2$), 6.87 (1H, s, —ArH), 6.88-6.95 (2H, d, —ArH), 7.07-7.09 (2H, d, ArH), 7.33 (2H, m, ArH), 7.38 (1H, s, =CH), 7.63-7.64 (1H, t, —NH), 8.68 (1H, s, —OH) 10.34 (1H, s, —NH), MS m/z = 405.1 (M$^+$ + 1). |
| 91 | 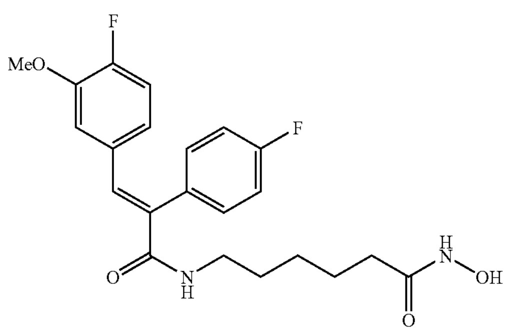 [SMILES: COc1cc(/C=C(/C(=O)NCCCCCC(=O)NO)c2ccc(F)cc2)ccc1F] | $^1$H NMR (DMSO-d$_6$) δ (ppm): 1.21-1.22 (2H, d, —CH$_2$); 1.40-1.50 (4H, m, —CH$_2$); 1.92-1.95 (2H, t, —CH$_2$); 3.10-3.12 (2H, d, —CH$_2$); 3.51 (3H, s, —OMe); 6.64-6.69 (2H, m, —ArH); 7.08 (1H, s, =CH); 7.19-7.28 (4H, m, ArH); 7.49 (2H, s, ArH); 8.70 (1H, s, —OH) 10.36 (1H, s, —NH), MS m/z = 419.4 (M$^+$ + 1). |
| 92 | 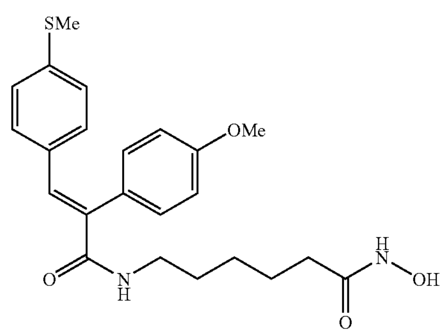 [SMILES: COc1ccc(/C(=C\c2ccc(SC)cc2)C(=O)NCCCCCC(=O)NO)cc1] | $^1$H NMR (DMSO-d$_6$) δ (ppm): 1.19-1.24 (2H, t, —CH$_2$), 1.39-1.49 (4H, m, —CH$_2$), 1.91-1.95 (2H, t, —CH$_2$), 2.41 (3H, s, —SMe), 3.09-3.10 (2H, t, —CH$_2$), 3.79 (3H, s, —OMe), 6.93-6.99 (2H, m, —ArH), 7.04-7.08 (2H, t, —ArH), 7.25-7.26 (4H, d, ArH), 7.29 (2H, s, ArH), 8.68 (1H, s, —OH) 10.34 (1H, s, —NH), MS m/z = 428.5 (M$^+$ + 1). |
| 93 | 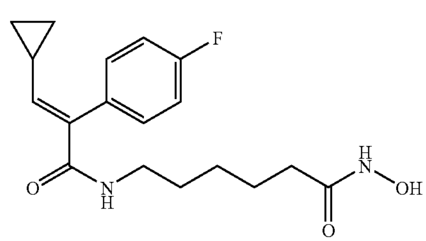 [SMILES: O=C(CCCCCNC(=O)/C(=C/C1CC1)c1ccc(F)cc1)NO] | $^1$H NMR (DMSO-d$_6$) δ (ppm): 0.59-0.60 (2H, t, —CH$_2$), 0.80-0.82 (2H, t, —CH$_2$), 1.18-1.91 (9H, m, —CH$_2$), 3.05-3.06 (2H, d, —CH2), 5.89-5.92 (1H, m, —CH), 7.20-7.25 (5H, m, —ArH), 8.69 (1H, s, —OH), 10.34 (1H, s, —NH), MS m/z = 334.4 (M$^+$ + 1). |

-continued

| S. No | Structure | Analytical Data |
|---|---|---|
| 94 | 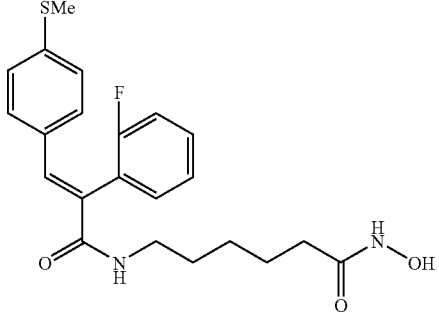 [SMILES: CSc1ccc(/C=C(/C(=O)NCCCCCC(=O)NO)c2ccccc2F)cc1] | $^1$H NMR (DMSO-$d_6$) δ (ppm): 1.22-1.23 (4H, t, —CH$_2$), 1.41-1.49 (4H, m, —CH$_2$), 1.91-1.94 (2H, t, —CH$_2$), 2.42 (3H, s, —SMe), 3.10-3.13 (2H, t, —CH$_2$), 6.92-6.94 (2H, d, —ArH), 7.07-7.08 (2H, d, —ArH), 7.16-7.18 (1H, d, —ArH), 7.21-7.28 (2H, m, ArH), 7.45-7.47 (2H, d, —ArH), 7.63 (1H, s, =CH), 8.69 (1H, s, —OH) 10.36 (1H, s, —NH), MS m/z = 416.5 (M$^+$ + 1). |
| 95 | 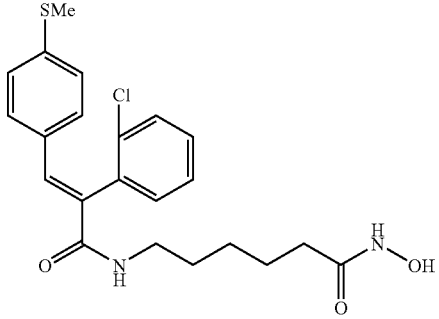 | $^1$HNMR (DMSO-$d_6$) δ (ppm): 1.19-1.22 (2H, t, —CH$_2$); 1.39-1.49 (4H, m, —CH$_2$); 1.90-1.94 (2H, t, —CH2); 2.40 (3H, s, —CH3); 3.10 (2H, s, —CH2); 6.85-6.87 (2H, d, —ArH); 7.04-7.06 (2H, d, —ArH); 7.15-7.18 (1H, m, —ArH); 7.37-7.39 (1H, d, —ArH); 7.43-7.46 (2H, m, —ArH); 7.49 (1H, s, =CH); 7.56-7.58 (1H, t, —NH), 8.67 (1H, s, —OH); 10.34 (1H, s, —NH). (MS m/z = 432.9 M$^+$ + 1) |
| 96 | 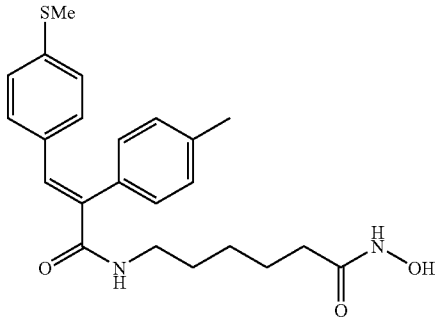 [SMILES: CSc1ccc(/C=C(/C(=O)NCCCCCC(=O)NO)c2ccc(C)cc2)cc1] | $^1$HNMR (DMSO-$d_6$) δ (ppm): 1.19-1.21 (2H, t, —CH$_2$); 1.38-1.49 (4H, m, —CH$_2$); 1.90-1.94 (2H, t, —CH2); 2.35 (3H, s, —CH3); 2.41 (3H, s, —SCH3); 3.08-3.11 (2H, t, —CH2); 6.91-6.93 (2H, d, —ArH); 6.98-7.05 (4H, m, —ArH); 7.22-7.26 (3H, m, —ArH & =CH); 7.30 (1H, t, —NH), 8.68 (1H, s, —OH); 10.34 (1H, s, —NH). (MS m/z = 413.1 (M$^+$ + 1) |

EXAMPLE 98

Synthesis of N-(2-aminophenyl)-6-(2-(4-fluorophenyl)-3-(4-methylthio phenyl)acrylamido) hexanamide

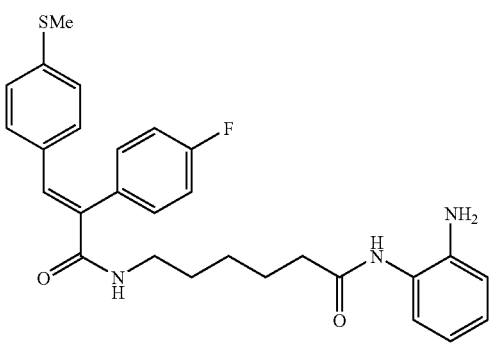 [SMILES: CSc1ccc(/C=C(/C(=O)NCCCCCC(=O)Nc2ccccc2N)c2ccc(F)cc2)cc1]

Step 1

Preparation of 6-(2-(4-fluorophenyl)-3-(4-methylthiophenyl)acrylamido)hexanoic acid

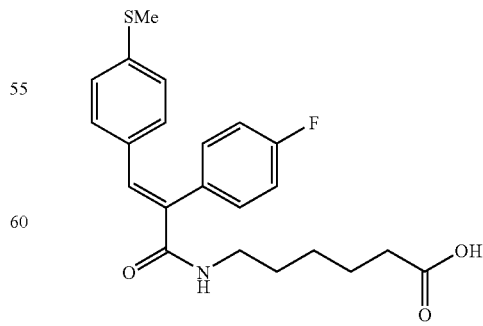

To a solution of methyl-6-(2-(4-fluorophenyl)-3-(4-methylthiophenyl)acrylamido) hexanoate (0.8 g, 2 mmol) in methanol (10 mL) was added, a solution of NaOH (0.24 g, 6 mmol) in water (1 mL). The reaction mixture was refluxed for two hours at 70° C. The solvent was removed by evaporation, poured to ice cold water. The aqueous layer was acidified (pH 3) with dilute HCl and allowed to stand at 4° C. for 30 min., the solid precipitated out was filtered and dried under vacuum to give a pale yellow solid (0.7 g, 90% yield).

| S. No | Structure | Analytical Data |
|---|---|---|
| 97 | 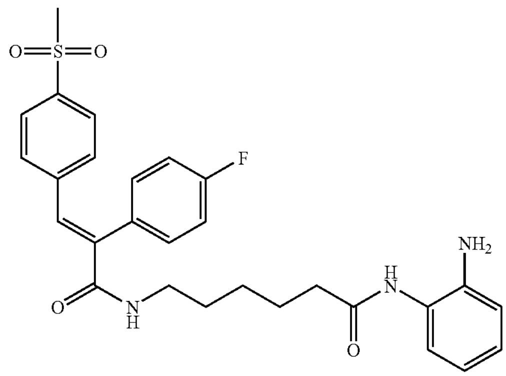 | $^1$H NMR (DMSO-$d_6$) δ (ppm): 1.29-1.33 (2H, m, —CH$_2$), 1.48-1.51 (2H, m, —CH$_2$), 1.58-1.62 (2H, m, —CH$_2$), 2.30-2.33 (2H, t, —CH$_2$), 3.13-3.18 (5H, t, —CH$_2$ & —CH$_3$), 4.81 (2H, s, —NH$_2$), 6.50-6.54 (1H, m, Ar—H), 6.70-6.72 (1H, m, Ar—H), 6.86-6.88 (1H, m, Ar—H), 7.15-7.17 (1H, m, Ar—H), 7.20-7.25 (6H, m, Ar—H), 7.42 (1H, s, =CH), 7.71-7.75 (3H, m, Ar—H & —NH), 9.08 (1H, s, —NH). MS m/z: 524.1 (M$^+$ + 1). |

Step-2

Preparation of N-(2-aminophenyl)-6-(2-(4-fluorophenyl)-3-(4-methylthio phenyl)acrylamido) hexanamide

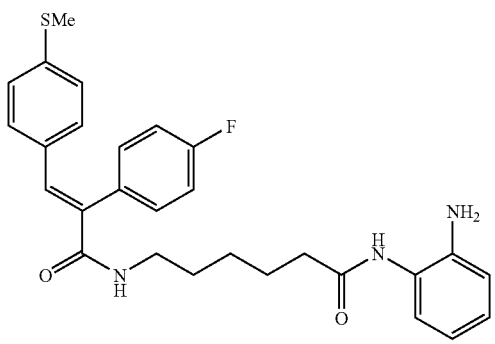 [SMILES: CSc1ccc(/C=C(/C(=O)NCCCCCC(=O)Nc2ccccc2N)c2ccc(F)cc2)cc1]

To a suspension of 6-(2-(4-fluorophenyl)-3-(4-methylthiophenyl)acryl amido)hexanoic acid (0.5 g, 1.24 mmol) in DMF (3 mL) was added EDCI (0.425 g, 2.2 mmol), HOBt (0.1 g, 0.74 mmol), o-phenylenediamine (0.107 g, 1 mmol), followed by TEA (0.52 mL, 3.7 mmol). The reaction mixture was stirred for 1 h after which the mixture was added to cold water (100 mL) and kept at 0° C. for 1 h. The solid formed was filtered and washed with water (50 mL), dried under vacuum to afford the title compound as white solid (0.260 g, 42% yield). $^1$H NMR (DMSO-$d_6$) δ (ppm): 1.29-1.31 (2H, m, —CH$_2$), 1.45-1.46 (2H, m, —CH$_2$), 1.57-1.60 (2H, m, —CH$_2$), 2.28-2.32 (2H, t, —CH$_2$), 2.41 (3H, s, —CH$_3$) 3.12-3.14 (2H, t, —CH$_2$), 4.80 (2H, s, —NH$_2$), 6.52 (1H, m, Ar—H), 6.69-6.71 (1H, m, Ar—H), 6.89-6.91 (1H, m, Ar—H), 7.05-7.07 (2H, m, Ar—H), 7.13-7.16 (2H, m, Ar—H), 7.18 (2H, m, Ar—H), 7.20 (2H, m, Ar—H), 7.23 (1H, m, Ar—H), 7.34 (1H, s, =CH), 7.46 (1H, s, —NH), 9.08 (1H, s, —NH). MS m/z: 492.1 (M$^+$+1).

The following compound was prepared according to the above procedure

EXAMPLE 99

Synthesis of 6-(3-(2-(4-fluorophenyl)-3-(4-methylthiophenyl)acryloyl)ureido)-N-hydroxy hexanamide

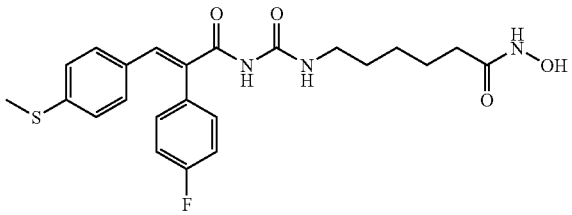 [SMILES: CSc1ccc(/C=C(/C(=O)NC(=O)NCCCCCC(=O)NO)c2ccc(F)cc2)cc1]

Step 1

Preparation of 2-(4-fluorophenyl)-3-(4-methylthiophenyl)acrylamide

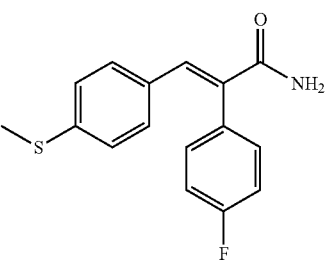 [SMILES: CSc1ccc(/C=C(/C(N)=O)c2ccc(F)cc2)cc1]

To a mixture 2-(4-fluorophenyl)-3-(4-methylthiophenyl) acrylic acid (prepared according to procedure given in Example 1) (3 g, 10.4 mmol), EDCI (4 g, 20.8 mmol), HOBt (1.4 g, 10.4 mmol) in DMF (35 mL) and triethylamine (3 mL, 20.8 mmol) was added slowly and stirred for 30 min. Reaction mixture was cooled to 5° C. and anhydrous ammonia gas purged for 10 min and stirred at 30° C. for 30 min. Reaction mixture was poured into water (250 mL) and extracted with ethyl acetate (2×200 mL). Combined organic layer was successively washed with water (3×200 mL) and brine solution (1×150 mL), dried over anhydrous sodium sulfate (2 g) and concentrated to afford the crude compound. The crude compound was triturated with hexane:ethyl acetate (9:1) (40 mL) for 3 times to afford a title compound as colorless solid (2 g, 67% yield).

Step 2

Preparation of Methyl-6-(3-(2-(4-fluorophenyl)-3-(4-methylthiophenyl)aeryloyl)ureido)-hexanoate

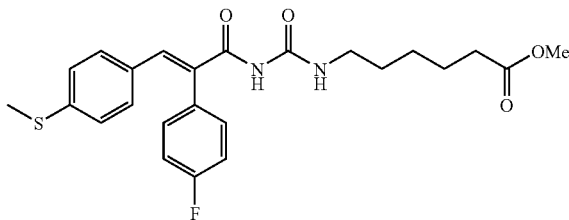 [SMILES: COC(=O)CCCCCNC(=O)NC(=O)/C(=C/c1ccc(SC)cc1)c1ccc(F)cc1]

A solution of 2-(4-fluorophenyl)-3-(4-methylthiophenyl) acrylamide (1.2 g, 4.2 mmol) in 1,2-dichloroethane (15 mL) was cooled to 5° C. then oxalyl chloride (0.45 ml, 5.0 mmol) was added drop wise under stirring and it was refluxed at 90° C. for 2 hours. Reaction mixture was cooled to 30° C. Mixture of methyl 6-aminohexanoate.HCl (0.85 g, 4.6 mmol) and triethylamine (1.7 mL, 12.5 mmol) in MDC (15 mL) was added to the above reaction mixture under stirring at 5° C. and stirred for 1 hour. Reaction mixture was diluted with ethylacetate (150 mL), filtered the solid and filtrate was washed with water (2×100 mL). Ethylacetate layer was evaporated to dryness to obtain solid compound and was triturated with hexane:ethylacetate (6:4) filtered and dried under vacuum to afford the title compound (1.5 g, 79%).

Step 3

Preparation of 6-(3-(2-(4-fluorophenyl)-3-(4-methylthiophenyl)acryoyl)ureido)-N-hydroxy hexanamide

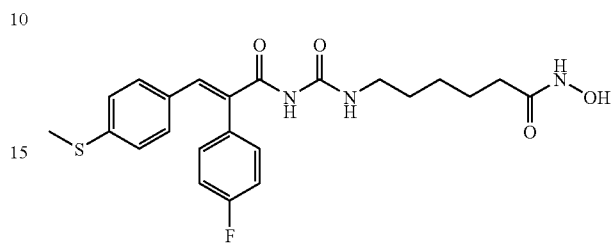

Hydroxylamine hydrochloride (1 g, 19.7 mmol) in methanol (3 mL) was mixed with KOH (1.1 g, 19.7 mmol) in methanol (2.5 mL) at 0° C. and the reaction mixture was sonicated for 5 minutes. A white precipitate was formed which was filtered. The filtrate was immediately added to the methyl-6-(3-(2-(4-fluorophenyl)-3-(4-methylthiophenyl)acryoyl)ureido)-hexanoate (0.4 g, 1.1 mmol) in dichloromethane (1 mL) and the mixture was stirred at room temperature for 1 hour. Reaction mixture was diluted with water 20 mL and extract with ethylacetate, (200 mL) washed with water (50 mL) and brine solution (50 mL). The organic layer was dried over $Na_2SO_4$ and concentrated to give the crude compound. The crude compound was purified by flash chromatography using 4% MeOH:DCM as an eluent, concentrated pure fraction under vacuum to afford the title compound as a pure colorless solid (0.230 g, 58% yield). NMR (DMSO-$d_6$) δ (ppm): 1.24-1.28 (2H, m, —$CH_2$), 1.44-1.51 (4H, m, —$CH_2$), 1.92-1.96 (2H, t, —$CH_2$), 2.43 (3H, s, —$CH_3$), 3.16-3.19 (2H, m, —$CH_2$), 6:95=6.97 (2H, d, Ar—H), 7.09-7.11 (2H, d, Ar—H), 7.24-7.28 (4H, m. Ar—H), 7.53 (1H, s, =CH), 8.46-8.48 (1H, t, —NH), 8.66 (1H, s, —OH), 9.96 (1H, s, —NH), 10.33 (1H, s, —NH). MS m/z: 460.1 ($M^+$+1).

The following compounds were prepared according to the above procedure

| S. No | Structure | Analytical Data |
|---|---|---|
| 100 | 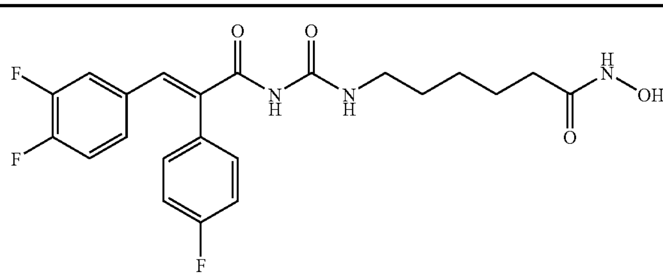 | $^1$HNMR (DMSO-$d_6$) δ (ppm): 1.23 (2H, m, —$CH_2$), 1.45-1.49 (4H, m, —$CH_2$), 1.92-1.95 (2H, t, —$CH_2$), 3.16-3.17 (2H, d, —$CH_2$), 6.89-7.02 (2H, m, Ar—H), 7.24-7.38 (5H, m, Ar—H), 7.49 (1H, s, =CH), 8.40-8.42 (1H, d, —NH), 8.66 (1H, s, —OH), 10.17 (1H, s, —NH), 10.33 (1H, s, —NH). MS m/z: 450.1 ($M^+$ + 1). |
| 101 | 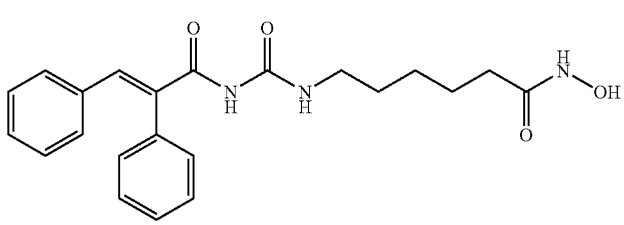 [SMILES: O=C(CCCCCNC(=O)NC(=O)/C(=C/c1ccccc1)c1ccccc1)NO] | $^1$HNMR (DMSO-$d_6$) δ (ppm): 1.24-1.26 (2H, m, —$CH_2$), 1.46-1.51 (4H, m, —$CH_2$), 1.91-1.94 (2H, t, —$CH_2$), 3.16-3.17 (2H, d, —$CH_2$), 7.03-7.05 (2H, d, Ar—H), 7.20-7.22 (5H, m, Ar—H), 7.40-7.42 (3H, t, Ar—H), 7.52 (1H, s, =CH), 8.46 (1H, t, —NH), 8.66 (1H, s, —OH), 9.89 (1H, s, —NH), 10.33 (1H, s, —NH). MS m/z: 396.2 ($M^+$ + 1). |

EXAMPLE 102

Synthesis of 3-(3,4-dimethoxyphenyl)-2-(4-methoxyphenyl)allyl-4(2-aminophenylcabamoyl)benzylcarbamate

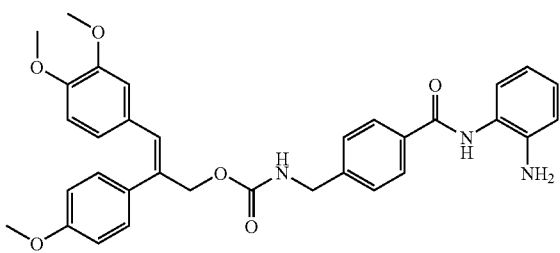 [SMILES: COc1ccc(/C(=C\c2ccc(OC)c(OC)c2)COC(=O)NCc2ccc(C(=O)Nc3ccccc3N)cc2)cc1]

Step 1

Synthesis of methyl 3-(3,4-dimethoxyphenyl)-2-(4-methoxyphenyl)prop-2-enoate

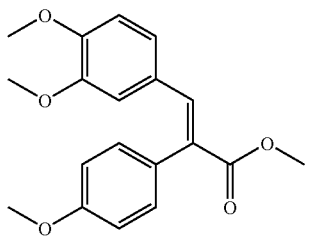

3-(3,4-dimethoxyphenyl)-2-(4-methoxyphenyl)prop-2-enoic acid (2 g, 6.37 mmol) was dissolved in dimethyl formamide (DMF) (4 mL) and added potassium carbonate ($K_2CO_3$) (2.28 g, 16.6 mmol) followed by methyl iodide ($CH_3I$) (0.48 mL, 7.64 mmol) drop wise. The reaction mixture was stirred for 2 hours at room temperature (RT) and the reaction was monitored by TLC. Upon the completion of reaction, $K_2CO_3$ was filtered and cold water (100 mL) was added to the filtrate. The resulting precipitate was filtered to get pale yellow solid (2 g, 100%).

Step 2

Synthesis of 3-(3,4-dimethoxyphenyl)-2-(4-methoxyphenyl)prop-2-en-1-ol

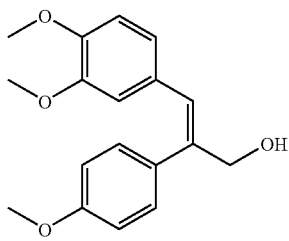 [SMILES: COc1ccc(/C(=C\c2ccc(OC)c(OC)c2)CO)cc1]

In a 100 mL round bottom flask lithium aluminium hydride WAIN (0.28 g, 7.2 mmol) in tetrahydrofuran (THF) was taken and cooled to 0-5° C., to which methyl-3-(3,4-dimethoxyphenyl)-2-(4-methoxyphenyl)prop-2-enoate (2 g, 6.09 mmol) dissolved in THF (15 mL) was added drop wise using dropping funnel. The reaction mixture was stirred for 1 hour at same temperature and the reaction was monitored by TLC. Upon the completion of reaction, added ethyl acetate (50 mL) drop wise followed by cold water (50 mL). The organic layer was separated and the aqueous layer further extracted with ethyl acetate (50 mL). The combined organic layer was washed with brine, dried over anhydrous $Na_2SO_4$ and concentrated under reduced pressure to give pure compound (1 g, 55%).

Step 3

Synthesis of 3-(3,4-dimethoxyphenyl)-2-(4-methoxyphenyl)allyl-4(2-aminophenylcabamoyl)benzylcarbamate

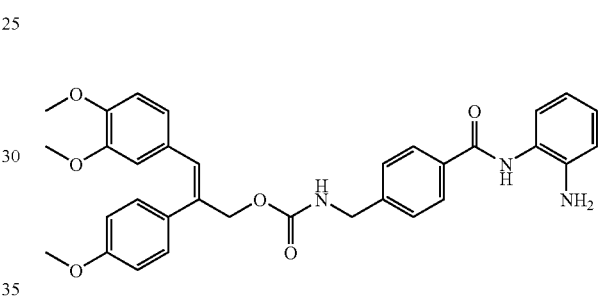

To a solution of 3-(3,4-dimethoxyphenyl)-2-(4-methoxyphenyl)prop-2-en-1-ol (0.5 g, 1.66 mmol) in THF (10 mL), carbodiimidazole (0.27 g, 1.66 mmol) was added slowly under cooling condition. After stirring the reaction mixture for 3 hours at room temperature (RT) pre-stirred mixture of 4-(aminomethyl)-N-(2-aminophenyl)benzamide (0.4 g, 1.66 mmol) in THF (10 mL) and triethylamine ($Et_3N$) (0.2 mL, 1.66 mmol) was added for 15 minutes at RT and the reaction was monitored by TLC. On completion of the reaction cold water (50 mL) was added and extracted with ethylacetate (2×50 mL). The combined organic layer was washed with brine, dried over anhydrous $Na_2SO_4$ and concentrated under reduced pressure. The resulting crude extract was purified by basic alumina column chromatography (80% ethyl acetate/hexane) to give a pure colourless solid (0.2 g, 22%). NMR (DMSO-$d_6$) δ (ppm): 3.38 (3H, s, —OCH$_3$), 3.67 (3H, s, —OCH$_3$), 3.75 (3H, s, —OCH$_3$), 4.23-4.24 (2H, d, —NCH$_2$), 4.81 (2H, s, —OCH$_2$), 4.89 (2H, s, —NH$_2$), 6.47 (1H, S, —ArH), 6.59-6.61 (3H, d, Ar—H), 6.76-6.78 (2H, m, Ar—H), 6.94-6.96 (1H, s, Ar—H), 7.16-7.18 (4H, m, —ArH), 7.30-7.32 (3H, m, ArH), 7.90-7.92 (3H, m, ArH and —NH) 9.62 (1H, s, —NH) MS m/z: 567.8 (M$^+$+1).

103 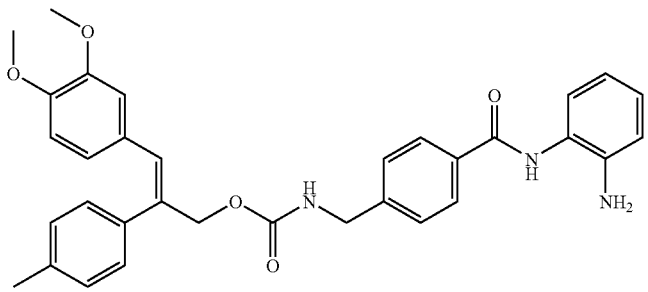 [SMILES: COc1ccc(/C=C(/COC(=O)NCc2ccc(C(=O)Nc3ccccc3N)cc2)c2ccc(C)cc2)cc1OC]

$^1$H NMR (DMSO-$d_6$) δ (ppm): 2.32 (3H, s, —CH$_3$), 3.33-3.35 (3H, s, —OCH$_3$), 3.68 (3H, s, —OCH$_3$), 4.23-4.24 (2H, d, —NCH$_2$), 4.82 (2H, s, —OCH$_2$), 4.89 (2H, s, —NH$_2$), 6.44 (1H, s, ArH), 6.59-6.62 (3H, d, —ArH), 6.75-6.79 (2H, m, —ArH), 6.97 (1H, s, =CH), 7.12-7.32 (7H, m, —ArH), 7.84-7.92 (3H, m, —ArH), 9.62 (1H, s, —NH).
MS m/z = 551.8 (m$^+$ + 1)

Anti-cancer Experimental Methods

Anti-cancer Screen:

Experimental drugs were screened for anti-cancer activity in three cell lines using five concentrations for each compound. The cell lines —HCT 116 (colon), NCIH460 (lung) and U251 (glioma) were maintained in DMEM containing 10% fetal bovine serum. 96-well microtiter plates are inoculated with cells in 100 μL of cell suspension (5×10$^4$ cells/mL) for 24 hours at 37° C., 5% CO$_2$, 95% air and 100% relative humidity. A separate plate with these cell lines is also inoculated to determine cell viability before the addition of the compounds (T$_0$).

Addition of Experimental Drugs:

Following 24-hours incubation, test compounds were added to the 96 well plates. Each plate contains one of the above cell lines and the following samples in triplicate: five different dilutions (0.01, 0.1, 1, 10 and 100 μM) of four test compounds, appropriate dilutions of a cytotoxic standard and growth medium (untreated) wells. Test compounds were dissolved in DMSO to prepare 20 mM stock solutions on the day of drug addition and serial dilutions were carried out in complete growth medium at 2× strength such that 100 μL added to wells gave final concentrations (0.01, 0.1, 1, 10 and 100 μM) in the well. SAHA was used as standard drug in these experiments.

End-point Measurement:

For T$_0$ measurement, 24 hours after seeding the cells, 20 μL of 3-(4,5-dimethyl-2-thiazolyl)-2,5-diphenyl-2H-tetrazolium (MTT) solution per well was added to the 'T$_0$' plate and incubated for 3 hours at 37° C. in a CO$_2$ incubator. The plate containing cells and test compounds was treated similarly after 48 hours of incubation. After 3 hours of MTT addition, well contents were aspirated carefully followed by addition of 150 μL DMSO per well. Plates were agitated to ensure dissolution of the formazan crystals in DMSO and absorbance was read at 570 nm (A$_{570}$).

Calculation of G$_1$, TG$_1$ and LC$_{50}$:

Percent growth (PG) is calculated relative to the control and zero measurement wells (T$_0$) as follows:

PG=(A$_{570}$test−A$_{570}$T$_0$)/(A$_{570}$control−A$_{570}$T$_0$)×100 (If A$_{570}$ test>A$_{570}$T$_0$)

PG=(A$_{570}$test−A$_{570}$T$_0$)/(A$_{570}$T$_0$)×100 (If A$_{570}$ test<A$_{570}$T$_0$), PG values are plotted against drug concentration to derive the following: GI$_{50}$ is the concentration required to decrease PG by 50% vs control; TGI is the concentration required to decrease PG by 100% vs control and LC$_{50}$ is the concentration required to decrease PG by 50% vs T$_0$. (Mosmann T. Rapid colorimetric assay for cellular growth and survival: application to proliferation and cytotoxicity assays. *J Immunol Methods* 1983; 65(1-2): 55-63; Anne Monks et al. Feasibility of high-flux anticancer drug screen using a diverse panel of cultured human tumor cell lines". *JNCI*, Vol. 83, No. 11, 1991). Results for growth inhibition of the synthesized compounds are given in Table-1.

HDAC Activity screening:

Histone Deacetylase (HDAC) Inhibition Assay using Boc-Lys (Ac)-AMC Substrate: Inhibition of HDAC has been implicated to modulate transcription and to induce apoptosis or differentiation in cancer cells. The fluorometric assay provides a fast and fluorescence based method that eliminates radioactivity, extractions or chromatography, as used in traditional assays. The assay is based on two steps. First, the HDAC fluorometric substrate, which comprises an acetylated lysine side chain, is incubated with a sample containing HDAC activity (Mouse Liver Extract). Deacetylation of the substrate sensitizes the substrate, in the second step; treatment with the Trypsin stop solution produces a fluorophore that can be easily analyzed using fluorescence plate reader.

Assay was done in 96-well black microplate and total volume of the assay was 100 pt. Mouse liver enzyme (10 mg/ml) was diluted 1:6 with HDAC buffer. Enzyme cocktail was made of 10 μL of diluted enzyme and 30 μL of HDAC buffer. 40 μl of enzyme cocktail followed by 10 μL of test compound (1 μM and 10 μM) or buffer (control) was added to each well. The plate was pre-incubated at 37° C. for 5 minutes. The HDAC reaction was started by adding 50 μl of HDAC substrate Boc-Lys (Ac)-AMC (Bachem AG, Switzerland). The plate was incubated at 37° C. for 30 min. The reaction was stopped by adding 100 μL, of Trypsin stop solution and incubating at 37° C. for 15-30 min. Measuring the fluorescence at excitation wavelength of 360 nm and emission wavelength of 460 nm monitored the release of AMC. Buffer alone and substrate alone served as blank. For selected compounds, IC$_{50}$ (50% HDAC inhibitory concentration) was determined by testing in a broad concentration range of 0.001, 0.01, 0.1, 1 and 10 μM. (Dennis Wegener et al, *Anal. Biochem*, 321, 2003, 202-208).

Results for HDAC inhibition at 1 and 10 μM and IC$_{50}$ values aret tabulated in Table-1.

TABLE 1

Inhibition of cancer cell growth and HDAC enzyme activity

| Test Compound | NCIH460 (Lung) | | | HCT116 (Colon) | | | U251 (Glioma) | | | Mean GI$_{50}$ | HDAC inhibition % (1 µM) | % (10 µM) | IC$_{50}$ (µM) |
|---|---|---|---|---|---|---|---|---|---|---|---|---|---|
| | GI$_{50}$ | TGI | LC$_{50}$ | GI$_{50}$ | TGI | LC$_{50}$ | GI$_{50}$ | TGI | LC$_{50}$ | | | | |
| 1 | 2.3 | 5.4 | 52.0 | 2.2 | 4.9 | 27.0 | 2.8 | 4.2 | 35.0 | 2.4 | 1.2 | 27.8 | — |
| 2 | 2.9 | 8.2 | >100 | 4.4 | 9.4 | >100 | 7.6 | 39.0 | >100 | 5.0 | 2.3 | 6.8 | — |
| 3 | 0.6 | 52.0 | >100 | 3.2 | 10.0 | 100.0 | 16.0 | 39.0 | 85.0 | 6.6 | 5.1 | 16.4 | — |
| 4 | 0.2 | 3.8 | 58.5 | 4.1 | 26.0 | 77.0 | 11.5 | 41.0 | >100 | 5.3 | 0.0 | 14.2 | — |
| 5 | 5.5 | >100 | >100 | 3.1 | 11.0 | >100 | — | — | — | 4.3 | 0.0 | −27.4 | — |
| 6 | 8.8 | 47.0 | 90.0 | 4.8 | 46.0 | 95.8 | <0.01 | 22.0 | 83.2 | 4.5 | 4.2 | 25.8 | — |
| 7 | 6.2 | 26.5 | 73.8 | 4.5 | 9.6 | 71.2 | 17.0 | 34.5 | 76.0 | 9.2 | 12.4 | 19.4 | — |
| 8 | 89.0 | >100 | >100 | 24.5 | 82.5 | >100 | 67.0 | 84.5 | >100 | 60.2 | 21.4 | 26.4 | — |
| 9 | 90.0 | >100 | >100 | 58.0 | 94.0 | >100 | 60.0 | 79.0 | >100 | 69.3 | 12.1 | 32.1 | — |
| 10 | 19.5 | 49.0 | 85.0 | 3.9 | 9.0 | 56.0 | 27.0 | 57.0 | 92.0 | 16.8 | 14.5 | 32.1 | — |
| 11 | 8.0 | 41.2 | 83.0 | 5.0 | 12.5 | 68.5 | 26.1 | 53.0 | 86.0 | 13.0 | 9.7 | 24.6 | — |
| 12 | 32.0 | 60.0 | 87.0 | 5.2 | 37.0 | 76.2 | 18.0 | 48.5 | 82.0 | 18.4 | 13.6 | 29.8 | — |
| 13 | 34.0 | 66.0 | 93.0 | 8.9 | 50.0 | 90.0 | 3.4 | 8.0 | 48.0 | 15.4 | 9.4 | 18.2 | — |
| 14 | 8.0 | 49.0 | 82.0 | 5.6 | 24.0 | 81.0 | — | — | — | 6.8 | 22.8 | 31.6 | — |
| 15 | 8.8 | 60.0 | 95.0 | 2.7 | 30.0 | 94.0 | — | — | — | 5.8 | 42.7 | 56.9 | 3.8 |
| 16 | 45.0 | 97.0 | >100 | 40.0 | 82.0 | >100 | — | — | — | 42.5 | 30.7 | 46.0 | — |
| 17 | 38.0 | 80.0 | >100 | 29.0 | 69.0 | >100 | — | — | — | 33.5 | 25.7 | 20.3 | — |
| 18 | 4.1 | 20.0 | >100 | 5.0 | 20.0 | >100 | 2.2 | 4.0 | 7.0 | 3.8 | 28.7 | 36.7 | — |
| 19 | 2.5 | 8.0 | 70.0 | 0.3 | 5.0 | 58.0 | 0.3 | 1.8 | 4.8 | 1.0 | 29.7 | 52.9 | 8.6 |
| 20 | 7.5 | 18.0 | 80.0 | 0.3 | 20.0 | 80.0 | 1.7 | 3.5 | 7.1 | 3.2 | 45.1 | 46.2 | 19.0 |
| 21 | 32.0 | 46.0 | 78.0 | 35.0 | 56.0 | 82.0 | 52.0 | 65.0 | 96.0 | 39.7 | 7.0 | 24.8 | — |
| 22 | 7.6 | 80.0 | >100 | 7.9 | 70.0 | >100 | — | — | — | 7.8 | 32.9 | 56.1 | 3.2 |
| 23 | 34.0 | >100 | >100 | 4.0 | 8.0 | 98.0 | >100 | >100 | >100 | 19.0 | 41.1 | 57.0 | — |
| 24 | 5.0 | 32.0 | >100 | 3.8 | 12.0 | >100 | 8.5 | 30.0 | >100 | 5.8 | 41.3 | 51.4 | 82 |
| 25 | 19.0 | 58.0 | 100.0 | 7.5 | 48.0 | 90.0 | 6.5 | 37.0 | 89.0 | 11.0 | 63.8 | 68.1 | — |
| 26 | 52.0 | >100 | >100 | 4.0 | 15.0 | >100 | 50.0 | 70.0 | >100 | 35.3 | 34.1 | 42.6 | — |
| 27 | 2.1 | >100 | >100 | 0.4 | >100 | >100 | — | — | — | 1.2 | 37.1 | 47.2 | 20 |
| 28 | 1.0 | >100 | >100 | 0.1 | >100 | >100 | 5.5 | >100 | >100 | 2.2 | 41.3 | 65.6 | 9.5 |
| 29 | 3.1 | >100 | >100 | 0.3 | 40.0 | >100 | 11.0 | 45.0 | >100 | 4.8 | 34.2 | 52.8 | 34 |
| 30 | >100 | >100 | >100 | 100.0 | >100 | >100 | 1.0 | >100 | >100 | 50.5 | 7.1 | 30.1 | — |
| 31 | 1.1 | >100 | >100 | 0.02 | 40.0 | >100 | 3.8 | 50.0 | >100 | 1.6 | 36.5 | 65.5 | 7.9 |
| 32 | 1.8 | >100 | >100 | 0.0 | 100.0 | >100 | 2.1 | 48.0 | >100 | 1.3 | 39.9 | 61.2 | 4.8 |
| 33 | 0.2 | 11.0 | 60.0 | 0.02 | 2.0 | 80.0 | 0.2 | 0.7 | 4.5 | 0.1 | 34.4 | 35.0 | 7.8 |
| 34 | 10.1 | 90.0 | >100 | 1.8 | 13.0 | >100 | 0.7 | 23.0 | 65.0 | 4.2 | 23.1 | 42.3 | — |
| 35 | >100 | >100 | >100 | 2.0 | >100 | >100 | >100 | >100 | >100 | 2.0 | 24.8 | 41.1 | — |
| 36 | 20.0 | >100 | >100 | 0.7 | 35.0 | >100 | 18.0 | 50.0 | 90.0 | 12.9 | 30.5 | 31.9 | — |
| 37 | 2.0 | 6.0 | 100.0 | 1.1 | 6.0 | 80.0 | 2.6 | 7.0 | 51.0 | 1.9 | 31.7 | 59.9 | 5 |
| 38 | 50.0 | >100 | >100 | 6.5 | 80.0 | >100 | 15.0 | 70.0 | >100 | 23.8 | 20.6 | 34.9 | — |
| 39 | 3.2 | >100 | >100 | 0.7 | 80.0 | >100 | 3.2 | 100.0 | >100 | 2.4 | 9.1 | 18.9 | — |
| 49 | 19.0 | 52.5 | 89.0 | 3.3 | 9.0 | 66.0 | 5.4 | 34.5 | 81.0 | 9.2 | 45.5 | 69.7 | 0.33 |
| 50 | 38.0 | 69.0 | 92.0 | 22.0 | 55.0 | 88.0 | 43.0 | 72.0 | 87.0 | 34.3 | 50.1 | 87.1 | — |
| 51 | 24.0 | 60.0 | 86.0 | 7.5 | 36.0 | 83.0 | 6.0 | 48.0 | 72.0 | 12.5 | 74.5 | 90.8 | — |
| 52 | 12.0 | 53.0 | 82.0 | 5.6 | 9.6 | 69.0 | 10.0 | 54.0 | 75.0 | 9.2 | 83.5 | 95.7 | 0.06 |
| 53 | 5.5 | 20.0 | 49.0 | 3.0 | 17.0 | 51.0 | 2.9 | 7.0 | 30.0 | 3.8 | 88.6 | 94.4 | 0.04 |
| 54 | 8.0 | 24.0 | 68.0 | 4.4 | 20.0 | 59.0 | 19.0 | 25.0 | 64.0 | 10.5 | 67.5 | 89.8 | — |
| 55 | 1.0 | 39.0 | >100 | 1.1 | 6.2 | 48.0 | 0.2 | 0.4 | 56.0 | 0.8 | 85.7 | 95.1 | 0.02 |
| 56 | >100 | >100 | >100 | >100 | >100 | >100 | 0.1 | 0.1 | >100 | >100 | 7.7 | 8.0 | — |
| 57 | 3.0 | 8.0 | 33.0 | 1.8 | 8.0 | 54.0 | 0.2 | 0.4 | 60.0 | 1.7 | 83.5 | 96.9 | 0.07 |
| 58 | 2.1 | 6.0 | 81.0 | 2.8 | 18.0 | 65.0 | 21.0 | 35.0 | 80.0 | 8.6 | 71.1 | 97.6 | 0.04 |
| 59 | 2.3 | 7.0 | 30.0 | 3.0 | 15.0 | 60.0 | 1.5 | 5.5 | 65.0 | 2.3 | 76.6 | 96.3 | 0.03 |
| 60 | 25.0 | 50.0 | 80.0 | 10.0 | 50.0 | 81.0 | 17.0 | 38.0 | 99.0 | 17.3 | 66.6 | 95.0 | — |
| 62 | >100 | >100 | >100 | 90.0 | >100 | >100 | >100 | >100 | >100 | 90.0 | 83.2 | 100.0 | — |
| 76 | 4.2 | 42.5 | >100 | 5.0 | 60.0 | >100 | — | — | — | 4.6 | 42.6 | 89.8 | 0.06 |
| 77 | 2.0 | 70.0 | >100 | 0.5 | 6.0 | 50.0 | 2.6 | 19.0 | >100 | 1.7 | 90.6 | 98.5 | 0.05 |
| 78 | 2.0 | >100 | >100 | 4.0 | 30.0 | >100 | 1.0 | 8.0 | >100 | 2.3 | 87.6 | 91.3 | 0.00 |
| 84 | 2.3 | 21.0 | 70.0 | 1.2 | 21.0 | >100 | 4.2 | 21.0 | 95.0 | 2.6 | 90.0 | 94.3 | 0.06 |
| 85 | 3.3 | 25.0 | 75.0 | 3.1 | 23.0 | >100 | 4.8 | 27.0 | 80.0 | 3.7 | 79.3 | 95.8 | 0.38 |
| 87 | >100 | >100 | >100 | 44.0 | 88.0 | >100 | 20.0 | >100 | >100 | >100 | 43.6 | 81.6 | — |
| 88 | 21.0 | 57.5 | 91.0 | 5.0 | 22.5 | >100 | 7.8 | 37.5 | 78.0 | 11.3 | 81.5 | 95.4 | — |
| 89 | 3.0 | 13.0 | 45.0 | 4.0 | 10.0 | 83.0 | 4.0 | 6.7 | 81.0 | 3.7 | 64.9 | 97.6 | 0.03 |
| 90 | 0.1 | 5.0 | 30.0 | 3.0 | 6.0 | >100 | 0.8 | 6.1 | 82.0 | 1.3 | 78.2 | 98.9 | 0.04 |
| 91 | 46.0 | >100 | >100 | 19.0 | >100 | >100 | 2.0 | 30.0 | 92.0 | 22.3 | 80.8 | 97.3 | — |
| 92 | 6.0 | 40.0 | 82.0 | 7.5 | 46.0 | 87.0 | 10.0 | 16.0 | 76.0 | 7.8 | 88.3 | 100.0 | 0.24 |
| 93 | >100 | >100 | >100 | 54.0 | >100 | >100 | 92.0 | >100 | >100 | 73.0 | 66.5 | 93.4 | — |
| 94 | 4.2 | 26.0 | 74.0 | 3.3 | 22.0 | 80.0 | 1.0 | 10.0 | 70.0 | 2.8 | 92.1 | 100.0 | 0.04 |
| 95 | 6.0 | 40.0 | 72.0 | 3.0 | 14.0 | 66.0 | 0.1 | 11.0 | 64.0 | 3.0 | 60.8 | 92.0 | 0.01 |
| 96 | 8.0 | 21.0 | 60.0 | 6.0 | 27.0 | >100 | 8.0 | 22.0 | 60.0 | 7.3 | 84.1 | 98.5 | 0.01 |
| 97 | 56.0 | >100 | >100 | 6.8 | 85.0 | >100 | 6.5 | 44.0 | 87.0 | 23.1 | 10.2 | 34.2 | — |
| 100 | 40.0 | 70.0 | 96.0 | 8.8 | 46.0 | 82.0 | 28.0 | 62.0 | 84.0 | 25.6 | 77.1 | 96.3 | — |
| 101 | 10.0 | 45.0 | 82.0 | 2.9 | 7.6 | 13.2 | 7.0 | 35.0 | 76.0 | 6.6 | 89.5 | 97.1 | 0.07 |

— denotes 'Not tested'.

HDAC Isoform Selectivity:

Since the Benzamide type compounds are known to have potential for HDAC class I specificity, active compounds in this series were tested for HDAC1 inhibitory activity. The assay was carried out, as previously described using recombinant HDAC1 enzyme (BIOMOL, USA) and following manufacturer's instructions. For determination of $IC_{50}$ values, compounds were tested at five different concentrations (0.001, 0.01, 0.1, 1 and 10 μM): The results shown in Table-2 indicate that these compounds inhibit HDAC1 enzyme at nanomolar concentrations, which are much lower as compared to pan HDAC activity in mouse liver enzyme, indicating HDAC isoform specific activity.

TABLE 2

HDAC1 specific activity

| Test Compound | HDAC1 inhibition ($IC_{50}$, nM) |
| --- | --- |
| 19 | 42 |
| 20 | 150 |
| 24 | 62 |
| 27 | 50 |
| 28 | 36 |
| 29 | 57 |
| 31 | 54 |
| 32 | 52 |

Detection of Histone (H3) Acetylation, Tubulin Acetylation and p21 Induction:

Acetylated histone (H3), acetylated Tubulin and p21 levels were detected in cell lysate by sandwich ELISA method (Cell Signaling Technology, USA, Cat No: 7232, 7204 & 7167 respectively) by following manufacturer's instructions. Briefly, colon cancer cells (HCT116. 10,000/well) were incubated with test compound (1 and 10 μM) or medium (control) for 4 hours at 37° C. in $CO_2$ incubator. The incubation lasted 18 hours for p21 induction. After incubation, cell lysates were prepared in cell lysis buffer by sonication on ice. The lysates were collected after centrifugation and subjected to ELISA test procedure. 100 μL of each diluted cell lysate in dilution buffer (1:1) was added to appropriate capture antibody coated microwells and incubated overnight at 4° C. After washing, 100 μL of detection antibody was added for 1 hour at 37° C. After second washing, 100 μL of HRP-linked secondary antibody was added for 30 min at 37° C. Finally, after appropriate washing, 100 μL of TMB substrate was added for 10 min at 37° C. followed by 100 μL of stop solution. The absorbance of individual wells was read using a spectrophotometer at 450 nm ($A_{450}$). Results were expressed as fold increase ($A_{450}$test/$A_{450}$ control) as compared to control and shown in Table-3. Selected compounds were tested in these assays and were found to cause histone and tubulin acetylation and induce p21 expression several fold higher as compared to untreated control in colon cancer cells. Thus, these compounds demonstrated good cellular HDAC activity in addition to activity in the isolated enzyme preparations.

TABLE 3

Effect of HDAC inhibition in cells (Histone acetylation, Tubulin acetylation and p21 induction)

| | Cellular effects of HDAC Inhibition (Fold increase) | | | | | |
| --- | --- | --- | --- | --- | --- | --- |
| | H3 acetylation | | Tubulin acetylation | | P21 induction | |
| Test compound | 1 μM | 10 μM | 1 μM | 10 μM | 1 μM | 10 μM |
| 19 | 4 | 16 | 1.9 | 4.4 | 1.6 | 2.4 |
| 27 | 1.1 | 1.7 | 1.5 | 3.8 | 1.6 | 3.2 |
| 28 | 1.1 | 5.6 | 1.9 | 6.2 | 1.5 | 2.5 |
| 31 | 0.9 | 1.7 | 1.2 | 2.1 | 1.2 | 2.8 |
| 55 | 4.2 | 7.7 | 10.4 | 11 | 1.3 | 2.5 |

In Vitro Metabolic Stability in Liver Microsomes:

Metabolic stability is defined as the percentage of parent compound lost over time in the presence of liver microsomes, liver S9, or hepatocytes, depending on the goal of the assay. By understanding the metabolic stability of compounds early in discovery, compounds can be ranked for further studies, and the potential for a drug candidate to fail in development as a result of pharmacokinetic reasons may be reduced.

Preparation of phosphate buffer (pH 7.4) and stock solutions of test compound (usually in DMSO or water). Incubation of reaction mixture including cryopreserved mouse or human liver microsomes (1 mg/mL), test compound (50 μM), and NADPH for different time points, e.g. 10, 15, 30, and 60 minutes or single time points, e.g. 60 min. Reaction is started by the addition of NADPH and stopped either immediately or after 60 min for screening assay or at 5, 15, 30 and 60 minutes for a more precise estimate of clearance by addition of ice-cold acetonitrile, followed by sample preparation. Determination of loss of parent compound (compared to zero time point control and/or no NADPH-control) was done using HPLC or LC-MS methods. Metabolism was expressed as percentage of test compound metabolized after a certain time. A marker reaction and marker substrate (e.g. testosterone) was employed as quality criteria of the metabolic capability of the microsomes. (Rodrigues, A. D., Use of in vitro human metabolism studies in drug development. An industrial perspective. *Biochem Pharm,* 48(12): 2147-2156, 1994). Metabolic stability was expressed as % metabolism of the compound after 30 min of incubation in the presence of active microsomes. Compound that had a % metabolism less than 30% were defined as highly stable. Compound that had a metabolism between 30% and 60% were defined as moderately stable and compounds that showed a % metabolism higher than 60% were defined as less stable. Several compounds have been found to be stable and moderately stable.

In Vivo Anti-tumor Activity:

Experiments were carried out using 6-8 week old female athymic SCID (Severe Combined Immune Deficient) mice. The mice were housed in Individually Ventilated Cages (IVC) at constant temperature (22±3° C.) and humidity (50±20%). They had free access to food and water. Tumors were obtained from ATCC, USA and maintained in vivo by subcutaneous (s.c.) passage of tumor fragments (appx 30 mg) in healthy mice according to standard reported procedures. All the animal protocols were approved by the Institutional Animal Ethics Committee, ORLL, Chennai. Each experimental group included 6-8 mice bearing s.c. tumors. Tumors were implanted into the axillary region by puncturing using a Trocar, and tumor growth was monitored by measurement of tumor diameters with a Vernier caliper. Tumor Volume (TV) was calculated according to the following formula:

$$TV(mm^3) = L \times W^2 \times 0.5,$$

Where L and W are the longest diameter and shortest diameter of the tumor, respectively. The compound treatment started when tumors were palpable (150-200 mm³).

Test compound was administered by oral gavage in a volume of 5-10 ml/kg. Drugs were administered once every day for a period of 21 days. Control mice were administered the vehicle at equivalent volume. Tumor size was measured twice every week and body weight was recorded daily prior to dosing.

Test compound (T) efficacy was assessed by calculating several parameters based on tumor volume (TV) with respect to untreated control (C). Parameters routinely assessed were T/C % [$TV_{test}/TV_{control} \times 100$] and Tumor Volume Inhibition (TVI=1−T/C %). Other parameters were Relative Tumor Volume, Percent Tumor volume change, Tumor Delay and Log Cell Kill.

Toxic effects of drug treatment were assessed by Body Weight Loss %. Lethal toxicity was defined as any death in treated groups occurring before any control death. Mice were inspected daily for mortality and toxic clinical signs.

Results of the Xenograft Study:

The compound 19 showed good in-vivo anti-cancer activity in HCT116 (colon) xenograft model. Treatment with compound 19 resulted in maximum Tumor Volume Inhibition (TV1) of 42% as compared to vehicle treated control during the course of the study (FIG. 1). Furthermore, the compound treatment did not result in significant body weight loss or treatment related mortality as compared to control.

We claim:

1. A compound of formula (I):

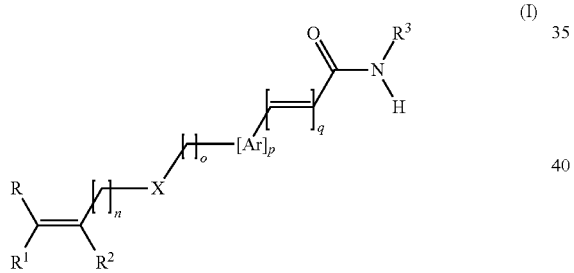

or the tautomeric form, stereoisomer, pharmaceutically acceptable salt or composition or prodrug thereof;

wherein $R^1$ and $R^2$ represent substituted or unsubstituted groups selected from aryl, cycloalkyl, cycloalkenyl, arylalkenyl, heteroarylalkenyl, arylalkynyl, heterocyclyl and heteroaryl;

R represents H, or substituted or unsubstituted groups selected from linear or branched alkyl, aryl, heteroaryl and heterocyclyl;

X represents a group selected from —CONR⁴—, —NR⁴SO₂—, —SO₂NR⁴—, —SO₂O—, —O—SO₂—, —CONR⁴CONR⁴—, —NR⁴CO—, —OCONR⁴—, —NR⁴CONR⁴—, —NR⁴— and —O—;

$R^4$ represents H, or substituted or unsubstituted groups selected from alkyl, aryl, heterocyclyl, heteroaryl, cycloalkyl and cycloalkenyl;

Ar represents substituted or unsubstituted groups selected from aryl and heteroaryl;

$R^3$ represents a group selected from ortho substituted aniline, phenol, amino aryl, hydroxy aryl, amino heteroaryl and —OR⁵;

$R^5$ represents a group selected from H, -COR⁶, substituted or unsubstituted groups selected from alkyl, aryl and heterocyclyl; $R^6$ represents substituted or unsubstituted groups selected from alkyl, aryl and heterocyclyl;

wherein n=0 or 1, o=0-1, p=1, q=0-3;

with the proviso that if X=—OCONH—, then n and p=1; and when the groups R, $R^1$, $R^2$, $R^4$ and Ar have one or more substituents, the substituents are selected from halogens; hydroxy; nitro; cyano; azido; nitroso; amino; hydrazine; formyl; alkyl; alkenyl; alkynyl; haloalkyl group; haloalkoxy; aralkoxy; cycloalkyl; aryl; alkoxy; aryloxy; acyl; acyloxy; acyloxyacyl; heterocyclyl; heteroaryl; alkylamino; acylamino; alkoxycarbonyl; aryloxycarbonyl; alkylsulfonyl; arylsulfonyl; alkylsulfinyl; arylsulfinyl; alkylthio; arylthio; sulfamoyl; alkoxyalkyl and carboxylic acids and its derivatives; the substituents which in turn are optionally further substituted with hydroxy; halogens; nitro; cyano; azido; nitroso; amino; hydrazine; alkyl; alkoxy; aryl; cycloalkyl and heteroaryl.

2. A compound according to claim 1 wherein $R^1$ and $R^2$ represent substituted or unsubstituted groups selected from aryl group comprising phenyl, naphthyl, indanyl and biphenyl; cycloalkyl group comprising cyclopropyl, cyclobutyl, cyclopentyl, cyclohexyl and cyclooctyl; arylalkenyl group comprising phenylethenyl and phenylpropenyl; heteroarylalkenyl group comprising thienylpropenyl, indolylpropenyl; arylalkynyl group comprising phenylethynyl and phenylpropynyl; heterocyclyl group comprising azetidinyl, acridinyl, benzodioxolyl, benzodioxanyl, benzofuranyl and carbazolyl; and heteroaryl group comprising pyridinyl, pyridazinyl, pyrimidyl, triazinyl, pyrrolyl, pyrazolyl, imidazolyl, pyrazinyl, pyrimidinyl, tetrazolyl, furyl, thienyl, thiazolyl, isoxazolyl, oxazolyl, quinolinyl, isoquinolinyl, indolyl, azaindolyl, benzothiazolyl, benzimidazolyl, benzothienyl, benzofuranyl and benzoxazolyl;

R represents H, or substituted or unsubstituted groups selected from linear or branched alkyl group comprising methyl, ethyl, n-propyl, isopropyl, butyl, isobutyl, t-butyl, pentyl, hexyl, heptyl and octyl; aryl group comprising phenyl, naphthyl, indanyl and biphenyl; heteroaryl group comprising pyridinyl, pyridazinyl, pyrimidyl, triazinyl, pyrrolyl, pyrazolyl, imidazolyl, pyrazinyl, pyrimidinyl, tetrazolyl, furyl, thienyl, thiazolyl, isoxazolyl, oxazolyl and quinolinyl; and heterocyclyl group comprising azetidinyl, acridinyl, benzodioxolyl, benzodioxanyl, benzofuranyl and carbazolyl;

$R^4$ is H, or substituted or unsubstituted groups selected from linear or branched alkyl group comprising methyl, ethyl, n-propyl, isopropyl, butyl, isobutyl, t-butyl, pentyl, hexyl, heptyl and octyl; aryl group comprising phenyl, naphthyl, indanyl and biphenyl; heterocyclyl group comprising azetidinyl, acridinyl, benzodioxolyl, benzodioxanyl, benzofuranyl and carbazolyl; heteroaryl group comprising pyridinyl, pyridazinyl, pyrimidyl, triazinyl, pyrrolyl, pyrazolyl, imidazolyl, pyrazinyl, pyrimidinyl, tetrazolyl, furyl, thienyl, thiazolyl, isoxazolyl, oxazolyl and quinolinyl; cycloalkyl group comprising cyclopropyl, cyclobutyl, cyclopentyl, cyclohexyl and cyclooctyl; and cycloalkenyl group comprising of cyclopentenyl, cyclohexenyl, cycloheptenyl and cyclooctenyl;

Ar represents substituted or unsubstituted groups selected from aryl group comprising phenylene, naphthylene, indanylene and biphenylene; and heteroaryl group comprising pyridinylene, pyridazinylene, pyrimidylene, triazinylene, pyrrolylene, pyrazolylene, imidazolylene, pyrazinylene and pyrimidinylene;

$R^5$ represents H, —$COR^6$, or substituted or unsubstituted groups selected from linear or branched alkyl group comprising methyl, ethyl, n-propyl, isopropyl, butyl, isobutyl, t-butyl, pentyl, hexyl, heptyl and octyl; aryl group comprising phenyl, naphthyl, indanyl and biphenyl; and heterocyclyl group comprising azetidinyl, acridinyl, benzodioxolyl, benzodioxanyl, benzofuranyl and carbazolyl;

$R^6$ represents substituted or unsubstituted groups selected from linear or branched alkyl group comprising methyl, ethyl, n-propyl, isopropyl, butyl, isobutyl, t-butyl, pentyl, hexyl, heptyl, octyl; aryl group comprising phenyl, naphthyl, indanyl and biphenyl; and heterocyclyl group comprising azetidinyl, acridinyl, benzodioxolyl, benzodioxanyl, benzofuranyl and carbazolyl;

when the groups R, $R^1$, $R^2$, $R^4$ and Ar have one or more substituents, the substituents are selected from halogens comprising fluorine, chlorine, bromine and iodine; hydroxy; nitro; cyano; azido; nitroso; amino; hydrazine; formyl; alkyl; alkenyl; alkynyl; haloalkyl group comprising trifluoromethyl, trichloromethyl, dichloromethyl and difluoromethyl; haloalkoxy; aralkoxy group comprising benzyloxy and phenylethoxy; cycloalkyl; aryl; alkoxy; aryloxy; acyl; acyloxy; acyloxyacyl; heterocyclyl; heteroaryl; alkylamino group comprising monoalkylamino and dialkylamino; acylamino; alkoxycarbonyl; aryloxycarbonyl; alkylsulfonyl; arylsulfonyl; alkylsulfinyl; arylsulfinyl; alkylthio; arylthio; sulfamoyl; alkoxyalkyl groups and carboxylic acids and its derivatives comprising ester and amide; which in turn are optionally substituted by hydroxy; halogens; nitro; cyano; azido; nitroso; amino; hydrazine; alkyl; alkoxy; aryl; cycloalkyl and heteroaryl.

3. A compound according to claim 1, which is selected from:

N-(2-Aminophenyl)-4-((3-(3,4-difluorophenyl)-2-(4-fluorophenyl)acrylamido)methyl)benzamide;
N-(2-Aminophenyl)-4-((3-(4-methoxyphenyl)-2-(phenyl)acrylamido)methyl)benzamide;
N-(2-Aminophenyl)-4-((3-(2-fluorophenyl)-2-(4-chlorophenyl)acrylamido)methyl)benzamide;
N-(2-Aminophenyl)-4-((3-(4-fluoro-3-trifluoromethylphenyl)-2-(4-trifluoromethylphenyl)acrylamido)methyl)benzamide;
N-(2-Aminophenyl)-4-((3-(4-fluoro-3-trifluoromethylphenyl)-2-(4-nitrophenyl)acrylamido)methyl)benzamide;
N-(2-Aminophenyl)-4-((3-(4-methylthiophenyl)-2-(4-fluorophenyl)acrylamido)methyl)benzamide;
N-(2-Aminophenyl)-4-((3-(5-nitrothiophen-2-yl)-2-(4-fluorophenyl)acrylamido)methyl)benzamide;
N-(2-Aminophenyl)-4-((3-(3,4,5-trimethoxyphenyl)-2-(4-fluorophenyl)acrylamido)methyl)benzamide;
N-(2-Aminophenyl)-4-((3-(2-chloro-4-fluorophenyl)-2-(phenyl)acrylamido)methyl)benzamide;
N-(2-Aminophenyl)-4-((3-(4-fluorophenyl)-2-(phenyl)acrylamido)methyl)benzamide;
N-(2-Aminophenyl)-4-((3-(4-methoxyphenyl)-2-(4-fluorophenyl)acrylamido)methyl)benzamide;
N-(2-Aminophenyl)-4-((3-phenyl-2-phenylacrylamido)methyl)benzamide;
N-(2-Aminophenyl)-4-((3-(2,4,6-trifluorophenyl)-2-(4-fluorophenyl)acrylamido)methyl)benzamide;
N-(2-Aminophenyl)-4-((3-(cyclopropyl)-2-(4-fluorophenyl)acrylamido)methyl)benzamide;
N-2-Aminophenyl)-4-((3-(pyridin-4-yl)-2-(4-fluorophenyl)acrylamido)methyl)benzamide;
N-(2-Aminophenyl)-4-((3-(4-methylthiophenyl)-2-(4-methoxyphenyl)acrylamido)methyl)benzamide;
N-(2-Aminophenyl)-4-((3-(3,5-dimethoxyphenyl)-2-(4-fluorophenyl)acrylamido)methyl)benzamide;
N-(2-Aminophenyl)-4-((3-(4-methylthiophenyl)-2-(thiophen-2-yl)acrylamido)methyl)benzamide;
N-(2-Aminophenyl)-4-((3-(3,4-dimethoxyphenyl)-2-(4-fluorophenyl)acrylamido)methyl)benzamide;
N-(2-Aminophenyl)-4-((3-(4-fluoro-3-methoxyphenyl)-2-(4-fluorophenyl)acrylamido)methyl)benzamide;
N-(2-Aminophenyl)-4((3-(4-methylthiophenyl)-2-(4-trifluoromethylphenyl)acrylamido)methyl)benzamide;
N-(2-Aminophenyl)-4-((3-(quinolin-4-yl)-2-(4-fluorophenyl)acrylamido)methyl)benzamide;
N-(2-Aminophenyl)-4-((3-(4-methylthiophenyl)-2-(2-chlorophenyl)acrylamido)methyl)benzamide;
N-(2-Aminophenyl)-4-((3-(4-methylthiophenyl)-2-(2-fluorophenyl)acrylamido)methyl)benzamide;
N-(2-Aminophenyl)-4-((3-(4-methylthiophenyl)-2-(4-methylphenyl)acrylamido)methyl)benzamide;
N-(2-Aminophenyl)-4-((3-(4-methylthiophenyl)-2-(thiophen-3-yl)acrylamido)methyl)benzamide;
N-(2-Aminophenyl)-4-((3-(3,4-dimethoxyphenyl)-2-(4-methoxyphenyl)acrylamido)methyl)benzamide;
N-(2-Aminophenyl)-4-((3-(3,4-dimethoxyphenyl)-2-(2-fluorophenyl)acrylamido)methyl)benzamide;
N-(2-Aminophenyl)-4-((3-(3,4-dimethoxyphenyl)-2-(4-methylphenyl)acrylamido)methyl)benzamide;
N-(2-Aminophenyl)-4-((3-(3,4-dimethoxyphenyl)-2-(2-chlorophenyl)acrylamido)methyl)benzamide;
N-(2-Aminophenyl)-4-((3-(3,4-dimethoxyphenyl)-2-phenylacrylamido)methyl)benzamide;
N-(2-Aminophenyl)-4-((3-(3,4-dimethoxyphenyl)-2-(3-fluorophenyl)acrylamido)methyl)benzamide;
N-(2-Aminophenyl)-4-(3-(4-carbmethoxyphenyl)-2-(3-chlorophenyl)acrylamido)methyl)benzamide;
N-(2-Aminophenyl)-4-((3-(4-carbmethoxyphenyl)-2-(2-fluorophenyl)acrylamido)methyl)benzamide;
N-(2-Aminophenyl)-4-((3-(4-carbmethoxyphenyl)-2-(4-methoxyphenyl)acrylamido)methyl)benzamide;
N-(2-Aminophenyl)-4-((3-(4-carbmethoxyphenyl)-2-(thiophen-2-yl)acrylamido)methyl)benzamide;
N-(2-Aminophenyl)-4-((3-(3,4-dimethoxyphenyl)-2-(thiophen-2-yl)acrylamido)methyl)benzamide;
N-(2-Aminophenyl)-4-((3-(4-carbmethoxyphenyl)-2-(3,4-difluorophenyl)acrylamido)methyl)benzamide;
N-(2-Aminophenyl)-4-((3-(2,4dimethoxyphenyl)-2-phenylacrylamido)methyl)benzamide;
N-(2-Aminophenyl)-4-((2-(3,4-dimethoxyphenyl)-3-phenylacrylamido)methyl)benzamide;
N-(2-Aminophenyl)-4-((3-(3,4-dimethoxyphenyl)-2-(pyridin-3-yl)acrylamido)methyl)benzamide;
N-(2-Aminophenyl)-4-((3-(3,4-dimethoxyphenyl)-2-(4-methylphenyl)acrylamido))benzamide;
N-(2-Aminophenyl)-4-((3-(3,4-difluorophenyl)-2-(4-methoxyphenyl)acrylamido)methyl)benzamide;
N-(2-Aminophenyl)-4-((3-(4-fluorophenyl)-2-(4-methoxyphenyl)acrylamido)methyl)benzamide;
N-(2-Aminophenyl-4-((3-(4-fluorophenyl)-2-[benzo[d][1,3dioxo-5-yl]acrylamido)methyl)benzamide;
N-(2-Aminophenyl)-4-((3-(4-methylthiophenyl)-2-(3,4-dimethoxyphenyl)acrylamido)methyl)benzamide;

N-(2-Aminophenyl-4-((3-(4-methylthiophenyl)-2-(3,4-methylenedioxyphenyl)acrylamido)methyl)benzamide;
4-((2-(4-Fluorophenyl)-3-(3,4,5-trimethoxyphenyl)acrylamido)methyl)-N-hydroxybenzamide;
4-((2-(4-Methoxyphenyl)-3-(4-fluorophenyl)acrylamido)methyl)-N-hydroxybenzamide;
4-((2-(4-Trifluoromethyllphenyl)-3-(4-fluorophenyl)acrylamido)methyl)-N-hydroxybenzamide;
4-2-(Phenyl)-3-(4-fluorophenyl)acrylamido)methyl)-N-hydroxybenzamide;
4-((2-(4-Fluorophenyl)-3-(4-methylthiophenyl)acrylamido)methyl)-N-hydroxybenzamide;
4-((2-(4-Fluorophenyl)-3-(4-methoxyphenyl)acrylamido)methyl)-N-hydroxybenzamide;
4-((2-(4-Fluorophenyl)-3-(2,4,6-trifluorophenyl)acrylamido)methyl)-N-hydroxybenzamide;
4-((2-(Pyridin-3-yl)-3-(4-methylthiophenyl)acrylamido)methyl)-N-hydroxybenzamide;
4-((2-(2-Chlorophenyl)-3-(4-methylthiophenyl)acrylamido)methyl)-N-hydroxybenzamide;
4-((2-(4-Methoxyphenyl)-3-(4-methylthiophenyl)acrylamido)methyl)-N-hydroxybenzamide;
4-((2-(4-Methylphenyl)-3-(4-methylthiophenyl)acrylamido)methyl)-N-hydroxybenzamide;
4-((2-(Thiophen-3-yl)-3-(4-methylthiophenyl)acrylamido)methyl)-N-hydroxybenzamide;
4-((2-(4-Fluorophenyl)-3-(4-fluoro-3-methoxyphenyl)acrylamido)methyl)-N-hydroxybenzamide;
4-((2-(4-Fluorophenyl)-3-(cyclopropyl)acrylamido)methyl)-N-hydroxybenzamide;
4-((2-(4-Methylphenyl)-3-(3,4-dimethoxyphenyl)acrylamido)methyl)-N-hydroxybenzamide;
4-((2-(4-Fluorophenyl)-3-(3,4-dimethoxyphenyl)acrylamido)methyl)-N-hydroxybenzamide;
4-((2-(4-Methoxyphenyl)-3-(3,4-dimethoxyphenyl)acrylamido)methyl)-N-hydroxybenzamide;
4-((2-(4-Methylphenyl)-3-(3,4-dimethoxyphenyl)acrylamido))-N-hydroxybenzamide;
4-((2-Phenyl-3-(3,4-dimethoxyphenyl)acrylamido)methyl)-N-hydroxybenzamide;
4-((2-[Benzo[d]-1,3dioxo-5-yl]-3-(4-fluorophenyl)acrylamido))-N-hydroxybenzamide;
4-((2-[Benzo[d]-1,3dioxo-5-yl]-3-(4-fluorophenyl)acrylamido)methyl)-N-hydroxybenzamide;
4-((2-(3,4-Dimethoxyphenyl)-3-(4-methylthiophenyl)acrylamido)methyl)-N-hydroxybenzamide;
4-((2-[Benzo[d]-1,3-dioxo-5-yl]-3-(4-methylthiophenyl)acrylamido)methyl)-N-hydroxybenzamide;
4-((2-(4-Methoxyphenyl)-3-(pyridin-3-yl)acrylamido)methyl)-N-hydroxybenzamide;
4-((2-(4-Fluorophenyl)-3-(pyridin-3-yl)acrylamido)methyl)-N-hydroxybenzamide;
4-((2-(4-Methoxyphenyl)-3-(3,4-difluorophenyl)acrylamido)methyl)-N-hydroxybenzamide;
4-((2-Phenyl-3-(4-methylthiophenyl)acrylamido)methyl)-N-hydroxybenzamide;
(1E)-N-(4-(3-(Hydroxyamino)-3-oxoprop-1-enyl)benzyl)-2,3-diphenyl acrylamide;
(1E)-N-(4-(3-(Hydroxyamino)-3-oxoprop-1-enyl)benzyl)-2-(4-fluorophenyl)-3-(4-methylthiophenyl)acrylamide;
(1E)-N-(4-(3-(Hydroxyamino)-3-oxoprop-1-enyl)benzyl)-2-(4-fluorophenyl)-3-(3,4-dimethoxyphenyl)acrylamide;
(1E)-N-(4-(3-(Hydroxyamino)-3-oxoprop-1-enyl)benzyl)-2-(2-fluorophenyl)-3-(3,4-dimethoxyphenypacrylamide;
(1E)-N-(4-(3-(Hydroxyamino)-3-oxoprop-1-enyl)benzyl)-2-(2-phenyl)-3-(4-fluorophenyl)acrylamide;
(1E)-N-(4-(3-(Hydroxyamino)-3-oxoprop-1-enyl)benzyl)-2-(4-fluorophenyl)-3-(3,5-dimethoxyphenyl)acrylamide;
(1E)-N-(4-(3-(Hydroxyamino)-3-oxoprop-1-enyl)benzyl)-2-(4-fluorophenyl)-3-(3,4,5-trimethoxyphenyl)acrylamide;
(1E)-N-(4-(3-(Hydroxyamino)-3-oxoprop-1-enyl)benzyl)-3-(4-fluorophenyl)-2-(4-methoxyphenyl)acrylamide;
3-(3,4-Dimethoxyphenyl)-2-(4-methoxyphenyl)allyl-4-(2-aminophenylcarbamoyl)benzylcarbamate;
3-(3,4-Dimethoxyphenyl)-2-(4-methylphenyl)allyl-4(2-aminophenylcarbamoyl)benzylcarbamate and
the pharmaceutically acceptable salts thereof.

4. A process for the preparation of a compound of formula (I) according to claim 1, comprising reacting the compounds of formulae 1d or 1g with $R^3NH_2$;

wherein Y is —OH, —O-Alkyl and R, $R^1$, $R^2$, $R^3$, Ar, o, q are as defined for formula (I).

5. A pharmaceutical composition comprising a compound of formula (I), according to claim 1, as an active ingredient, along with a pharmaceutically acceptable carrier, diluent, excipient or solvate.

6. A pharmaceutical composition according to claim 5, wherein the composition is in the form of a tablet, capsule, powder, syrup, solution, aerosol or suspension.

7. A method for inhibiting HDAC in a cell comprising treating the cell with an effective amount of a compound according to claim 1.

8. A method for the treatment of a condition mediated by HDAC selected from lung cancer, colon cancer and glioma, comprising administering to a subject suffering from said condition mediated by HDAC, a therapeutically effective amount of a compound according to claim 1.

9. A method for the treatment of cancer selected from lung cancer, colon cancer and glioma, comprising administering to a subject suffering from said cancer, a therapeutically effective amount of a compound according to claim 1.

10. A pharmaceutical composition comprising a compound of formula (I), according to claim 3, as an active ingredient, along with a pharmaceutically acceptable carrier, diluent, excipient or solvate.

11. A method for the treatment of a condition mediated by HDAC selected from B-cell lymphoma, T-cell lymphoma, leukemia, breast cancer, lung cancer, ovarian cancer, prostate cancer, head cancer, neck cancer, renal cancer, gastric cancer, colon cancer, pancreatic cancer and brain cancer, comprising administering to a subject suffering from said condition mediated by HDAC, a therapeutically effective amount of a compound according to claim 1.

12. A method for inhibiting HDAC in a cell comprising treating the cell with an effective amount of a compound according to claim 3.

13. A method for the treatment of a condition mediated by HDAC selected from lung cancer, colon cancer and glioma, comprising administering to a subject suffering from said condition mediated by HDAC, a therapeutically effective amount of a compound according to claim 3.

14. A method for the treatment of cancer selected from lung cancer, colon cancer and glioma, comprising administering to a subject suffering from said cancer, a therapeutically effective amount of a compound according to claim 3.

15. A method for the treatment of a condition mediated by HDAC selected from B-cell lymphoma, T-cell lymphoma, leukemia, breast cancer, lung cancer, ovarian cancer, prostate cancer, head cancer, neck cancer, renal cancer, gastric cancer, colon cancer, pancreatic cancer and brain cancer, comprising administering to a subject suffering from said condition mediated by HDAC, a therapeutically effective amount of a compound according to claim 3.

* * * * *